US008507411B2

(12) United States Patent
Langenhan

(10) Patent No.: US 8,507,411 B2
(45) Date of Patent: *Aug. 13, 2013

(54) NEOGLYCORANDOMIZATION AND DIGITOXIN ANALOGS

(75) Inventor: Joseph M. Langenhan, Seattle, WA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 874 days.

This patent is subject to a terminal disclaimer.

(21) Appl. No.: 12/197,735

(22) Filed: Aug. 25, 2008

(65) Prior Publication Data

US 2009/0075842 A1 Mar. 19, 2009

Related U.S. Application Data

(63) Continuation-in-part of application No. 11/166,881, filed on Jun. 24, 2005, now Pat. No. 7,754,874.

(60) Provisional application No. 60/521,721, filed on Jun. 24, 2004, provisional application No. 60/957,623, filed on Aug. 23, 2007.

(51) Int. Cl.
*C40B 40/12* (2006.01)
*C40B 50/00* (2006.01)
*A61K 31/7034* (2006.01)
*A61K 31/7056* (2006.01)

(52) U.S. Cl.
USPC ................... 506/19; 506/23; 514/42

(58) Field of Classification Search
USPC .................................... 506/19, 23
See application file for complete search history.

(56) References Cited

U.S. PATENT DOCUMENTS

| 4,160,452 | A | 7/1979 | Theeuwes |
| 4,256,108 | A | 3/1981 | Theeuwes |
| 4,265,874 | A | 5/1981 | Bonsen |
| 4,663,308 | A | 5/1987 | Saffran |
| 4,777,049 | A | 10/1988 | Magruder |

OTHER PUBLICATIONS

Definition of analogue, Oxford English Dictionary, http://www.oed.com/, accessed online on Jan. 25, 2011.*
Definition of alkaloid, Oxford English Dictionary, http://www.oed.com/, accessed online on Jan. 27, 2011.*
Takekawa et al. J. Nat. Prod., 2006, 69(10), p. 1503-1505, Publication Date (Web): Oct. 11, 2006.*
Ahmed et al. J. Am. Chem. Soc., 2006, 128, p. 14224-14225, Published on Web Oct. 13, 2006.*
Ahmed, et al. "Interaction of (Na+, K+)-ATPases and Digitalis Genins" 1983 J.Bio. Chem, 258 (13) 8092-8097.
Carrasco, et al., "A versatile set of aminooxy amino acids for the synthesis of neoglycopeptides" 2003 J. Org. Chem. 68, 8853-8858.
Carrasco, et. al., "Synthesis of N-Fmoc-O-(N'-Boc-N'-methyl)-aminohomoserine, an amino acid for the facile preparation of neoglycopeptides" 2003 J. Org. Chem. 68, 195.
Cervigni, et al., "Synthesis of Glycopeptides and Lipopeptides by chemoselective Ligation," 1996 Angew. Chem. Int. 31. Ed. 35:11 pp. 1230-1232.
Chantrapromma, et al., "Bis[14beta-hydroxy-3beta-O-(L-thevetosyl)-5beta-card-20(22)-enolide] methanol solvate monohydrate and 3beta-O-(L-2'-o-acetylthevetosyl)-14beta-hydroxy-5beta-card-20(22)-enolide" 2003 Acta Crystallogr C.; 59(Pt 2):o68-70.
Chisholm, et al., "Regiocontrolled synthesis of the antitumor antibiotic AT2433-A1" 2000 J Org Chem. 65 (22):7541-53.
Clardy, et al., "Lessons from natural molecules" 2004 Nature 432 (7019):829-37.

Daniel, et al., "Apoptosisi-mediated selective killing of malignant cells by ardiac steroids: maintenance of cytotoxicity and loss of cardiac activity of chemically modified deriatives," 2003 Internatl. Immunopharmacol. 3, pp. 1791-1801.
Definition of erythromycin, The Merck Index 2006, Merck & Co., 14th edition, accessed online http://themerckindex.cambridgesoft.com/TheMerckIndex/index.asp on Aug. 31, 2007.
Dmitrieva, et al., "Cardiotonic steroids: potential endogenous sodium pump ligands with diverse function" 2002 Exp Bioi Med (Maywood) 227(8):561-9.
Dobson CM "Chemical space and biology" 2004 Nature 16; 432(7019):824-8.
Fairchild, et al., "Isolation of Amplified and overexpressed DNA sequences from Adriamycin-resistant human breast cancer cells," 1987 Cancer Res. 47, 5141-5148.
Filira, et al., "Opioid peptides: synthesis and biological properties of (N-glucosyl, N-methoxy)-alpha, gamma-diamino-(s)-butanoyl!4-deltorphin-1-neoglycopeptide and related analogs" 2003 Organic & Biomolecular Chemistry vol. 1 pp. 3059-3063.
Friend, et al., "A colon-specific drug-delivery system based on drug glycosides and the glycosidases of colonic bacteria" 1984 J Med Chem 27(3):261-6.
Fu, et al., "Antibiotic optimization via in vitro glycorandomization" 2003 Nat. Biotechnol. 21(12): 1467-1469.
Fullerton, et al., "A crystallographic, conformational energy, and biological study of Actodigin (AY-22,241) and its genin," 1980 Mol Pharmacol. 17(1):43-51.
Fun, et al., "Absolute configuation of 14 b-hydroxy 3 o (1 thevetosyl) 5 card 20 (22) enolide chloroform disolvate," 2003 Acta Crystallogr., Sect. E: Struct. Rep. Online, 59, o1694.
Gill, et al. "Development of an HTS assay for na+, k+a -TPase using nonradioactive rubidium ion uptake" 2004 Assay Drug Dev Technol. 2(5):535-42.
Go, et al. "Digoxin, C14 H64 O14" 1979 Cryst. Struct. Commun. 8, 149.
Go, et al., "Digoxigenin Monodigitoxoside" 1982 Cryst. Struct. Commun. 11, 279.
Go, et al., "Structural studies on the biosides of digitalis lanata: bisdigitoxosides of digitoigenin, gitoxigenin and digoxigenin," 1989 Acta Crystallogr., Sect. B: Struct. Sci., 45, 306.
Go, et al., "Structure of Digoxin," 1980 Acta Crystallogr., Sect.B: Struct. Crystallogr. Cryst. Chem. 36, 1811.
Go, et al., "Structure of Gitoxin," 1980 Acta Crystallogr., Sect. B: Struct. Crystallogr. Cryst. Chem. 36, 3034.
Hang, et al., "Chemoselective approaches to glycoprotein assembly" 2001 Ace Chem Res. 34(9):727-36.

(Continued)

*Primary Examiner* — Shaojia Anna Jiang
*Assistant Examiner* — Jonathan S Lau
(74) *Attorney, Agent, or Firm* — Quarles & Brady LLP

(57) ABSTRACT

The present invention provides methods of producing libraries of compounds with enhanced desirable properties and diminished side effects as well as the compounds produced by the methods. In preferred embodiments, methods of the present invention use a universal chemical glycosylation method that employs reducing sugars and requires no protection or activation. In a preferred embodiment, the invention provides a library of neoglycoside digitoxin analogs that includes compounds with significantly enhanced cytotoxic potency toward human cancer cells and tumor-specificity, but are less potent $Na^+/K^+$-ATPase inhibitors in a human cell line than digitoxin.

3 Claims, 9 Drawing Sheets

(56) References Cited

OTHER PUBLICATIONS

Hardy, et al., "Evaluation of an enteric-coated delayed-release 5 aminosalicylic acid tablet in patients with inflammatory bowel disease," 1987 Aliment. Pharmacol. Therap. 1, 273-280.

Haux, "Digitalis; impinges on more than just the (ion0) pump," 2002 Med. Hypotheses 59, 781.

Ingallinella, et. al., "A New Method for Chemoselective Conjugation of Unprotected Peptides to Dauno- and Doxorubicin" 2001 Bioorg. Med. Chem. Lett. 11,1343-1346.

Johansson, et al., "Cytotoxicity of digitoxin and related cardiac glycosides in human tumor cells" 2001 Anti-Cancer Drugs 12(5) 475-483.

Johnson, et al., "Multiplex gene expression analysis for high-throughput drug discovery: screening and analysis of compounds affecting genes overexpressed in cancer cells" 2002 Mol Cancer Ther. 1(14):1293-304.

Kartha, et al., "Oleandrin, C32H48O9" 1981 Cryst. Struct. Commun. 10, 1323.

Kihara, et al., "Cardiac Glycosides: 3. Synthesis of D-Digitoxose Analogues" 1984 Tetrahedron 40, 1121.

Kolb, et al., "Click Chemistry: Diverse Chemical Function from a Few Good Reactions" 2001 Angew. Chern. Int. Ed., 40, 2004-2021.

Langenhan, et al., "Recent carbohydrate-based chemoselective ligation applications," 2005 Curr. Org. Synth. 2, 59-8.

Lin H. "Inhibitory effect of digoxin on testosterone secretion through mechanisms involving decreases of cyclic AMP production and cytochrome P450scc activity in rat testicular interstitial cells" 1998 Br. J. Pharmacol. 125, 1635-1640.

Lin, et al., "Involvement of Cdk5/p25 in digoxin-triggered prostate cancer cell apoptosis" 2004 J Biol Chem. 279 (28):29302-7 Epub Apr. 30, 2004.

Messerschmidt, "Ouabain, C29H44O12" 1980 Cryst. Struct. Commun. 9, 1185.

Paula, et al., "Interactions between cardiac glycosides and sodium/potassium-ATPase: three-dimensional structure-activity relationship models for ligand binding to the E2-Pi form of the enzyme versus activity inhibition" 2005 Biochemistry 44(2):498-510.

Peri, et al., "Chemo- and Stereoselective Glycosylation of Hydroxylamino Derivatives: A Versatile Approach to Glycoconjugates" 1998 Tetrahedron Elsevier Science Publishers—Amsterdam pp. 12269-12278.

Peri, et. al., "Solution and solid-phase chemoselective synthesis of 1-6-amino(methoxy) di- and trisaccharide analogues" 2002 Chem. Comm. 1504.

Peri, et. al., "Synthesis and conformational analysis of novel N(OCH3)-linked disaccharide analogues" 2004 Chem. Eur. 10, 1433-1444.

Peri, et. al., "Chemoselective ligation in glycochemistry" 2004 Chem. Commun. (Camb). (6):623-7. Epub Nov. 14, 2003.

Pfeiffer, et al. "The molecular and crystal structure of 3 b-0- (2',3'-0-isorylidene—L-rhamnopyranosyl)-digitoxigenin," 1986 J. Cryst. Res. and Technol. 21, 223.

Picconi, et. al., "A screen for drugs that protect against the cytotoxicity of polyglutamine-expanded androgen receptor." 2004 Hum Mol Genet. 13(4):437-46. Epub Jan. 6, 2004.

Rathore, et. al., "Cardiac glycosides. 7. Sugar stereochemistry and cardiac glycoside activity" 1986 J Med Chem. (10):1945-52.

Repke, et al., 1995 Agnew. Chem Int. Ed. Engl. 34 pp. 282-294.

Scudiero, et. al., "Cell line designation change: multidrug-resistant cell line in the NCI anticancer screen" 1998 J Natl Cancer Inst. 90(11):862.

Sreenivasan, et al., "Oleandrin suppresses activation of nuclear transcription factor kb and activator protein1 and potentiates apoptosis induced by ceramide," 2003 Biochem. Pharmacol. 66, 2223-2239.

Srivastava, et. al., "Digitoxin mimics gene therapy with CFTR and suppresses hypersecretion of IL-8 from cystic fibrosis lung epithelial cells" 2004 Proc Natl Acad Sci USA 101(20):7693-8. Epub May 10, 2004.

Stenkvist B. "Cardenolides and cancer" 2001 Anticancer Drugs. 12(7):635-8.

Svensson, et al., "Digoxin inhibits neuroblastoma tumor growth in mice," 2005 Anticancer Res. 25, 207-212.

Tanigawara, et al., "Transport of Digoxin by human P-glycoprotein expresssed in a porcine kidney epithelial cell line," 1992 J. Pharmacol. Exp. Ther. 263, 840-845.

Thorson, et al., "Nature's carbohydrate chemists: the enzymatic glycosylation of bioactive bacterial metabolites," 2001 Curr. Org. Chern. 5, 139-150.

Van Quaquebeke et. al., "Identification of a novel cardenolide (2"-oxovoruscharin) from *Calotropis procera* and the hemisynthesis of novel derivatives displaying potent in vitro antitumor activities and high in vivo tolerance: structure-activity relationship analyses." 2005 J Med Chem. 48(3):849-56.

\* cited by examiner

NEOGLYCORANDOMIZATION AND DIGITOXIN ANALOGS

RELATED APPLICATIONS

This application is a continuation-in-part of U.S. patent application Ser. No. 11/166,881 filed on Jun. 24, 2005, which claims benefit of U.S. Provisional Patent Application No. 60/521,721 filed on Jun. 24, 2004, both of which are incorporated by reference herein in their entirety. This application also claims the benefit of U.S. Provisional Patent Application No. 60/957,623 filed on Aug. 23, 2007, which is incorporated by reference herein in its entirety.

GOVERNMENT SUPPORT

Not applicable.

FIELD OF THE INVENTION

The present invention generally relates to glycosylated secondary metabolites. Specifically, the present invention relates to methods, techniques and uses of neoglycorandomization, especially as applied to digitoxin, indolocarbazole and anthracyline analogs.

BACKGROUND OF THE INVENTION

The natural product pool, which contains many glycosylated secondary metabolites, is the source of over half the world's drug leads. Carbohydrate appendages often play a key role in drug-target interactions. Therefore, alteration of glycosylation patterns on secondary metabolites is a potential strategy for the generation of novel therapeutics.

Carbohydrates mediate many essential biological processes. For example, the saccharide-containing macromolecules that decorate cell surfaces are vital to a variety of cellular functions including cell-cell recognition, apoptosis, differentiation, and tumor metastasis. In a similar fashion, glycosylated natural products contain sugar attachments essential for their activity and continue to serve as reliable platforms for the development of many of existing front-line drugs (Clardy, J. et al., Nature (2004) 432, 829-837; Thorson, J. S. et al., Curr. Org. Chem. (2001) 5, 139-150). While the diverse chemical space accessible by carbohydrates contributes to a remarkably vast array of biological function (Dobson, C. M. Nature (2004) 432, 824-865), a precise understanding of the relationship between sugars and biological activity remains limited by the availability of convenient and effective glycosylation tools (Langenhan, J. M. et al., Curr. Org. Synth. (2005) 2, 59-8).

Digitoxin (1) is a glycosylated natural product with numerous actions and therapeutic uses. In addition to its well-known cardiac activity, which is mediated by inhibition of the plasma membrane $Na^+/K^+$-ATPase (Paula, S. et al., Biochemistry (2005) 44, 498-510), digitoxin has demonstrated in vitro anti-cancer properties (Johansson, S. et al., Anti-Cancer Drugs (2001) 12, 475-483) and patient profiling suggests the survival rate of cancer patients taking digitoxin is statistically enhanced (Stenkvist, B. Anti-Cancer Drugs (2001) 12, 635-636; Haux, J. et al., BMC Cancer (2001) 1, 11). Cardiac glycosides were also recently noted to inhibit the expression of four genes that are overexpressed in prostate cancer cells, including transcription factors and the apoptosis inhibitor survivin (Johnson, P. H. et al., Molecular Cancer Therapeutics (2002) 1, 1293-1304), and to provide protective effects against polyglutamine-based diseases (Piccioni, F. et al., Hum. Mol. Genet. (2004) 13, 437-446). Digitoxin also inhibits activation of the NF-κB signaling pathway in cystic fibrosis (CF) cells, suppressing hypersecretion of IL-8, a protein implicated in lung inflammation, from CF lung epithelial cells (Srivastava, M. et. al., Proc. Natl. Acad. Sci. (2004) 101, 7693-7698). Given that the attached sugars are implicated as mediators of the unique spectrum of biological properties exhibited by cardiac glycosides (Rathore, H. et al., J. Med. Chem. (1986) 29, 1945-1952), digitoxin provides an excellent model to examine the general utility of neoglycosylation to efficiently construct a glycorandomized library and to directly assess the biological impact of varying the sugars attached to a given natural product-based drug.

SUMMARY OF THE INVENTION

The present invention provides methods of producing libraries of compounds with enhanced desirable properties and diminished side effects as well as the libraries and compounds produced by the methods. In preferred embodiments, methods of the present invention use a universal chemical glycosylation method that employs reducing sugars and requires no protection or activation. In a preferred embodiment, the invention provides a library of neoglycoside digitoxin analogs that includes compounds with significantly enhanced cytotoxic potency toward human cancer cells and tumor-specificity, but are less potent $Na^+/K^+$-ATPase inhibitors in a human cell line than digitoxin.

In general, the present invention provides neoglycosides produced by the reaction of an aglycon having a secondary alkoxyamine and a reducing sugar selected from the group consisting of L-sugars, D-sugars, deoxy-sugars, dideoxy-sugars, glucose epimers, substituted sugars, uronic acids and oligosaccharides. Suitable aglycons include digitoxin analogs, non-digoxigenin steroids, including dihydroxytestosterone derivatives, indolocarbazoles, anthracylines, macrolides, peptides, including ribosomal peptides as well as non-ribosomal peptides such as vancomycin, and alkaloids, such as colchicine and 3-alkylpyridine alkaloids. Suitable reducing sugars include L-ribose, D-ribose, L-fucose, D-fucose, 2-deoxy-D-galactose, 3-deoxy-D-glucose, 6-deoxy-D-glucose, 2-deoxy-2-fluoro-D-glucose, 6-deoxy-6-fluoro-D-glucose, L-lyxose, D-lyxose, L-rhamnose, L-allose, D-allose, L-altrose, D-altrose, L-galactose, D-galactose, L-xylose, D-xylose, D-gulose, L-mannose, D-mannose, L-idose, D-idose, L-mycarose, 6-keto-D-galactose, L-arabinose, D-arabinose, N-acetyl-D-galactosaminose, melibiose, lactose, maltose, D-galacturonose, L-talose, D-talose, 6-deoxy-6-azo-D-mannose, L-glucose, D-glucose, O-D-glucose, R—C(3)aglycon, S—C(3) aglycon.

In another embodiment, the present invention comprises neoglycosides produced by the reaction of an aglycon having a secondary alkoxyamine and a reducing sugar from the group consisting of L-riboside, D-riboside, L-fucoside, D-fucoside, 2-deoxy-D-galactoside, 3-deoxy-D-glucoside, 6-deoxy-D-glucoside, 2-deoxy-2-fluoro-D-glucoside, 6-deoxy-6-fluoro-D-glucoside, L-lyxoside, D-lyxoside, L-rhamnoside, L-alloside, D-alloside, L-altroside, b-altroside, L-galactoside, D-galactoside, L-xyloside, D-xyloside, D-guloside, L-mannoside, D-mannoside, L-idoside, D-idoside, L-mycaroside, 6-keto-D-galactoside, L-arabinoside, D-arabinoside, N-acetyl-D-galactosaminoside, melibioside, lactoside, maltoside, D-galacturonoside, L-taloside, D-taloside, 6-deoxy-6-azido-D-mannoside, L-glucoside, D-glucoside, O-D-glucoside, R—C(3)aglycon and S—C(3) aglycon.

In preferred embodiments, the invention provides neoglycosides of the formula:

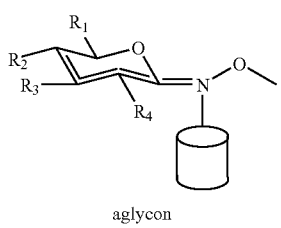

aglycon

In one preferred embodiment, the invention provides a library of neoglycosides comprising a plurality of neoglycosides selected from the group consisting of L-riboside (5β), D-riboside (6β), L-fucoside (7β), D-fucoside (8β), 2-deoxy-D-galactoside (9β), 3-deoxy-D-glucoside (10β), 6-deoxy-D-glucoside (11β), 2-deoxy-2-fluoro-D-glucoside (12β), 6-deoxy-6-fluoro-D-glucoside (13β), L-lyxoside (14β), D-lyxoside (15β), L-rhamnoside (16β), L-alloside (17β), D-alloside (18β), L-altroside (19β), D-altroside (20β), L-galactoside (21β), D-galactoside (22β), L-xyloside (23β), D-xyloside (24β), D-guloside (25β), L-mannoside (26β), D-mannoside (27β), L-idoside (28β), D-idoside (29β), L-mycaroside (30β), 6-keto-D-galactoside (31β), L-arabinoside (32β), D-arabinoside (33β), N-acetyl-D-galactosaminoside (34β), melibioside (35β), lactoside (36β), maltoside (37β), D-galacturonoside (38β), L-taloside (39β), D-taloside (40β), 6-deoxy-6-azido-D-mannoside (41β), L-glucoside (42β), D-glucoside (4β), O-D-glucoside (43β), R—C(3)aglycon (3β), S—C(3) aglycon (3α), L-riboside (5α), D-riboside (6α), L-fucoside (7α), D-fucoside (8α), 2-deoxy-D-galactoside (9α), 3-deoxy-D-glucoside (10α), 6-deoxy-D-glucoside (11α), 2-deoxy-2-fluoro-D-glucoside (12α), 6-deoxy-6-fluoro-D-glucoside (13α), L-lyxoside (14α), D-lyxoside (15α), L-rhamnoside (16α), L-alloside (17α), D-alloside (18α), L-altroside (19α), D-altroside (20α), L-galactoside (21α), D-galactoside (22α), L-xyloside (23α), D-xyloside (24α), D-guloside (25α), L-mannoside (26α), D-mannoside (27α), L-idoside (28α), D-idoside (29α), L-mycaroside (30α), 6-keto-D-galactoside (31α), L-arabinoside (32α), D-arabinoside (33α), N-acetyl-D-galactosaminoside (34α), melibioside (35α), lactoside (36α), maltoside (37α), D-galacturonoside (38α), L-taloside (39α), D-taloside (40α), 6-deoxy-6-azido-D-mannoside (41α), L-glucoside (42α) and D-glucoside (4α).

In one embodiment, the invention comprises a library comprising a plurality of neoglycosides produced by the reaction of an aglycon having a secondary alkoxyamine and at least one reducing sugar selected from the group consisting of L-sugars, D-sugars, deoxy-sugars, dideoxy-sugars, glucose epimers, substituted sugars and oligosaccharides. In another embodiment, the invention comprises a collection comprising at least two compounds produced by the reaction of an aglycon having a secondary alkoxyamine and a reducing sugar from the group consisting of L-ribose, D-ribose, L-fucose, D-fucose, 2-deoxy-D-galactose, 3-deoxy-D-glucose, 6-deoxy-D-glucose, 2-deoxy-2-fluoro-D-glucose, 6-deoxy-6-fluoro-D-glucose, L-lyxose, D-lyxose, L-rhamnose, L-allose, D-allose, L-altrose, D-altrose, L-galactose, D-galactose, L-xylose, D-xylose, D-gulose, L-mannose, D-mannose, L-idose, D-idose, L-mycarose, 6-keto-D-galactose, L-arabinose, D-arabinose, N-acetyl-D-galactosaminose, melibiose, lactose, maltose, D-galacturonose, L-talose, D-talose, 6-deoxy-6-azo-D-mannose, L-glucose, D-glucose, O-D-glucose, R—C(3)aglycon, S—C(3) aglycon.

In some embodiments, the aglycon having a secondary alkoxyamine is selected from digitoxin analogs, non-digoxigenin steroids, including dihydroxytestosterone derivatives, indolocarbazoles, anthracylines, macrolides, peptides, and alkaloids, including 3-alkylpyridine alkaloids. In preferred embodiments, the aglycon having a secondary alkoxyamine is selected from the group consisting of 3α, 3β and mixtures thereof.

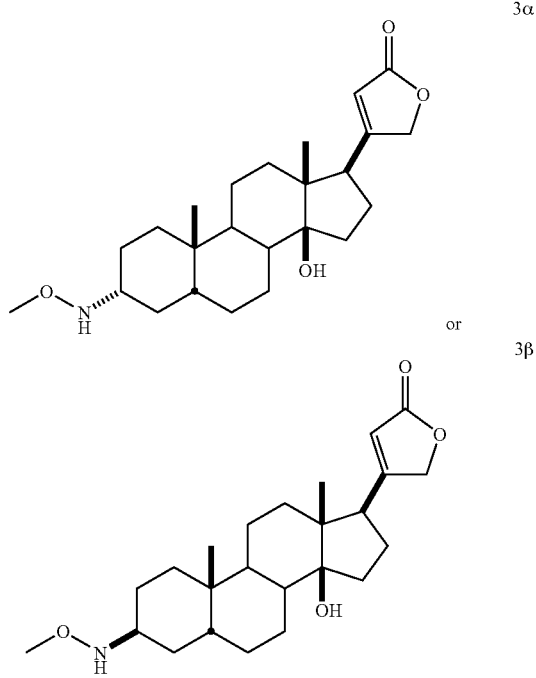

In certain embodiments, the present invention provides a method of making a library comprising a plurality of neoglycosides comprising the steps of providing at least two reducing sugars of the formula:

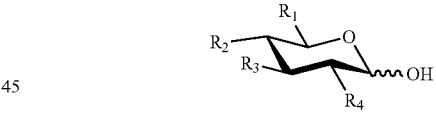

where $R_1$, $R_2$, $R_3$, and $R_4$ are independently selected from —H, —OH, —N$_3$, —NH$_2$, —CH$_3$, —CH$_2$OH, —CN$_3$, —CH$_2$NH, —CH$_2$SH, —CNH$_2$, —CH$_2$N$_3$, —COOH, —COCH$_3$, —CXH$_2$, —CX$_2$H, and where X is Cl, Br, F, or I; and contacting the reducing sugars with at least one aglycon having a secondary alkoxyamine to form a neoglycoside. In preferred embodiments, the aglycon having a secondary alkoxyamine is a digitoxin methoxyamine. In some embodiments, the aglycon having a secondary alkoxyamine is selected from digitoxin analogs, non-digoxigenin steroids, including dihydroxytestosterone derivatives, indolocarbazoles, anthracylines, macrolides, peptides, and alkaloids, including 3-alkylpyridine alkaloids. In certain embodiments, the step of contacting is performed at a temperature from about 40 to about 60 degrees Celsius. In certain embodiments, the step of contacting is performed in the presence of a 3:1 mixture of DMF and AcOH.

In another embodiment, the present invention provides a pharmaceutical composition of a neoglycoside of the present invention, a pharmaceutically acceptable ester, salt or prodrug thereof combined with a pharmaceutically acceptable carrier. In a further embodiment, the present invention provides a method of treating a subject having cancer cells comprising the step of contacting the cancer cells with an effective amount of the neoglyoside of the present invention, or pharmaceutically acceptable ester, salt or prodrug thereof. Preferred neoglycosides include L-riboside (5β), D-lyxoside (15β), L-xyloside (23β), D-mannoside (27β), D-arabinoside (33β), D-taloside (40β) and a mixture thereof. Also provided is the use of a neoglycoside of the present invention for the manufacture of a medicament for the treatment of cancer.

In another embodiment, the present invention provides a neoglycoside having the structure:

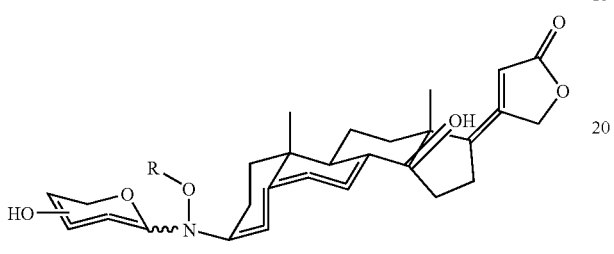

where R is —CH₃, —CH₂CH₃, —CH(CH₃)₂, allyl, benzyl, —CH₂CH₂CH₃, —CH(CH₃)CH₂CH₃, cyclopentyl or cyclohexyl; and the sugar is L-ribose or L-xylose.

In another embodiment, the present invention provides neoglycosides having the structure:

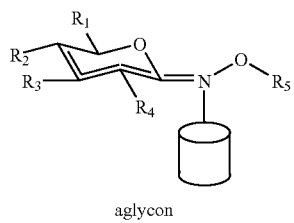

where $R_1$, $R_2$, $R_3$, and $R_4$ of the sugar are independently selected from —H, —OH, —N₃, —NH₂, —CH₃, —CH₂OH, —CN₃, —CH₂NH, —CH₂SH, —CNH₂, —CH₂N₃, —COOH, —COCH₃, —CXH₂, or —CX₂H, where X is Cl, Br, F, or I; where $R_5$ is —CH₃, —CH₂CH₃, —C(CH₃)₃, —CH(CH₃)₂, allyl or benzyl; and where the aglycon is a digitoxin analog, a non-digoxigenin steroid, including a dihydroxytestosterone derivative, an indolocarbazole, an anthracyline, a macrolide, a peptide, or an alkaloid, including a 3-alkylpyridine alkaloid. In one aspect of the present invention, a neoglycoside library comprising at least two different neoglycosides is provided.

In another embodiment, the present invention provides an amphemedoside glycoside. Amphimedisides provided by this embodiment include without limitation amphimedoside A, amphimedoside B, amphimedoside C, amphimedoside D, and amphimedoside E.

In a further embodiment, the present invention provides a method for providing a neoglycoside comprising reacting: (i) an aglycon selected from a digitoxin analog, a non-digoxigenin steroid, including a dihydroxytestosterone derivative, an indolocarbazole, an anthracyline, a macrolide, a peptide, and an alkaloid, including a 3-alkylpyridine alkaloid, wherein said aglycon bears a secondary oxyamine; and (ii) a reducing sugar selected from a L-sugar, a D-sugar, a deoxy-sugar, a dideoxy-sugar, a glucose epimer, a substituted sugar, a uronic acid, or an oligosaccharide to thereby provide a neoglycoside. The reducing sugar is preferably selected from the group consisting of L-ribose, D-ribose, L-fucose, D-fucose, 2-deoxy-D-galactose, 3-deoxy-D-glucose, 6-deoxy-D-glucose, 2-deoxy-2-fluoro-D-glucose, 6-deoxy-6-fluoro-D-glucose, L-xylose, D-xylose, L-rhamnose, L-allose, D-allose, L-altrose, D-altrose, L-galactose, D-galactose, L-xylose, D-xylose, D-gulose, L-mannose, D-mannose, L-idose, D-idose, L-mycarose, 6-keto-D-galactose, L-arabinose, D-arabinose, N-acetyl-D-galactosaminose, melibiose, lactose, maltose, D-galacturonose, L-talose, D-talose, 6-deoxy-6-azo-D-mannose, L-glucose, D-glucose, O-D-glucose, R—C(3)aglycon, S—C(3) aglycon and mixtures thereof. Further, the aglycon preferably has a structure according to:

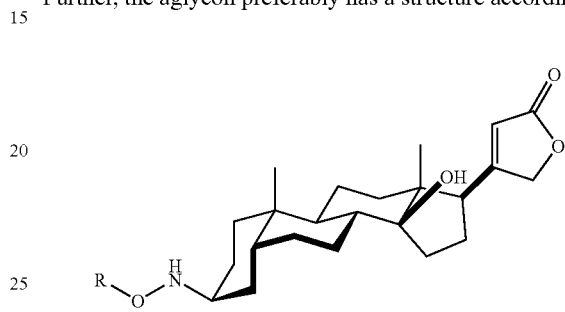

where R is —CH₃, —CH₂CH₃, —CH(CH₃)₂, allyl, benzyl, —CH₂CH₂CH₃, —CH(CH₃)CH₂CH₃, cyclopentyl or cyclohexyl.

The invention also provides a method of making a neoglycoside library comprising providing a plurality of reducing sugars selected from the group consisting of a L-sugar, a D-sugar, a deoxy-sugar, a dideoxy-sugar, a glucose epimer, a substituted sugar, a uronic acid, an oligosaccharide and mixtures thereof; and contacting the reducing sugars with at least one aglycon having a secondary oxyamine to form a plurality of neoglycosides. In a preferred embodiment, the aglycon is a digitoxin analog, a non-digoxigenin steroid, an indolocarbazole, an anthracyline, a macrolide, a peptide or, an alkaloid, including a 3-alkylpyridine alkaloid, and the reducing sugar is of the formula:

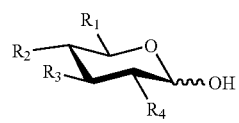

where $R_1$, $R_2$, $R_3$, and $R_4$ are independently selected from —H, —OH, —N₃, —NH₂, —CH₃, —CH₂OH, —CN₃, —CH₂NH, —CH₂SH, —CNH₂, —CH₂N₃, —COOH, —COCH₃, —CXH₂, —CX₂H, and where X is Cl, Br, F, or I. Further, the aglycon is preferably of the formula

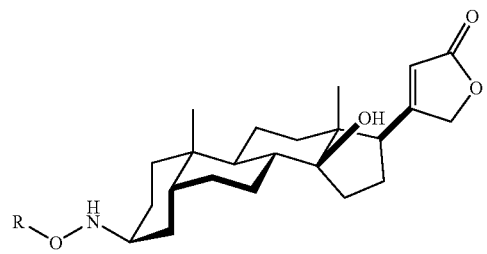

where R is —CH$_3$, —CH$_2$CH$_3$, —CH(CH$_3$)$_2$, —C(CH$_3$)$_3$, allyl, benzyl, —CH$_2$CH$_2$CH$_3$, —CH(CH$_3$)CH$_2$CH$_3$, cyclopentyl or cyclohexyl.

DESCRIPTION OF THE PREFERRED EMBODIMENTS

Figure 1A:
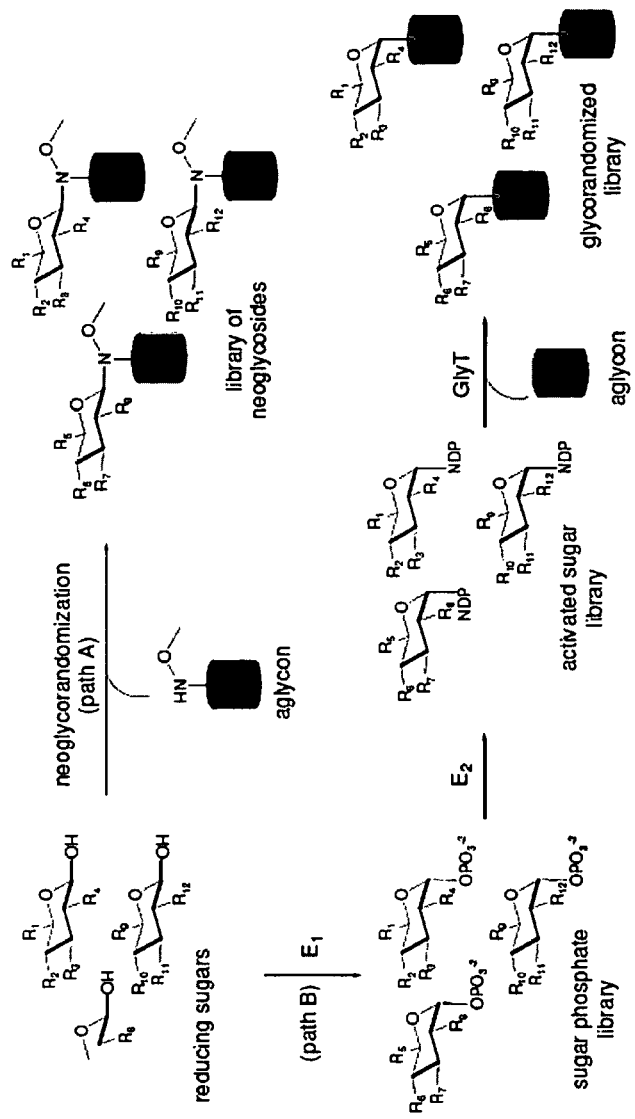
FIG. 1A is a schematic illustration of the method of neoglycorandomization of the present invention that involves the chemoselective formation of glycosidic bonds between reducing sugars and a secondary alkoxyamine to form a library of neoglycosides compared to chemoenzymatic glycorandomization. Neoglycorandomization ("path A") is only limited by the ease of installation of the reactive secondary alkoxyamine group onto a complex natural product aglycon. In contrast, chemoenzymatic glycorandomization ("path B") uses nucleotide sugar activation enzymes ("E$_1$" and "E$_2$") and glycosyltransferase enzymes ("GlyT") that display natural or engineered promiscuity to glycosylate secondary metabolites, and is thus limited to natural products for which promiscuous glycosylation machinery is available.

Glycosylated natural products are reliable platforms for the development of many front-line drugs, yet our understanding of the relationship between attached sugars and biological activity is limited by the availability of convenient glycosylation methods. Glycorandomization is a tool used to convert a single aglycon molecule into a library of analogs with a diverse array of sugar attachments.

Unless otherwise stated, the following terms used in this application, including the specification and claims, have the definitions given below. As used in the specification and the appended claims, the singular forms "a," "an" and "the" include plural referents unless the context clearly dictates otherwise.

"Subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable carrier" as used herein means a chemical composition with which a biologically active ingredient can be combined and which, following the combination, can be used to administer the active ingredient to a subject.

A "pharmaceutically acceptable" ester or salt as used herein means an ester or salt form of the active ingredient which is compatible with any other ingredients of the pharmaceutical composition and which is not deleterious to the subject to which the composition is to be administered. The terms "pharmaceutically acceptable salts" or "pro-drugs" includes the salts and prodrugs of compounds that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible, of the compounds.

"Pro-drug" means a pharmacologically inactive form of a compound which must be metabolized in vivo by a subject after administration into a pharmacologically active form of the compound in order to produce the desired pharmacological effect. After administration to the subject, the pharmacologically inactive form of the compound is converted in vivo under the influence of biological fluids or enzymes into a pharmacologically active form of the compound. Although metabolism occurs for many compounds primarily in the liver, almost all other tissues and organs, especially the lung, are able to carry out varying degrees of metabolism. For example, metabolism of the pro-drug may take place by hydrolysis in blood. Pro-drug forms of compounds may be utilized, for example, to improve bioavailability, mask unpleasant characteristics such as bitter taste, alter solubility for intravenous use, or to provide site-specific delivery of the compound. Reference to a compound herein includes pro-drug forms of a compound.

A discussion of the use of pro-drugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987. For example, if a compound contains a carboxylic acid functional group, a pro-drug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from five to ten carbon atoms, alkoxycarbonyloxymethyl having from three to six carbon atoms, 1-(alkoxycarbonyloxy)ethyl having from four to seven carbon atoms, 1-methyl-1-(alkoxycarbonyloxy) ethyl having from five to eight carbon atoms, N-(alkoxycarbonyl)aminomethyl having from three to nine carbon atoms, 1-(N-(alkoxycarbonyl)amino)ethyl having from four to ten carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound comprises an alcohol functional group, a pro-drug can be formed by the replacement of the hydrogen atom of the alcohol group with a group such as $(C_1-C_6)$alkanoyloxymethyl, 1-$(C_1-C_6)$alkanoyloxy)ethyl, 1-methyl-1-$(C_1-C_6)$alkan-oyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and alpha-aminoacyl, or alpha-aminoacyl-alpha-aminoacyl, where each alpha-aminoacyl group is independently selected from the naturally occurring L-amino acids, P(O)(OH)$_2$, —P(O)(O$(C_1-C_6)$alkyl)$_2$ or glycosyl (the radical resulting from the removal of a hydroxyl group of the hemiacetal form of a carbohydrate).

If a compound comprises an amine functional group, a pro-drug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural alpha-aminoacyl or natural alpha-aminoacyl-, —C(OH)C(O)OY wherein Y is H, $(C_1-C_6)$alkyl or benzyl, —C(OY$_0$)Y$_1$ wherein Y$_0$ is $(C_1-C_4)$ alkyl and Y$_1$ is ($(C_1-C_6)$alkyl, carboxy$(C_1-C_6)$alkyl, amino$(C_1-C_4)$alkyl or mono-N— or di-N,N—$(C_1-C_6)$alkylaminoalkyl, —C(Y$_2$)Y$_3$ wherein Y$_2$ is H or methyl and Y$_3$ is mono-N— or di-N,N—$(C_1-C_6)$-alkylamino, morpholino, piperidin-1-yl or pyrrolidin-1-yl.

The term "salts" refers to inorganic and organic salts of compounds. These salts can be prepared in situ during the final isolation and purification of a compound, or by separately reacting a purified compound with a suitable organic or inorganic acid or base, as appropriate, and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, besylate, esylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Compounds having N-oxides of amino groups, such as produced by reaction with hydrogen peroxide, are also encompassed.

The term "steroid" refers to a terpenoid lipid characterized by a carbon skeleton with four fused rings, arranged in a 6C-6C-6C-5C fashion. The term "non-digoxygenin steroid" refers to a steroid wherein the fused five-carbon ring is not covalently bonded to a nonfused cyclic ester containing four carbon atoms.

A "therapeutically effective amount" means an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors.

For purposes of the present invention, "treating" or "treatment" describes the management and care of a patient for the purpose of combating the disease, condition, or disorder. The terms embrace both preventative, i.e., prophylactic, and palliative treatment. Treating includes the administration of a compound of present invention to prevent the onset of the symptoms or complications, alleviating the symptoms or complications, or eliminating the disease, condition, or disorder.

The form in which the active compound is administered to the cell is not critical; the active compound need only reach the cell, directly or indirectly. The invention encompasses preparation and use of medicaments and pharmaceutical compositions comprising a compound described herein as an active ingredient. A neoglycoside is administered to a patient in a therapeutically effective amount. A neoglycoside can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. It is also noted that the dose of the compound can be varied over time. A neoglycoside can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a patient or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 100 milligrams to about two grams of the active ingredient, and preferably comprises from about 200 milligrams to about 1.0 gram of the active ingredient.

In addition, a neoglycoside can be administered alone, in combination with other neoglycosides, or with other pharmaceutically active compounds. The other pharmaceutically active compounds can be selected to treat the same disease as the neoglycoside or a different disease. If the patient is to receive or is receiving multiple pharmaceutically active compounds, the compounds can be administered simultaneously or sequentially in any order. For example, in the case of tablets, the active compounds may be found in one tablet or in separate tablets, which can be administered at once or sequentially in any order. In addition, it should be recognized that the compositions can be different forms. For example, one or more compounds may be delivered via a tablet, while another is administered via injection or orally as a syrup.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. The kit can further comprise an instructional material as described herein. For example, a kit may comprise two separate pharmaceutical compositions comprising respectively a first composition comprising a neoglycoside or a neoglycoside agonist and a pharmaceutically acceptable carrier; and composition comprising second pharmaceutically active compound and a pharmaceutically acceptable carrier. The kit also comprises a container for the separate compositions, such as a divided bottle or a divided foil packet. Additional examples of containers include syringes, boxes, bags, and the like. Typically, a kit comprises directions for the administration of the separate components.

The kit form is particularly advantageous when the separate components are preferably administered in different dosage forms (e.g., oral and parenteral), are administered at different dosage intervals, or when titration of the individual components of the combination is desired by the prescribing physician.

An example of a kit is a blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and a sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day. Also, a daily dose of a neoglycoside composition can consist of one tablet or capsule, while a daily dose of the second compound can consist of several tablets or capsules and vice versa. The memory aid should reflect this and assist in correct administration.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

A neoglycoside composition, optionally comprising other pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. Other contemplated formulations include projected nanoparticles, liposomal preparations, resealed erythrocytes containing the active ingredient, and immunologically-based formulations.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques.

Compositions suitable for parenteral injection comprise the active ingredient combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

These compositions may also contain adjuvants such as preserving, wetting, emulsifying, and/or dispersing agents. Preventing microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Dosage forms can include solid or injectable implants or depots. In preferred embodiments, the implant comprises an effective amount of an active agent selected from the group consisting of a neoglycoside, a neoglycoside agonist and a neoglycoside antagonist and a biodegradable polymer. In preferred embodiments, a suitable biodegradable polymer can be selected from the group consisting of a polyaspartate, polyglutamate, poly(L-lactide), a poly(D,L-lactide), a poly(lactide-co-glycolide), a poly(ε-caprolactone), a polyanhydride, a poly(beta-hydroxy butyrate), a poly(ortho ester) and a polyphosphazene. In other embodiments, the implant comprises an effective amount of active agent and a silastic polymer. The implant provides the release of an effective amount of active agent for an extended period of about one week to several years.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pregelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin; Such soft capsules comprise the active ingredient, which can be mixed with water or an oil medium such as peanut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., Aliment. Pharmacol. Therap. (1987) 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663, 308), glycosides (Friend et al., J. Med. Chem. (1984) 27:261-268) and a variety of naturally available and modified polysaccharides (see PCT application PCT/GB89/00581) can be used in such formulations.

Pulsed release technology such as that described in U.S. Pat. No. 4,777,049 can also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfuryl alcohol, polyethylene glycols, fatty acid esters of sorbitan, or mixtures of these substances, and the like. Besides such inert diluents, the composition can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxyated isostearyl alcohols, polyoxyethylene sorbitol or sorbitan esters, microcrystalline cellulose, hydrogenated edible fats, sodium alginate, polyvinylpyrrolidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene, sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

In other embodiments, the pharmaceutical composition can be prepared as a nutraceutical, i.e., in the form of, or added to, a food (e.g., a processed item intended for direct consumption) or a foodstuff (e.g., an edible ingredient intended for incorporation into a food prior to ingestion). Examples of suitable foods include candies such as lollipops, baked goods such as crackers, breads, cookies, and snack cakes, whole, pureed, or mashed fruits and vegetables, beverages, and processed meat products. Examples of suitable foodstuffs include milled grains and sugars, spices and other seasonings, and syrups. The polypeptide compositions described herein are preferably not exposed to high cooking temperatures for extended periods of time, in order to minimize degradation of the compounds.

Compositions for rectal or vaginal administration can be prepared by mixing a neoglycoside and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the neoglycoside. Such a composition can be in the form of, for example, a suppository, a retention enema preparation, and a solution for rectal or colonic irrigation. Suppository formulations can further comprise various additional ingredients including antioxidants and preservatives. Retention enema preparations or solutions for rectal or colonic irrigation can be made by combining the active ingredient with a pharmaceutically acceptable liquid carrier. As is known in the art, enema preparations can be administered using, and can be packaged within, a delivery device adapted to the rectal anatomy of a human. Enema preparations can further comprise various additional ingredients including antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Dosage forms for topical administration of a neoglycoside include ointments, powders, sprays and inhalants. The compounds are admixed under sterile conditions with a physiologically acceptable carrier, and any preservatives, buffers, and/or propellants that may be required. Formulations suitable for topical administration include liquid or semi-liquid preparations such as liniments, lotions, oil-in-water or water-in-oil emulsions such as creams, ointments or pastes, and solutions or suspensions. Topically-administrable formulations can, for example, comprise from about 0.1% to about 10% (w/w) active ingredient, although the concentration of the active ingredient can be as high as the solubility limit of the active ingredient in the solvent. Formulations for topical administration can further comprise one or more of the additional ingredients described herein.

Ophthalmic formulations, eye ointments, powders, and solutions are also contemplated as being within the scope of this invention. Such formulations can, for example, be in the form of eye drops including, for example, a 0.1-1.0% (w/w) solution or suspension of the active ingredient in an aqueous or oily liquid carrier. Such drops can further comprise buffering agents, salts, or one or more other of the additional ingredients described herein. In other embodiments, ophthalmically administrable formulations comprise the active ingredient in microcrystalline form or in a liposomal preparation.

A pharmaceutical composition of the invention can be prepared, packaged, or sold in a formulation suitable for pulmonary administration via the buccal cavity. Such a formulation can comprise dry particles which comprise the active ingredient and which have a diameter in the range from about 0.5 to about 7 nanometers, and preferably from about one to about six nanometers. Such compositions are conveniently in the form of dry powders for administration using a device comprising a dry powder reservoir to which a stream of propellant can be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than seven nanometers. More preferably, at least 95% of the particles by weight have a diameter greater than one nanometer and at least 90% of the particles by number have a diameter less than six nanometers. Dry powder compositions preferably include a solid fine powder diluent such as sugar and are conveniently provided in a unit dose form.

Low boiling propellants generally include liquid propellants having a boiling point below 65 degrees F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery can also provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares. Formulations suitable for nasal administration can, for example, comprise from about as little as 0.1% (w/w) and as much as 100% (w/w) of the active ingredient, and can further comprise one or more of the additional ingredients described herein.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and can further comprise one or more of the additional ingredients described herein.

For parenteral administration in non-human animals, the compound or compounds may be prepared in the form of a paste or a pellet and administered as an implant, usually under the skin of the head or ear of the animal. Paste formulations can be prepared by dispersing a compound or compounds in pharmaceutically acceptable oil such as peanut oil, sesame oil, corn oil or the like. Pellets containing a therapeutically effective amount of a compound or compounds can be prepared by admixing the compound with a diluent such as a carbowax, carnauba wax, and the like, and a lubricant, such as magnesium or calcium stearate, can be added to improve the pelleting process. It is, of course, recognized that more than one pellet may be administered to an animal to achieve the desired dose level. Moreover, it has been found that such implants may also be administered periodically during the animal treatment period in order to maintain the proper active agent level in the animal's body.

The neoglycoside of the present invention, the stereoisomers and prodrugs thereof, and the pharmaceutically acceptable salts of the peptides, stereoisomers, and prodrugs, can be administered to a patient at dosage levels in the range of from about 0.01 to about 1,000 mg per day. For a normal adult human having a body weight of about 70 kg, a dosage in the range of from about 0.01 to about 300 mg is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

It is not critical whether the compound is administered directly to the cell, to a tissue comprising the cell, a body fluid that contacts the cell, or a body location from which the compound can diffuse or be transported to the cell. It is sufficient that the compound is administered to the patient in an amount and by a route whereby an amount of the compound sufficient to mobilize lipids in the cell arrives, directly or indirectly at the cell. The minimum amount varies with the identity of the neoglycoside. In some embodiments, the minimum amount is generally in the range from $10^{-9}$ to $10^{-5}$ molar. In other embodiments, the minimum amount is typically in the range from $10^{-7}$ to $10^{-5}$ molar.

In preferred embodiments, a pharmaceutical composition comprising a neoglycoside can be administered to a patient at dosage levels in the range of about 0.1 to about 7,000 mg per day. A preferred dosage range is about 1 to about 100 mg per day. In other embodiments, a pharmaceutical composition comprising a neoglycoside can be administered to deliver a dose of between one nanogram per day per kilogram body weight and 100 milligrams per day per kilogram body weight, preferably from about 0.1 to about 10 mg/kg body weight of the individual per day, and preferably to deliver of between 100 milligrams and 2 grams, to a human patient.

The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ordinary skill of one in the art in view of this disclosure. It is understood that the ordinarily skilled physician or veterinarian will readily determine and prescribe an effective amount of the compound to mobilize lipid stores, induce weight loss, or inhibit appetite in the patient. In so proceeding, the physician or veterinarian can, for example, prescribe a relatively low dose at first, subsequently increasing the dose until an appropriate response is obtained. It is further understood, however, that the specific dose level for any particular human will depend upon a variety of factors including the activity of the specific compound employed, the age, body weight, general health, gender, and diet of the human, the time of administration, the route of administration, the rate of excretion, any drug combination, and the severity of any disorder being treated.

In some embodiments, a neoglycoside of the present invention, a stereoisomer or prodrug thereof, or a pharmaceutically acceptable salt of the stereoisomer or prodrug; is administered to a subject in need of treatment therewith, preferably in the form of a pharmaceutical composition. It is generally preferred that such administration be oral or pulmonary. However, if the subject being treated is unable to swallow, or oral administration is otherwise impaired or undesirable, parenteral or transdermal administration will be appropriate.

Chemoselective ligation reactions are means for expanding natural product sugar diversity. This approach is particularly attractive to complex natural products as chemoselective ligation offer advantages similar to those of enzymatic reactions (efficiency, regio- and stereospecificity), with the advantage of a much broader range of coupling partners. See Hang, H. C. et al., Acc. Chem. Res. (2001) 34, 727-736; Kolb, H. C. et al., Angew. Chem. Int. Ed. (2001) 40, 2004-2021; Langenhan, J. M. et al., Curr. Org. Syn. (2005) 2, 59-81.

In the context of sugars (e.g. an aldose, 127, see below), one well known reaction is that between a free aldose and an aminooxy functionalized molecule to specifically provide the sugar oxime without the requirement of protecting groups or anomeric activation. This reaction, when using a reacting unit bearing a 'primary'—O—NH$_2$ group, leads to the open-chain sugar oxime. However, it was recently reported that the cyclic form of the sugar is restored when a 'secondary' hydroxylamino group (R—O—NH—R') is used (e.g. 128 to 130). See Langenhan, J. M. et al., Chem. Comm. (2004) 623. This strategy has been employed in coupling simple sugars to peptides (termed 'neoglycopeptides'). See Peri, F. et al., Tetrahedron (1998) 54, 12269; Carrasco, M. R. et. al., Tetrahedron Lett. (2002) 43, 5727; Carrasco, M. R. et. al., J. Org. Chem. 2003, 68, 195; Carrasco, M. R. et al., J. Org. Chem. (2003) 68, 8853. More recently, the approach has been used to generate a small set of di- and trisaccharides (termed 'neoglycosides'). Peri, F. et. al., Chem. Comm. (2002) 1504; Peri, F. et al., Chem. Comm. (2004) 623.

In examples using Glc or GlcNAc as the sugar donors, the product was found to favor the β-neogycoside (α:β=7:1) and characterization/modeling via NMR spectroscopy, ab initio, molecular mechanics and molecular dynamics methods revealed the neoglycosides to exhibit only slight conformational distortion in comparison to the corresponding O-glycosides (Peri, F. et. al., Chem. Eur. J. (2004) 10, 1433).

Scheme 1

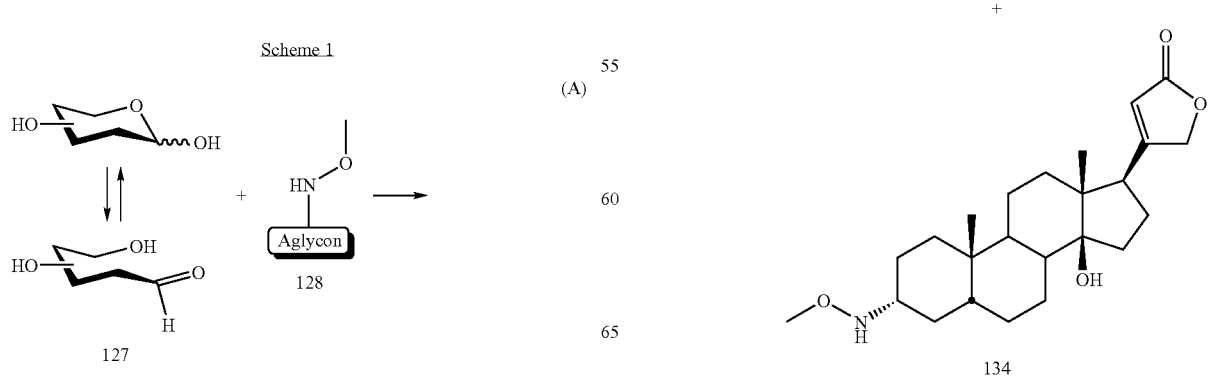

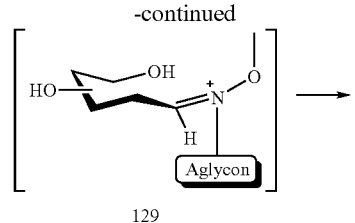

129

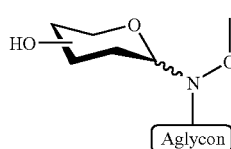

130

(B)

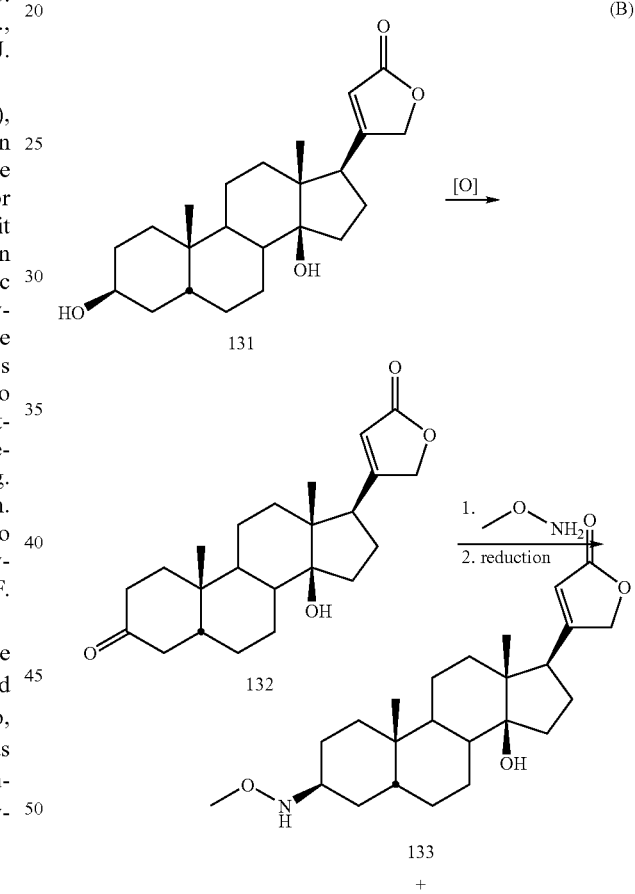

Digitoxin Neoglycorandomization. To assess the application of this strategy toward natural product 'neoglycorandomization' (the term based upon an extension of existing nomenclature), the simple model natural product aglycon digitoxigenin was selected. Digitalis (mainly digitoxin and digoxin, extracts from *Digitalis purpurea* and *Digitalis lanata* used clinically, respectively) has been used as a cardiac drug for more than 200 years. The cardiac glycosides contain a steroid nucleus and unsaturated lactone (together referred to as the aglycon) substituted with a carbohydrate(s)—the general role of the latter of which is attributed primarily to absorption and pharmacokinetics. In addition, digitalis is known to block cell proliferation, induce apoptosis in different malignant cell lines, signal through the pathways of epidermal growth factor receptor (EGFR), and these compelling links to anticancer activities can, in part, be modulated by saccharide substitutions.

Commercially available digitoxigenin 131 was converted to ketone 132, as shown above (81% yield) using Jones oxidation (reaction conditions: 0.742 mmol 131, 31 mL acetone, cool to 0° C., Jones agent added dropwise until orange color persisted, quenched with MeOH after 20 min).[234] Ketone 132 was subsequently reacted with methoxyamine in the presence of pyridine in methanolic solution to afford a mixture of E and Z oximes in quantitative yield (reaction conditions: 0.219 mmol 132 dissolved in 0.5 mL MeOH, 2.2. eq. pyridine, then MeONH$_2$HCl added, 30 min).[235] A variety of reducing agents were examined for oxime reduction, including K-selectride, NaBH$_3$CN, pyridine-borane complex and t-butylamine-borane complex, with the latter providing the desired methoxyamines 133 and 134 in the desired quantitative production of a 50:50 ratio (reaction conditions: 0.159 mm oxime suspended in 0.23 mL EtOH, 1 mL dioxane, cooled to 0° C., added 3.3. eq. borane complex, then 0.43 mL 10% aq. HCl solution, 1 hr). Diastereomers 133 and 134 were easily separated using standard chromatography (EtOAc:hexane 3:2 followed by 100% EtOAc for the second product). As a test for neoglycorandomization, methoxyamine 133 was subsequently reacted with sugars 27-58, as shown below, (0.1 mmol 133, 2 eq. aldose, DMSO, 50° C., 12 hr) to provide >70% product yield for 25 of the 31 sugars examined based upon LC-MS.[236] Of the 31 cardiac glycoside variants generated in this proof of concept demonstration, those deriving from 38, 39 and 52 present the opportunity for further diversification via Huisgen 1,3-dipolar cycloaddition, while those deriving from 34, 41 and 48 present handles for rapid alkylation.

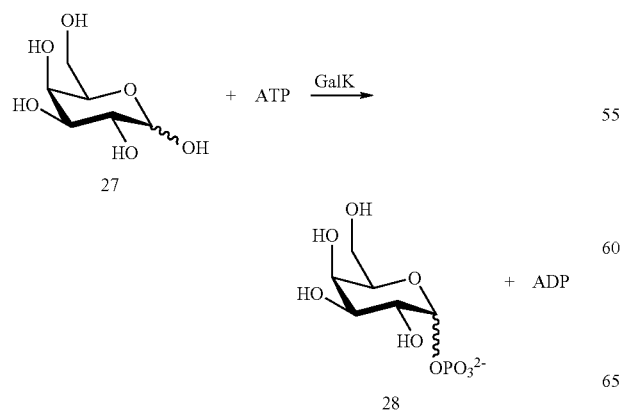

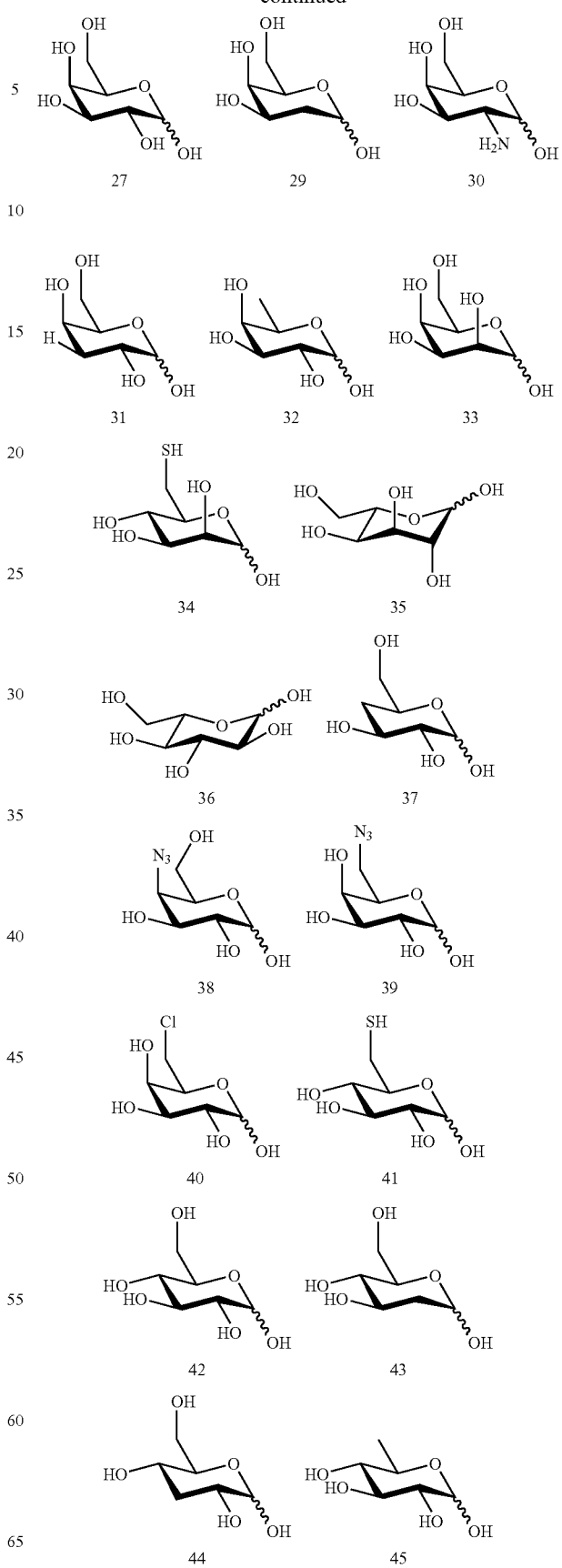

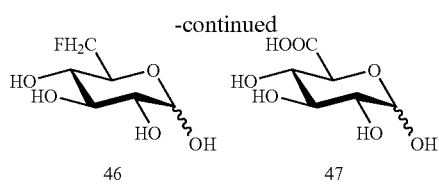
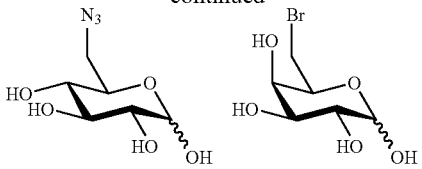
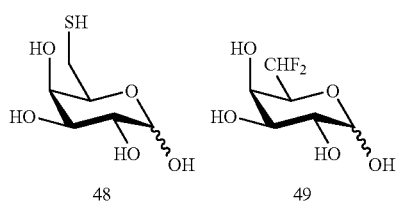
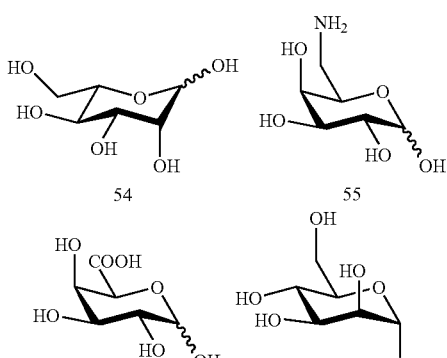
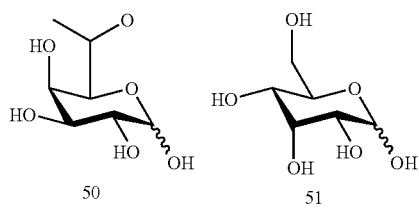
For example, the simple structure of digitoxin allows the easy installation of a reactive chemical handle, as shown below:
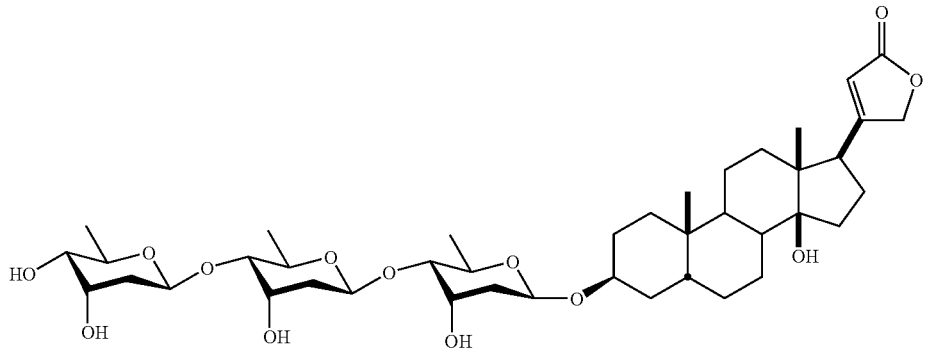

Studies have suggested that digitoxin and/or carbohydrate-altered digitoxin derivatives may display anti-cancer activities (Haux, J. Med. Hypotheses (2002) 59, 781; Stenkvist, B. Anti-Cancer Drugs (2002) 12, 635). In order to obtain these digitoxin derivatives, chemoselective ligation is done using methoxyamino group. The methoxyamino groups are reacted with free sugars to form closed-ring neoglycosides (unlike R—ONH$_2$ groups which form predominately open-chain sugar oximes). The ligations are high yielding and often stereoselective.

Scheme 3

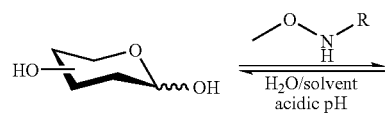

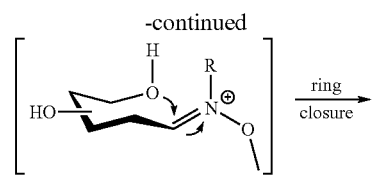

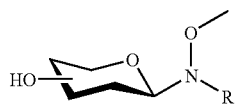

Installation of methoxyamino group occurs quantitatively. Isomers may be assigned via x-ray crystallography. The one-step digitoxin to digitoxigenone conversion (step 1) as shown below:

Scheme 4

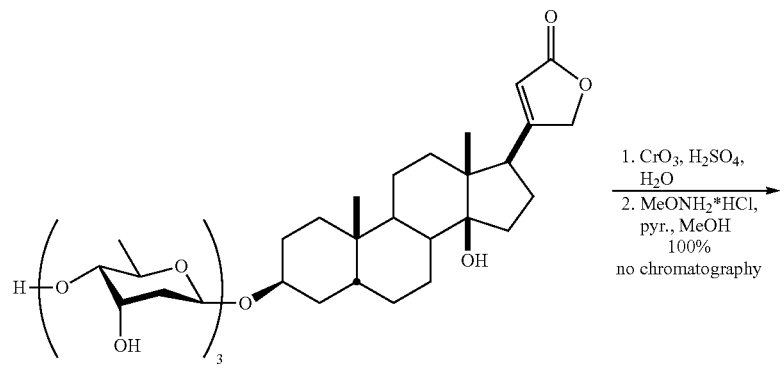

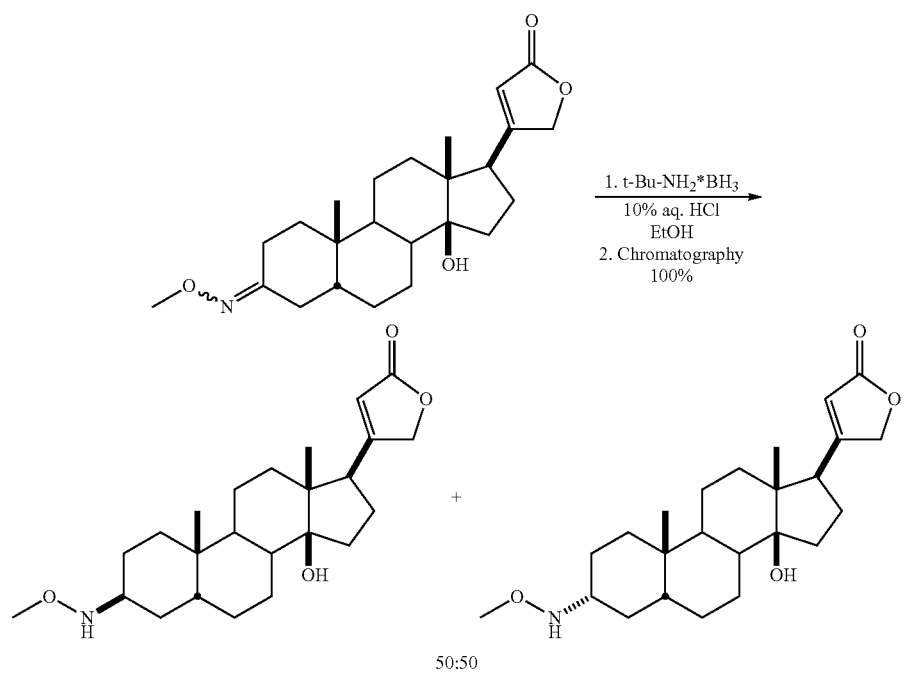

The effect of different ligation conditions were evaluated for D-glucose as shown below:

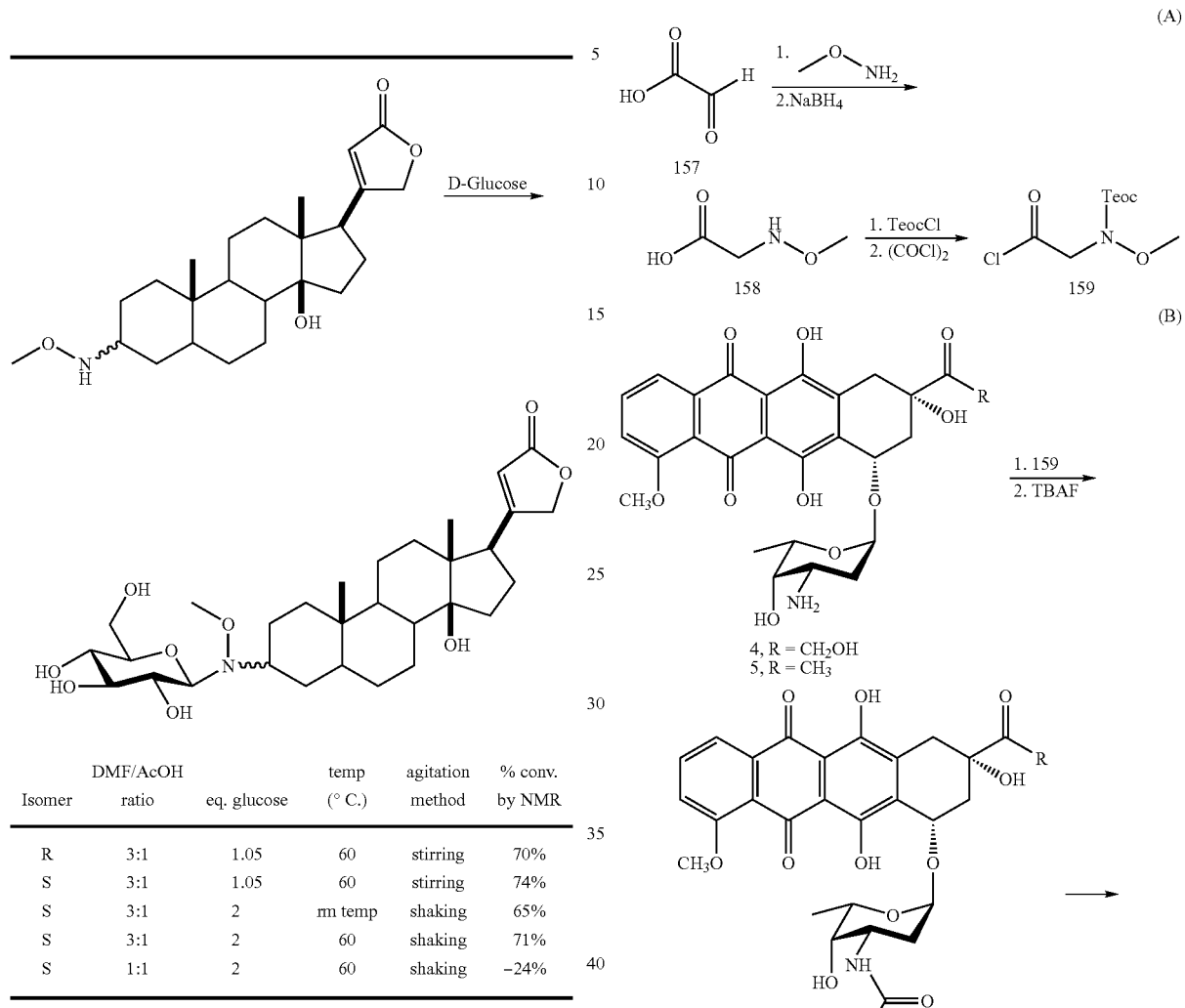

| Isomer | DMF/AcOH ratio | eq. glucose | temp (° C.) | agitation method | % conv. by NMR |
|---|---|---|---|---|---|
| R | 3:1 | 1.05 | 60 | stirring | 70% |
| S | 3:1 | 1.05 | 60 | stirring | 74% |
| S | 3:1 | 2 | rm temp | shaking | 65% |
| S | 3:1 | 2 | 60 | shaking | 71% |
| S | 1:1 | 2 | 60 | shaking | ~24% |

Neoglycorandomization Strategies—Amine Modification (Indolocarbazoles and Anthracyclines). As an expansion of neoglycorandomization, a second complimentary handle was installed to target amines within natural products. Specifically, amine-handle 159, as shown below was synthesized as shown below and used to acylate the daunosamine sugar within 4 and 5 as well as the indole nitrogen(s) in various indolocarbazole aglycons (e.g. exemplified by the staurosporine aglycon 161). Literature precedent exists for acylation of both daunosamine (Ingallinella, P. et. al., Bioorg. Med. Chem. Lett. (2001) 11, 1343-1346 and indolocarbazole nitrogens[16] with diacylation, in some cases of the latter, observed in the presence of excess acylating agent. The predicted outcome for this approach is identical to that described for carbonyl installation with the exception that the parent methoxyamino-installed natural product (e.g. 160 and 162) consists as a single species (versus diastereomers from oxime reduction). Thus, initial library size is estimated at approximately 150 derivatives for each indolocarbazole and anthracycline input.

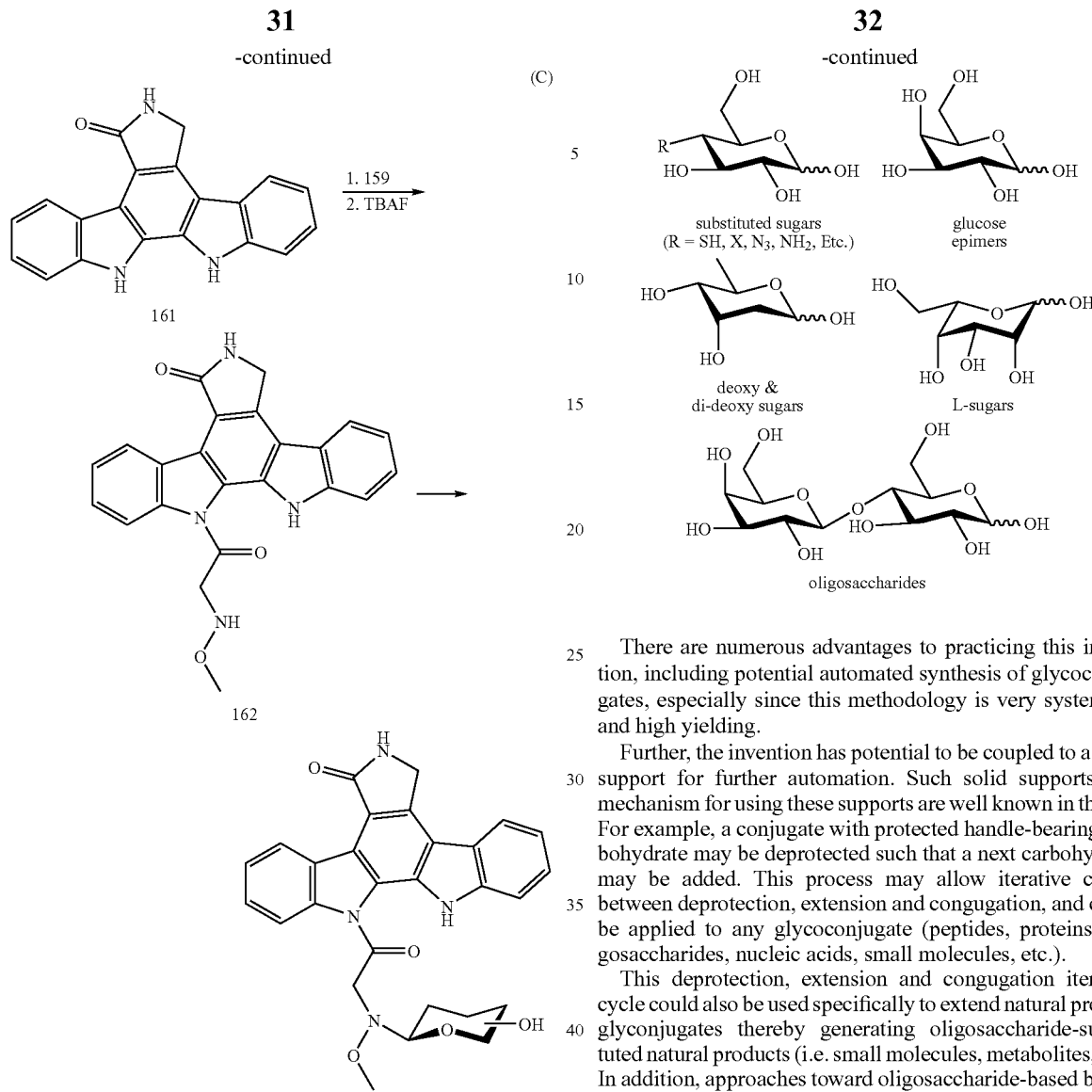

The methoxyamino-aglycon may be reacted with a collection of commercially available and synthetic reducing saccharides. (See below) Some of these sugars may contain orthogonal chemoselective ligation handles allowing further diversification. Such reactions may be run and purified in parallel.

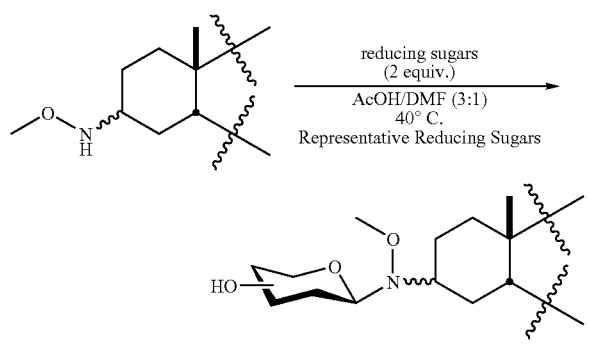

There are numerous advantages to practicing this invention, including potential automated synthesis of glycoconjugates, especially since this methodology is very systematic and high yielding.

Further, the invention has potential to be coupled to a solid support for further automation. Such solid supports and mechanism for using these supports are well known in the art. For example, a conjugate with protected handle-bearing carbohydrate may be deprotected such that a next carbohydrate may be added. This process may allow iterative cycles between deprotection, extension and congugation, and could be applied to any glycoconjugate (peptides, proteins, oligosaccharides, nucleic acids, small molecules, etc.).

This deprotection, extension and congugation iterative cycle could also be used specifically to extend natural product glyconjugates thereby generating oligosaccharide-substituted natural products (i.e. small molecules, metabolites, etc). In addition, approaches toward oligosaccharide-based bioactive secondary metabolites (i.e. natural products, small molecules) would benefit by this chemistry—notably, aminoglycosides, orthosomycins (evernimicin, avilamycin) and saccharomicins as representative examples.

Further, since this chemistry is amenable to certain physiological conditions (e.g. acidic tissues and/or cellular locales) 'scavenging' of carbohydrates in vivo may be possible. In placing the handle upon an appropriate carrier aglycon (i.e. natural product, metabolite, small molecule), one of ordinary skill in the art can potentially selectively starve certain cells of energy.

The chemistry is not limited to only the digitoxin, indolocarbazole or anthracycline compounds—all carbonyls, amines and potentially hydroxyls are accessible, and contemplated to be within the scope of the present invention. Furthermore, this chemistry is not only limited to those carbohydrates explicitly shown herein but any reducing sugar. Especially given the selectivity towards reducing sugars, this chemistry is amenable to assaying reducing sugar concentrations and therefore, amenable to assaying any sugar-utilizing enzyme/system in which reducing sugar concentrations change.

In an effort to explore the contribution of the sugar constituents of pharmaceutically relevant glycosylated natural products, chemoenzymatic "glycorandomization" methods have been developed (FIG. 1A, path B) to rapidly convert a single aglycon structure into a library of analogs with a broad array of sugar attachments. Despite these advances, chemoenzymatic glycorandomization currently excludes a number of essential glycoconjugates since it is limited to natural products for which promiscuous glycosyltransferases are available and can operate in vitro. This complementary robust chemical approach—referred to as "neoglycorandomization"—accomplishes a one step sugar ligation which does not require any prior sugar protection or activation (FIG. 1A, path A). Using digitoxin as a simple pharmaceutically-relevant model, neoglycorandomization leads to the discovery of digitoxin analogs that are much more potent and/or tumor-specific cytotoxins, but less potent $Na^+/K^+$-ATPase inhibitors, relative to the parent natural product. Thus, neoglycosylation is useful as a general tool for glycobiology and drug discovery. The studies also highlight a potentially divergent relationship between $Na^+/K^+$-ATPase inhibition and cytotoxicity of cardiac glycosides.

Figure 1B:
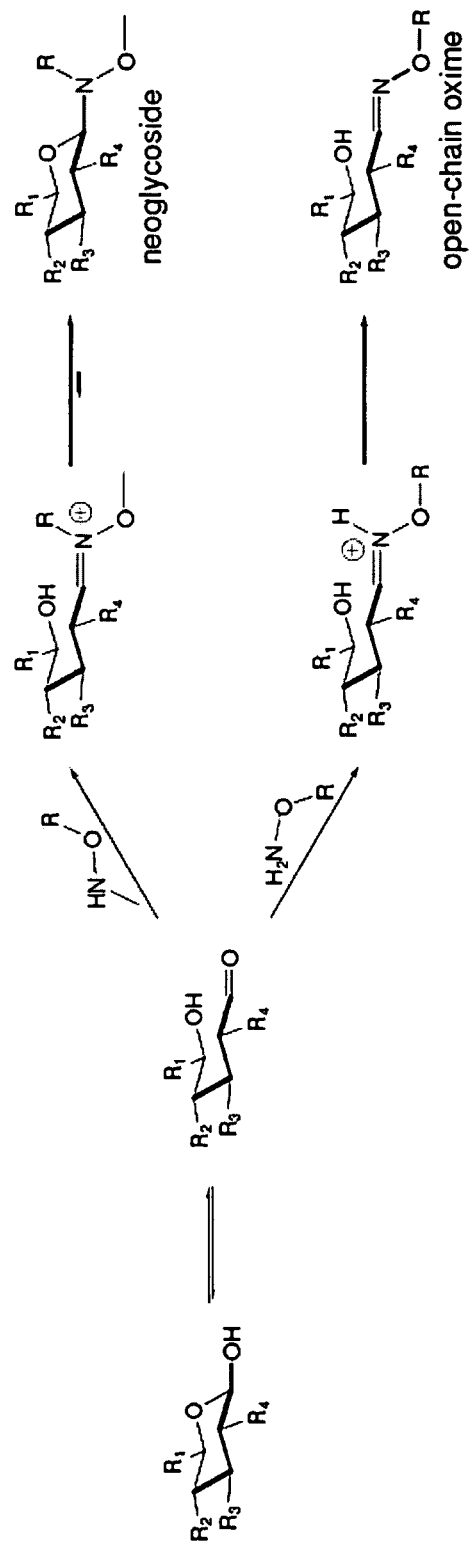
FIG. 1B is a schematic illustration showing that secondary alkoxyamines react to form closed-ring neoglycosides while primary alkoxyamines react with reducing sugars to form open-chain oximes.

Neoglycorandomization is based upon the chemoselective formation of glycosidic bonds between reducing sugars and a secondary alkoxyamine-containing aglycon to form "neoglycosides" (FIG. 1A, path A). The notable advantage of this approach is, unlike most traditional chemical glycosylation reactions, unprotected and non-activated reducing sugars are used as sugar donors in the reaction under mild conditions (Van Vranken, D. L. et al., J. Org. Chem. (2000) 65, 7541-7553). In early examples of this chemoselective reaction, sugars and peptides that contain secondary alkoxyamines were reacted with D-glucose, D-mannose, D-galactose, lactose, and D-N-acetylglucosamine to generate oligosaccharide and glycopeptide mimics, respectively (Peri, F. et al., Chem. Comm. (2002) 1504-1505; Carrasco, M. R. et al. J. Org. Chem. (2003) 68, 8853-8858). These pioneering studies revealed that, unlike primary alkoxyamines which provide open-chain oxime isomers (Cervigni, S. E. et al., Angew. Chem. Int. Ed. (1996) 35, 1230-1232), secondary alkoxyamines react to form closed-ring neoglycosides (FIG. 1B). Although the stability of these model neoglycosides was not examined, the distribution of pyranose, and occasionally furanose, anomers in neoglycosides was found to be dependant on the identity of the sugar (Peri, F. et al., Tetrahedron (1998) 54, 12269-12278) and, equilibration between the product isomers is sometimes observed. Closed-ring neoglycosides were found to display conformational behavior similar to natural O-glycosides by NMR studies, molecular dynamics simulations, and ab initio calculations (Peri, F. et al., Chem. Eur. J. (2004) 10, 1433-1444).

Aglycon Synthesis. Compounds 2a,b, 3β, and 3α were synthesized according to procedures described below.

Digitoxigenone oximes (2a,b). Jones reagent was prepared by mixing $CrO_3$ (62.4 g), $H_2SO_4$ (55.2 mL), and water (170 mL). This reagent was slowly added to an Erlynmeyer flask containing digitoxin (29.67 g, 38.8 mmol) suspended in acetone (1300 mL) at 0° C. The resulting mixture was mechanically stirred for 3 h at rm temp. The mixture was then cooled to 0° C., quenched with ~100 mL MeOH, stirred for 20 min, and 100 mL water was added. Volatile solvents were removed under reduced pressure, and the aqueous mixture was extracted with chloroform (4×200 mL). The combined organic layers were washed with sat. aq. $NaHCO_3$, 2 times with water, dried over $Na_2SO_4$, filtered, then concentrated. The product ketone digitoxigenone (9.48 g, 66% yield), obtained as a white foam (TLC $R_f$=0.23 in 3:2 EtOAc/hexane), was used without further purification. $^1$H NMR ($CDCl_3$, 400 MHz) δ 5.89 (s, 1H), 5.03 (A of ABX, 1H, J=18.2, 1.5), 4.94 (B of ABX, 1H, J=18.2, 1.7), 2.82 (m, 1H), 2.65 (dd, 1H, J=14.5), 2.37 (td, 1H, J=14.8, 5.4), 2.17 (m, 4H), 2.04 (m, 2H), 1.96-1.73 (m, 6H), 1.67 (m, 1H), 1.61-1.23 (m, 7H), 1.02 (s, 3H), 0.92 (s, 3H); $^{13}$C NMR ($CDCl_3$, 100 MHz): δ 12.9, 175.0, 174.7, 117.5, 85.0, 77.4, 73.6, 50.8, 49.7, 43.7, 42.1, 41.4, 39.7, 37.1, 36.7, 36.5, 35.2, 33.0, 26.9, 26.5, 22.5, 21.2, 20.9, 15.8; Electrospray ionization-MS m/z (M+H) calculated for $C_{23}H_{33}O_4$ 373.5, observed 373.2. Digitoxigenone (9.48 g, 25.5 mmol) was dissolved in methanol (57 mL) and pyridine (4.5 mL, 55.9 mmol). Methoxyamine hydrochloride (3.40 g, 0.7 mmol) was added, and the solution was stirred for 30 min then concentrated. The resulting residue was dissolved in $CH_2Cl_2$ and washed with 1 M HCl, brine, dried over $MgSO_4$, filtered, and then concentrated. The desired mixture of oxime diastereomers 2a,b (TLC $R_f$=0.49 and 0.39 in 3:2 EtOAc/hexane), obtained as a white crust (9.30 g, 91% yield), was used without further purification. $^1$H NMR ($CDCl_3$, 400 MHz) δ 5.88 (br t, 1H), 5.03-4.90 (m, 1H), 4.85-4.80 (m, 1H), 3.82 (s, 1.3H), 3.81 (s, 1.7H), 3.01 (br d, 0.6H, J=14.9), 2.87-2.77 (m, 1.5H), 2.45 (t, 0.6H, J=13.9), 2.19-1.11 (m, 23H); $^{13}$C NMR ($CDCl_3$, 100 MHz): δ 174.8, 174.7, 160.4, 60.3, 117.7, 85.4, 77.4, 73.6, 61.1, 50.9, 49.7, 43.5, 41.8, 41.7, 39.9, 36.8, 36.5, 36.2, 35.8, 35.7, 35.6, 33.1, 32.0, 27.0, 26.9, 26.5, 25.6, 23.0, 22.9, 21.2, 21.1, 20.5, 15.8; Electrospray ionization-MS m/z (M+H) calculated for $C_{24}H_{36}NO_4$ 402.5, observed 402.3.

Aglycons 3β and 3α. Oximes 2a,b (539 mg, 1.34 mmol) were suspended in ethanol (1.9 mL) and dioxane (5 mL), then cooled to 0° C. Borane tert-butylamine complex (385 mg, 4.43 mmol) was added, followed by the dropwise addition 10% aq. HCl (3.6 mL). The reaction mixture was stirred at 0° C. for 2.5 hours. After this time, $Na_2CO_3$ was added until gas evolution ceased, and the mixture was partitioned between sat. aq. $NaHCO_3$ and $CH_2Cl_2$. The organic layer was dried over $Na_2SO_4$, filtered, and concentrated. The crude reaction mixture was purified via $SiO_2$ column chromatography eluting with 3:2 EtOAc/hexane to elute 3β (TLC $R_f$=0.33 in 3:2 EtOAc/hexane) and then with 100% EtOAc to elute 3α (TLC $R_f$=0.09 in 3:2 EtOAc/hexane). Aglycon 3β was obtained as a foam (137 mg, 25% yield). $^1$H NMR ($CDCl_3$, 400 MHz) δ 5.88 (s, 1H), 4.99 (A of ABX, 1H, J=18.0, 1.6), 4.81 (B of ABX, 1H, J=18.0, 1.5), 3.55 (s, 3H), 3.26 (br s, 1H), 2.79 (m, 1H), 2.15 (m, 2H), 1.85 (m, 3H), 1.74-1.22 (m, 17H), 0.94 (s, 3H), 0.87 (s, 3H); $^{13}$C NMR ($CDCl_3$, 100 MHz): δ 174.7, 174.6, 117.8, 85.7, 73.6, 62.6, 55.1, 51.1, 49.7, 42.0, 40.1, 36.7, 35.8, 35.7, 33.3, 30.5, 28.8, 27.0, 26.7, 23.9, 22.9, 21.3, 21.2, 15.9; Electrospray ionization-MS m/z (M+H) calculated for $C_{24}H_{38}NO_4$ 404.6, observed 404.4. Aglycon 3α was obtained as a white powder (227 mg, 44% yield). $^1$H NMR ($CDCl_3$, 400 MHz) δ 5.86 (s, 1H), 4.98 (A of ABX, 1H, J=18.1, 1.4), 4.80 (B of ABX, 1H, J=18.1, 1.7), 3.55 (s, 3H), 2.91 (tt, 1H, J=11.1, 3.9), 2.76 (m, 1H), 2.15 (m, 2H), 1.84 (m, 3H), 1.86-1.17 (m, 17H), 0.93 (s, 3H), 0.87 (s, 3H); $^{13}$C NMR ($CDCl_3$, 100 MHz): δ 175.2, 174.6, 117.3, 85.1, 73.5, 62.5, 60.3, 50.8, 49.6, 41.8, 41.5, 39.8, 36.1, 35.3, 35.0, 33.0, 30.9, 27.0, 26.8, 25.3, 23.4, 21.5, 20.8, 15.7; Electrospray ionization-MS m/z (M+H) calculated for $C_{24}H_{38}NO_4$ 404.6, observed 404.4.

Neoglycoside 4β. Aglycon 3β (18.4 mg, 45.6 μmol) and D-glucose (8.6 mg, 47.9 μmol) were dissolved in 3:1 DMF/AcOH (500 μL) and stirred at 60° C. for 48 h. The crude reaction mixture was concentrated, and examined by $^1$H NMR to reveal a 4β:3β ratio of 7:3 (70% crude yield). Neoglycoside 4 μl: (TLC $R_f$=0.27 in 20% EtOH/$CHCl_3$) $^1$H NMR ($CD_3OD$, 500 MHz) δ 5.90 (s, 1H), 5.03 (A of ABX, 1H, J=18.3, 1.1), 4.92 (B of ABX, 1H, J=18.3, 1.4), 4.09 (d, 1H, J=8.8), 3.81 (A of ABX, 0.5H, J=12.0, 1.9), 3.72 (s, 3H), 3.66 (B of ABX, 0.5H, J=12.0, 5.1), 3.59 (t, 1H, J=9.0), 3.44

(br s, 1H), 3.40-3.30 (m, 2H), 3.15 (m, 1H), 2.84 (m, 1H), 2.19 (m, 2H), 2.01 (td, 1H, J=14.8, 2.8), 1.88-1.44 (m, 15H), 1.27 (m, 5H), 1.00 (s, 3H), 0.89 (s, 3H); Electrospray ionization-MS m/z (M+H) calculated for $C_{30}H_{48}NO_9$ 566.7, observed 566.4.

Neoglycoside 4α. Aglycon 3α (34.0 mg, 84.3 μmol) and D-glucose (15.9 mg, 88.5 μmol) were dissolved in 3:1 DMF/AcOH (940 μL) and stirred at 60° C. for 48 h. The crude reaction mixture was concentrated, and examined by $^1$H NMR to reveal a 4α:3α ratio of 37:50 (74% crude yield).

Neoglycoside 4α: ($TLC_{Rf}$=0.09 in 10% EtOH/CHCl$_3$) $^1$H NMR (CD$_3$OD, 500 MHz) δ 5.90 (br t, 1H, J=1.6), 5.04 (A of ABX, 1H, J=18.4, 1.4), 4.92 (B of ABX, 1H, J=18.4, 1.7), 4.17 (d, 1H, J=8.7), 3.81 (A of ABX, 0.5H, J=12.1, 2.0), 3.70 (s, 3H), 3.66 (B of ABX, 0.5H, J=12.1, 5.2), 3.57 (t, 1H, J=8.2), 3.39-3.30 (m, 2H), 3.18 (m, 2H), 2.84 (m, 2H), 2.21 (m, 2H), 1.99-1.34 (m, 19H), 1.07 (td, 1H, J=14.0, 3.5), 0.95 (s, 3H), 0.89 (s, 3H); Electrospray ionization-MS m/z (M+H) calculated for $C_{30}H_{48}NO_9$ 566.7, observed 566.4.

Aglycon 3β Data Collection. X-ray quality crystals of 3β were obtained via slow evaporation from chloroform. A colorless crystal with approximate dimensions 0.41×0.36×0.35 mm$^3$ was selected under oil in ambient conditions and attached to the tip of a nylon loop. The crystal was mounted in a stream of cold nitrogen at 100° K. and manually centered in the X-ray beam while visualizing via video camera. The crystal evaluation and data collection were performed on a Bruker CCD-1000 diffractometer with Mo Kα (λ=0.71073 Å) radiation and a diffractometer to crystal distance of 4.9 cm. The initial cell constants were obtained from three series of ω scans at different starting angles. Each series consisted of 20 frames collected at intervals of 0.3° in a 6° range about ω with the exposure time of 10 sec per frame. A total of 54 reflections were obtained. The reflections were successfully indexed by an automated indexing routine built in the SMART program (S1). The final cell constants were calculated from a set of 6432 strong reflections from the actual data collection. The data were collected by using the hemisphere data collection routine. The reciprocal space was surveyed to the extent of a full sphere to a resolution of 0.80 Å. A total of 8852 data were harvested by collecting three sets of frames with 0.25° scans in ω with an exposure time 30 sec per frame. These redundant datasets were corrected for Lorentz and polarization effects. The absorption correction was based on fitting a function to the empirical transmission surface as sampled by multiple equivalent measurements.

Aglycon 3β Structure Refinement. The systematic absences in the diffraction data were consistent for the space groups P1$^-$ and P1. The E-statistics were inconclusive and only the non-centrosymmetric space group P1 yielded chemically reasonable and computationally stable results of refinement (S1). A successful solution by the direct methods provided most on hydrogen atoms from the E-map. The remaining non-hydrogen atoms were located in an alternating series of least-squares cycles and difference Fourier maps. All non-hydrogen atoms were refined with anisotropic displacement coefficients. All hydrogen atoms were included in the structure factor calculation at idealized positions and were allowed to ride on the neighboring atoms with relative isotropic displacement coefficients. There are two symmetry independent molecules of 3β in the asymmetric unit (and incidentally the unit cell) with essentially identical geometries. The absolute configuration could not be unequivocally established from the experimental data but was assigned from synthesis. There is also one solvate molecule of water per two molecules of 3β in the unit cell. The final least-squares refinement of 552 parameters against 7847 data resulted in residuals R (based on $F^2$ for $I \geq 2\sigma$) and wR (based on $F^2$ for all data) of 0.0392 and 0.1023, respectively. The final difference Fourier map was featureless. The ORTEP diagrams are drawn with 50% probability ellipsoids.

TABLE 1

Crystal data and structure refinement for 3β

| | |
|---|---|
| Empirical formula | $C_{24}H_{37}NO_4 \cdot ½ H_2O$ |
| Formula weight | 412.55 |
| Temperature | 100 (2) K |
| Wavelength | 0.71073 Å |
| Crystal system | Triclinic |
| Space group | P1 |
| Unit cell dimensions | a = 7.7964 (5) Å     α = 95.2600 (10)° |
| | b = 7.8330 (5) Å     β = 95.5760 (10)° |
| | c = 17.9391 (13) Å   γ = 99.3590 (10)° |
| Volume | 1069.37 (12) Å$^3$ |
| Z | 2 |
| Density (calculated) | 1.281 Mg/m$^3$ |
| Absorption coefficient | 0.087 mm$^{-1}$ |
| F (000) | 450 |
| Crystal size | 0.41 × 0.36 × 0.35 mm$^3$ |
| Theta range for data collection | 2.30 to 26.39°. |
| Index ranges | $-9 \leq h \leq 9, -9 \leq k \leq 9, -22 \leq l \leq 22$ |
| Reflections collected | 8852 |
| Independent reflections | 7847 [R (int) = 0.0103] |
| Completeness to theta = 26.39° | 98.7% |
| Absorption correction | Multi-scan with SADABS |
| Max. and min. transmission | 0.9702 and 0.9652 |
| Refinement method | Full-matrix least-squares on $F^2$ |
| Data/restraints/parameters | 7847/7/552 |
| Goodness-of-fit on $F^2$ | 1.028 |
| Final R indices [I > 2sigma(I)] | R1 = 0.0392, wR2 = 0.1000 |
| R indices (all data) | R1 = 0.0412, wR2 = 0.1023 |
| Absolute structure parameter | N/A - assigned from synthesis |
| Largest diff. peak and hole | 0.319 and −0.353 e · Å$^{-3}$ |

Neoglycoside 4β Data Collection. X-ray quality crystals of 4β was obtained by dissolving the neoglycoside in EtOH (~40 mg mL$^{-1}$) and slowly crystallizing via vapor diffusion using hexanes. A colorless crystal with approximate dimensions 0.43×0.31×0.15 mm$^3$ was selected under oil in ambient conditions and attached to the tip of a nylon loop. The crystal was mounted in a stream of cold nitrogen at 100° K. and manually centered in the X-ray beam while visualizing via video camera. The crystal evaluation and data collection were performed on a Bruker CCD-1000 diffractometer with Mo K$_α$ (λ=0.71073 Å) radiation and the diffractometer to crystal distance of 7.36 cm. The initial cell constants were obtained from three series of ω scans at different starting angles. Each series consisted of forty frames collected at intervals of 0.30 in a 6° range about ω with the exposure time of fifteen seconds per frame. A total of 149 reflections were obtained. The reflections were successfully indexed by an automated indexing routine built in the SMART program (S1). The final cell constants were calculated from a set of 2244 strong reflections from the actual data collection. The data were collected by using the multi-run data collection routine. The reciprocal space was surveyed to the extent of a full sphere to a resolution of 0.80 Å. A total of 14014 data were harvested by collecting six sets of frames with 0.30° scans in ω with an exposure time 14 sec per frame. These highly redundant datasets were corrected for Lorentz and polarization effects. The absorption correction was based on fitting a function to the empirical transmission surface as sampled by multiple equivalent measurements.

Neoglycoside 4β Structure Solution and Refinement. The systematic absences in the diffraction data were consistent for the space groups P1$^-$ and P1. The E-statistics strongly suggested the centrosymmetric space group P1 that yielded chemically reasonable and computationally stable results of refinement (S1). A successful solution by the direct methods provided all non-hydrogen atoms from the E-map. All non-hydrogen atoms were refined with anisotropic displacement coefficients. Soft restraints were applied to thermal displacement coefficients of atom C(6'). All hydrogen atoms were included in the structure factor calculation at idealized positions and were allowed to ride on the neighboring atoms with relative isotropic displacement coefficients. The absolute configurations of the chiral atoms were assigned from the known synthetic procedure. The crystal proved to be a twin with a 2:1 component ratio; the components are related about a 179.8° rotation about the [1, −1, 0] vector in real space. There are two independent molecules of the chiral compound and one molecule of solvated ethanol in the unit cell. The final least-squares refinement of 767 parameters against 14014 data resulted in residuals R (based on $F^2$ for $1 \geq 2\sigma$) and wR (based on $F^2$ for all data) of 0.0639 and 0.1583, respectively.

TABLE 2

Crystal data and structure refinement for 4β.

| | |
|---|---|
| Empirical formula | $C_{30}H_{47}NO_9 \cdot \frac{1}{2}CH_3CH_2OH$ |
| Formula weight | 588.72 |
| Temperature | 100 (2) K |
| Wavelength | 0.71073 Å |
| Crystal system | Triclinic |
| Space group | P1 |
| Unit cell dimensions | a = 10.1923 (5) Å  α = 82.533 (2)° |
| | b = 10.2765 (5) Å  β = 75.932 (2)° |
| | c = 16.1912 (8) Å  γ = 64.9970 (10)° |
| Volume | 1490.15 (13) Å$^3$ |
| Z | 2 |
| Density (calculated) | 1.312 Mg/m$^3$ |
| Absorption coefficient | 0.096 mm$^{-1}$ |
| F (000) | 638 |
| Crystal size | 0.43 × 0.31 × 0.15 mm$^3$ |
| Theta range for data collection | 2.25 to 26.39°. |
| Index ranges | $-12 \leq h \leq 12, -12 \leq k \leq 12,$ |
| | $-20 \leq l \leq 20$ |
| Reflections collected | 14014 |
| Independent reflections | 14014 [R (int) = 0.0000] |
| Completeness to theta = 26.39° | 92.2% |
| Max. and min. transmission | 0.9857 and 0.9598 |
| Refinement method | Full-matrix least-squares on $F^2$ |
| Data/restraints/parameters | 14017/9/767 |
| Goodness-of-fit on $F^2$ | 0.995 |
| Final R indices [I > 2sigma (l)] | R1 = 0.0639, wR2 = 0.1470 |
| R indices (all data) | R1 = 0.0898, wR2 = 0.1583 |
| Absolute structure parameter | −0.2 (10) |
| Largest diff. peak and hole | 1.187 and −0.431 e · Å$^{-3}$ |

Figure 4:
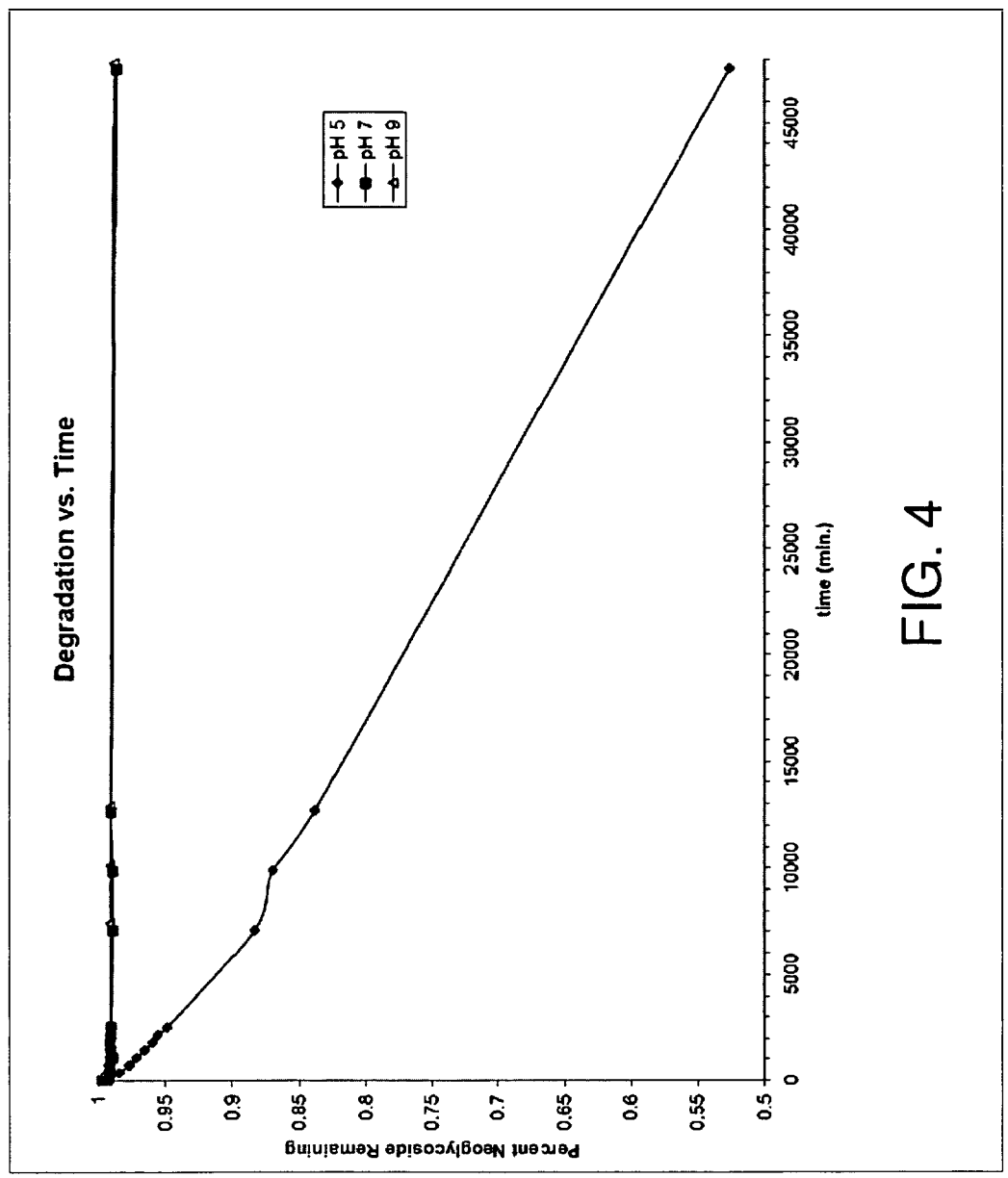
FIG. 4 is a graphic representation of the results of studies on the hydrolytic stability of neoglycoside 4α. The chemical stability of the neoglycosidic linkage was examined by monitoring the hydrolytic degradation of neoglycoside 4α in a 3 mM solution of 1:1 DMSO/buffer. Three buffers were used, 50 mM acetate buffer (pH 5), 50 mM phosphate buffer (pH 7), and 50 mM Tris buffer (pH 9). Neoglycoside degradation was monitored by reverse phase HPLC on an Agilent Zorbax Eclipse XDB-C8 column (4.6×150 mm) with a flow rate of 0.8 mL min$^{-1}$ and a linear gradient of 49% CH$_3$OH/H$_2$O to 89% CH$_3$OH/H$_2$O over 20 min. At t=0, neoglycoside 4α in 500 μL DMSO was added to 500 μL buffer, and the resulting solution was vortexed for 40 sec, then immediately injected onto the HPLC. Peak areas at 220 nm were used to estimate the neoglycoside/aglycon ratio, which is reported as "percent neoglycoside remaining" [Aneoglycoside/(Aneoglycoside+Aaglycon)] for each of the three buffer systems.
Figure 5A:
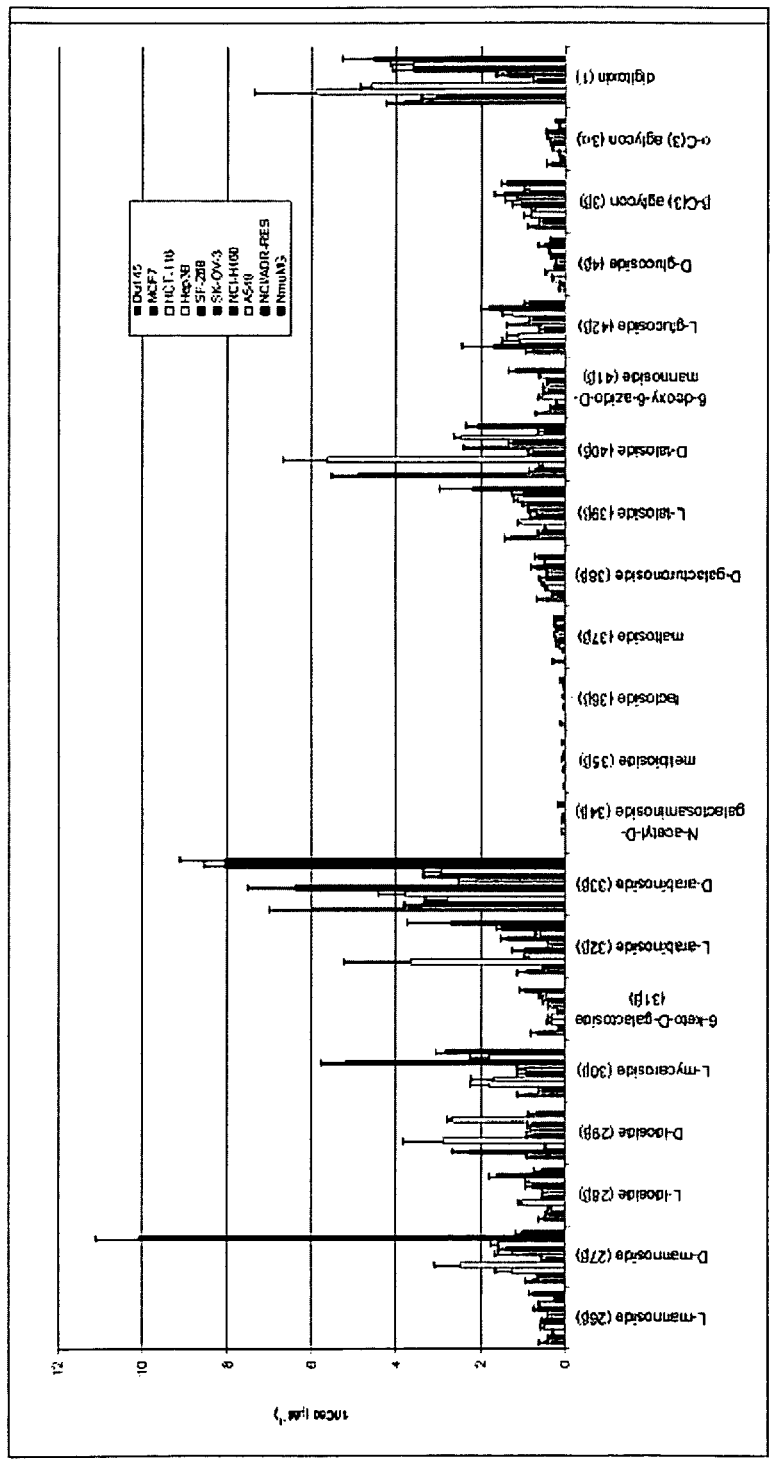
FIG. 5A and FIG. 5B are graphical representation of the results of a high-throughput assays of the cytotoxicity against cancer cell lines of members of a neoglycoside library of one embodiment of the present invention. In the assay, live cells were distinguished by the presence of a ubiquitous intracellular enzymatic activity which converts the non-fluorescent cell-permeable molecule calcein AM to the intensely fluorescent molecule calcein, which is retained within live cells. The IC$_{50}$ value for each library member represents at least six replicates of dose-response experiments conducted over five concentrations using two-fold dilutions. For the entire panel of 81 compounds in 10 cell lines, the average error was 17%. IC$_{50}$ Reciprocal IC$_{50}$ values as a function of library member and cell line. Standard errors are depicted with error bars. Numerical values and corresponding error values can be found in Table 4. Du145: human colon carcinoma; MCF$_7$: human breast carcinoma; HCT-116: human colon carcinoma, Hep3B: human liver carcinoma; SF-268: human CNS glioblastoma; SK-OV-3: human ovary adenocarcinoma; NCI-H460: human lung carcinoma; A549: human lung adenocarcinoma; NCI/ADR-RES: human breast carcinoma; NmuMG: mouse mammary normal epithelial.
Figure 5B:
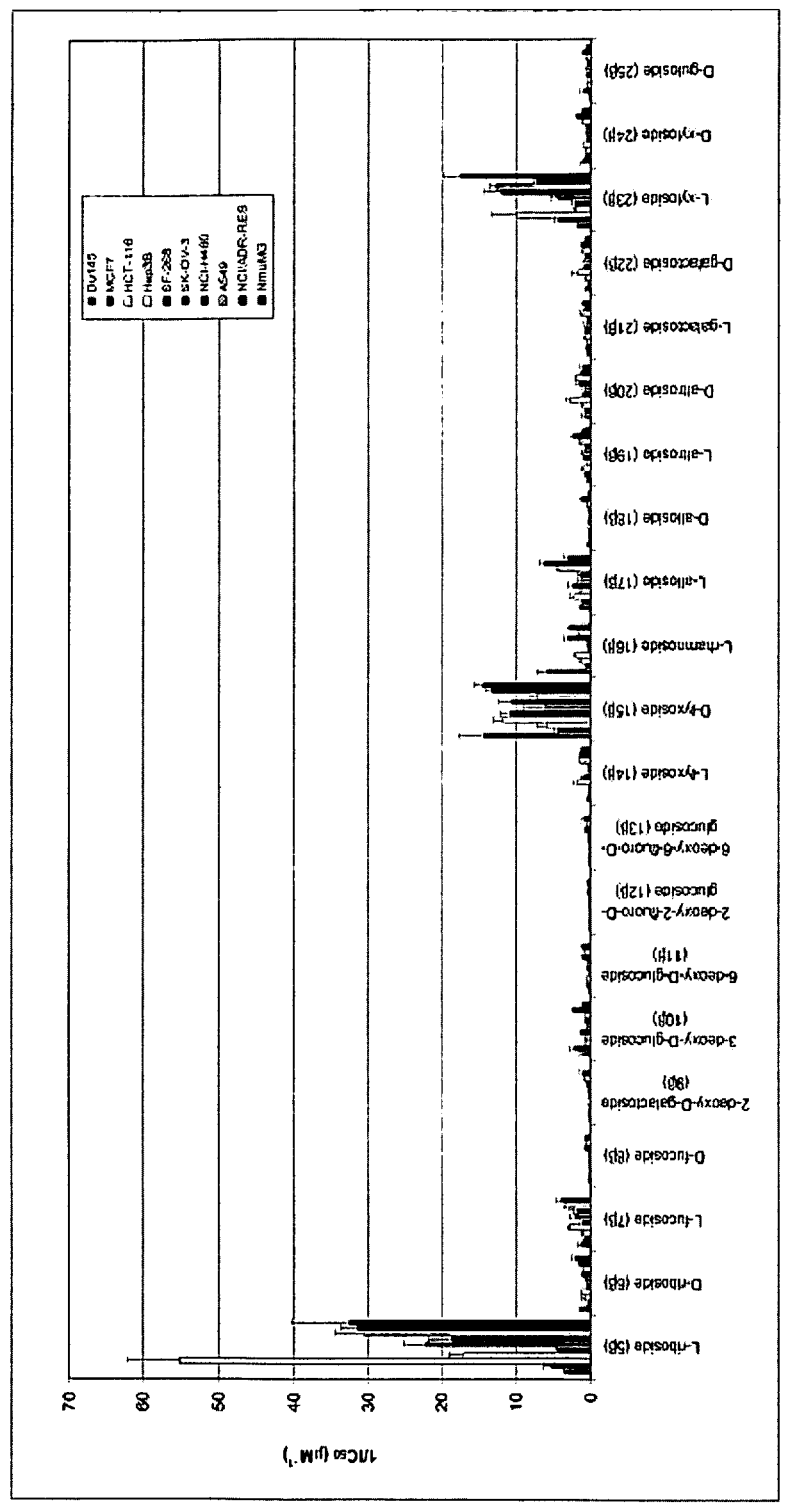
Figure 6:
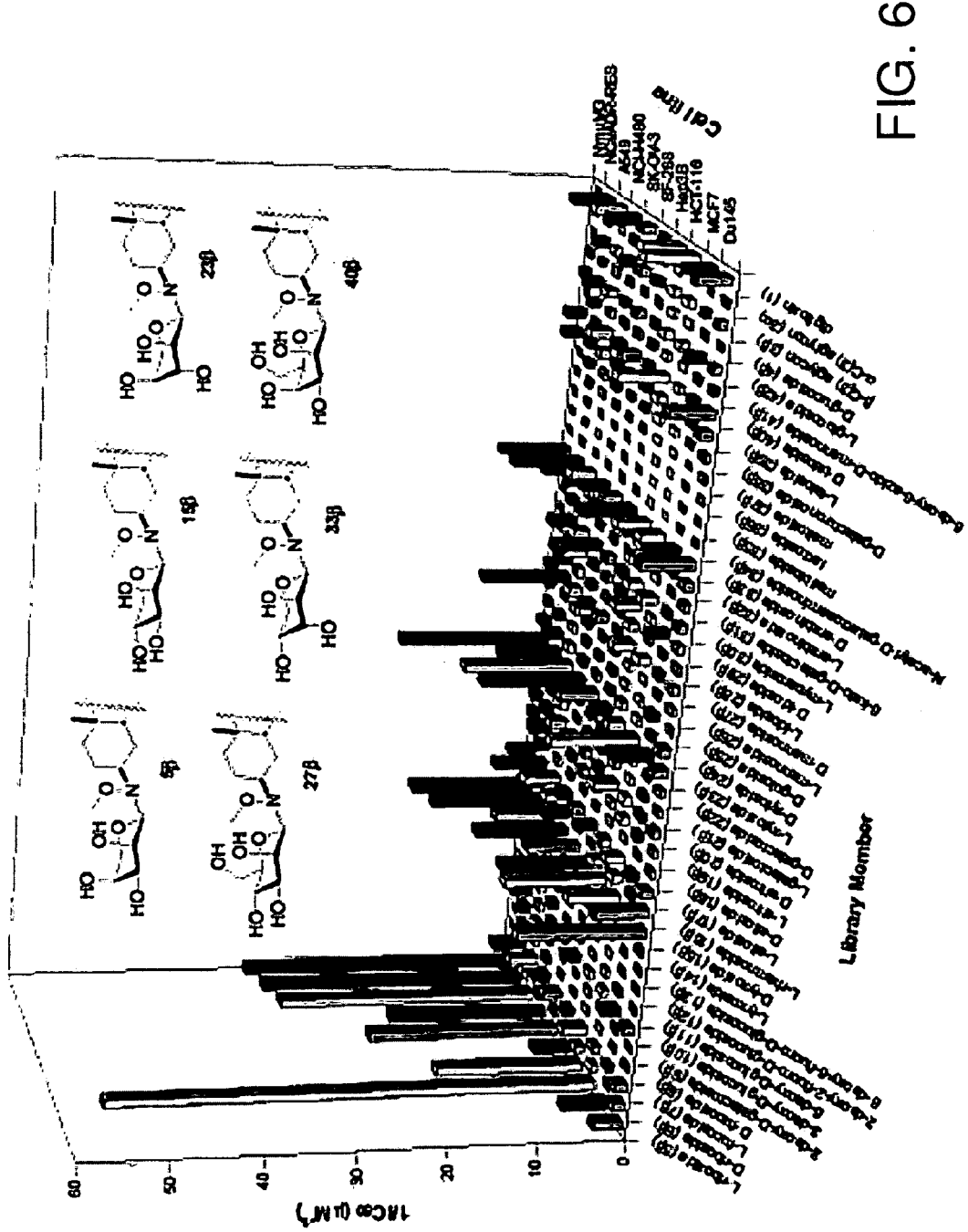
FIG. 6. is a graphical summary of the results of the high-throughput cytotoxicity assay, displaying data $IC_{50}$ data from Table 4 and FIG. A and FIG. 5B. Reciprocal $IC_{50}$ values are displayed for clarity showing an $IC_{50}$ range of 18 nM (5β, HCT-116) to >25 μM (e.g. 35β, all cell lines). Six library member "hits" are depicted in pyranose $^4C_1$ conformations to facilitate structural comparisons.

Hydrolytic Stability of 4α. The chemical stability of the neoglycosidic linkage was examined by monitoring the hydrolytic degradation of neoglycoside 4α in a 3 mM solution of 1:1 DMSO/buffer. Three buffers were used, 50 mM acetate buffer (pH 5), 50 mM phosphate buffer (pH 7), and 50 mM Tris buffer (pH 9). Neoglycoside degradation was monitored by reverse phase HPLC on an Agilent Zorbax Eclipse XDB-C8 column (4.6×150 mm) with a flow rate of 0.8 mL min$^{-1}$ and a linear gradient of 49% $CH_3OH/H_2O$ to 89% $CH_3OH/H_2O$ over 20 min. At t=0, neoglycoside 4α in 500 μL DMSO was added to 500 μL buffer, and the resulting solution was vortexed for 40 sec, then immediately injected onto the HPLC. Peak areas at 220 nm were used to estimate the neoglycoside/aglycon ratio, which is reported as "percent neoglycoside remaining" [$A_{neoglycoside}/(A_{neoglycoside}+A_{aglycon})$] for each of the three buffer systems (see FIG. 4).

Library Synthesis and Purification. Aglycon 3β or 3α (~40 μmol) was added to 4 mL glass vials equipped with stirring fleas. The appropriate sugar (2 eq.) was added to each vial, followed by 3:1 DMF/AcOH (final concentration of aglycon=90 mM). The reaction mixtures were stirred at 40° C. using a stir plate equipped with a 48-well reaction block and a contact thermometer. After 2 days, the reaction mixtures were concentrated via Speed-Vac and suspended in 5% EtOH/CHCl$_3$. The crude suspensions were purified in parallel on disposable SiO$_2$ solid phase extraction columns using a 24-port vacuum manifold. Library members (β and α) 5-16, 23, 24, 30-36, and 41 were purified on 1000 mg columns eluting first with 5 mL 5% EtOH/CHCl$_3$ to remove the remaining aglycon and second with 5 mL 15% EtOH/CHCl$_3$ to collect the product neoglycosides. Library members (β and α) 4, 17-22, 25-29, 37-40, and 42 were purified on 500 mg columns eluting first with 4 mL 5% EtOH/CHCl$_3$ to remove the remaining aglycon and second with 5 mL 25% EtOH/CHCl$_3$ to collect the product neoglycosides. The product solutions were concentrated via Speed-Vac, weighed, and dissolved in DMSO to make 30 mM or 20 mM stock solutions. The stock solutions were characterized by LCMS using reverse phase HPLC on an Agilent Zorbax Eclipse XDB-C8 column (4.6×150 mm) with a flow rate of 0.8 mL/min and a linear gradient of 45% $CH_3OH/H_2O$ to 85% $CH_3OH/H_2O$ over 20 min and electrospray ionization. Library member purities were estimated by dividing the sum of the peak areas at 220 nm of peaks corresponding to the desired product mass by the total area of all peaks. For mass information, the purity of specific library members, and a tabulation of which members display greater than 90% of a single product isomer as judged by LCMS, see Table 3, below. Average library purity was 91%.

TABLE 3

LCMS information for neoglycoside library

| Neoglycoside | Calculated Mass | Observed Mass | Percent Purity | 90% Isomeric Purity | Neoglycoside | Calculated Mass | Observed Mass | Percent Purity | 90% Isomeric Purity |
|---|---|---|---|---|---|---|---|---|---|
| 4β | 566.7 | 566.7 | 97 | + | 4α | 566.7 | 566.7 | 98 | + |
| 5β | 536.6 | 536.6 | 98 | − | 5α | 536.6 | 536.6 | 100 | − |
| 6β | 536.6 | 536.6 | 99 | − | 6α | 536.6 | 536.6 | 99 | + |
| 7β | 550.7 | 550.7 | 97 | + | 7α | 550.7 | 550.7 | 96 | − |
| 8β | 550.7 | 550.7 | 100 | + | 8α | 550.7 | 550.7 | 99 | − |
| 9β | 550.7 | 550.7 | 21 | − | 9α | 550.7 | 550.7 | 0 | − |
| 10β | 550.7 | 550.7 | 100 | − | 10α | 550.7 | 550.7 | 97 | − |
| 11β | 548.7 | 548.7 | 100 | + | 11α | 548.7 | 548.7 | 100 | + |
| 12β | 568.6 | 568.6 | 88 | − | 12α | 568.6 | 568.6 | 95 | + |
| 13β | 568.6 | 568.6 | 100 | + | 13α | 568.6 | 568.6 | 100 | + |
| 14β | 536.6 | 536.6 | 97 | + | 14α | 536.6 | 536.6 | 99 | + |
| 15β | 536.6 | 536.6 | 95 | + | 15α | 536.6 | 536.6 | 99 | + |
| 16β | 568.5 | 568.5 | 91 | − | 16α | 568.5 | 568.5 | 99 | − |

TABLE 3-continued

LCMS information for neoglycoside library

| Neoglycoside | Calculated Mass | Observed Mass | Percent Purity | 90% Isomeric Purity | Neoglycoside | Calculated Mass | Observed Mass | Percent Purity | 90% Isomeric Purity |
|---|---|---|---|---|---|---|---|---|---|
| 17β | 566.7 | 566.7 | 100 | − | 17α | 566.7 | 566.7 | 95 | − |
| 18β | 566.7 | 566.7 | 98 | + | 18α | 566.7 | 566.7 | 98 | + |
| 19β | 566.7 | 566.7 | 65 | − | 19α | 566.7 | 566.7 | 94 | − |
| 20β | 566.7 | 566.7 | 88 | − | 20α | 566.7 | 566.7 | 91 | − |
| 21β | 566.7 | 566.7 | 96 | − | 21α | 566.7 | 566.7 | 91 | − |
| 22β | 566.7 | 566.7 | 93 | − | 22α | 566.7 | 566.7 | 92 | − |
| 23β | 536.6 | 536.6 | 99 | + | 23α | 536.6 | 536.6 | 100 | + |
| 24β | 536.6 | 536.6 | 99 | + | 24α | 536.6 | 536.6 | 97 | + |
| 25β | 566.7 | 566.7 | 89 | + | 25α | 566.7 | 566.7 | 93 | + |
| 26β | 566.7 | 566.7 | 90 | − | 26α | 566.7 | 566.7 | 91 | − |
| 27β | 566.7 | 566.7 | 88 | − | 27α | 566.7 | 566.7 | 91 | − |
| 28β | 566.7 | 566.7 | 52 | − | 28α | 566.7 | 566.7 | 61 | − |
| 29β | 566.7 | 566.7 | 61 | − | 29α | 566.7 | 566.7 | 34 | − |
| 30β | 548.7 | 548.7 | 98 | + | 30α | 548.7 | 548.7 | 97 | + |
| 31β | 578.7 | 578.7 | 62 | − | 31α | 578.7 | 578.7 | 86 | − |
| 32β | 536.6 | 536.6 | 96 | + | 32α | 536.6 | 536.6 | 98 | − |
| 33β | 354.6 | 354.6 | 98 | + | 33α | 354.6 | 354.6 | 99 | − |
| 34β | 607.7 | 607.7 | 97 | − | 34α | 607.7 | 607.7 | 99 | − |
| 35β | 728.8 | 728.8 | 92 | + | 35α | 728.8 | 728.8 | 88 | + |
| 36β | 728.8 | 728.8 | 64 | + | 36α | 728.8 | 728.8 | 89 | + |
| 37β | 728.8 | 728.8 | 96 | + | 37α | 728.8 | 728.8 | 97 | + |
| 38β | 580.7 | 580.7 | 70 | − | 38α | 580.7 | 580.7 | 22 | − |
| 39β | 566.7 | 566.7 | 89 | + | 39α | 566.7 | 566.7 | 96 | + |
| 40β | 566.7 | 566.7 | 96 | + | 40α | 566.7 | 566.7 | 97 | + |
| 41β | 562.7 | 562.7 | 87 | − | 41α | 562.7 | 562.7 | 83 | − |
| 42β | 566.7 | 566.7 | 89 | + | 42α | 566.7 | 566.7 | 98 | + |

Cell Culture: All cell lines except NmuMG were maintained in RPMI 1640 medium from InVitrogen (Cat No. 11875-085) supplemented with 10% w/v fetal bovine serum (FBS) from ICN (Cat No. 2916154) and penicillin-streptomycin (PS) (100 U/mL and 100 μg/mL) from InVitrogen (Cat No. 15140-122). NmuMG cells were maintained in DMEM medium from InVitrogen (Cat No. 11965-084) supplemented with 10% w/v fetal bovine serum (FBS) from ICN (Cat No. 2916154), 10 μg/ml insulin (InVitrogen Cat No 12585-014), and penicillin-streptomycin (PS) (100 U/mL and 100 μg/mL) from InVitrogen (Cat No. 15140-122). Cells were harvested by trypsinization using 0.25% w/v trypsin and 0.1% w/v EDTA from InVitrogen (Cat No. 15-050-057) and then counted in a hemocytometer in duplicate with better than 10% agreement in field counts. Cells were plated at a cell density of 10,000-15,000 cells/well of each Corning Costar 96-well black tissue culture treated microtiter plate (Fisher Cat No. 07-200-627). Cells were grown for 1 h at 37° C., with 5% $CO_2$ in a humidified incubator to allow cell attachment to occur before compound addition.

Library Member Handling and Preparation for Cytotoxicity Assays: Library members were stored at −20° C. under dessicating conditions before the assay. Library member stocks (100×) were prepared in Corning Costar polypropylene 96-well V-bottom polypropylene microtiter plates (Fisher Cat No. 07-200-695). Five serial 1:2 dilutions were made with anhydrous DMSO at 100× the final concentration used in the assay.

Library Member Addition: The library member-containing plates were diluted 1:10 with complete cell culture media. The 10× stocks (10 μL) were added to the attached cells using a Biomek FX liquid handler (Beckman-Coulter). Library member stocks (10 μL) were added to 90 μL of cells in each plate to insure full mixing of stocks with culture media using a Beckman FX liquid handler with 96-well head.

Determination of Cytotoxicity: Cells were incubated with the library members for 72 h before fluorescence reading. Test plates were removed from the incubator and washed 1× in sterile PBS to remove serum containing calcium esterases. Calcein AM reagent (30 μL, 1 M) was added and the cells were incubated for 30 min at 37° C. Plates were read for emission using a fluorescein filter (excitation 485 nm, emission 535 nm).

$IC_{50}$ Calculation: For each library member, at least six dose response experiments were conducted. Within each experiment, percent inhibition values at each concentration were expressed as a percentage of the maximum fluorescence emission signal observed for a 0 nM control. To calculate $IC_{50}$, percent inhibitions were plotted as a function of log [concentration] and then fit to a four-parameter logistic model that allowed for a variable Hill slope using $XL_{fit}$ 4.1.

Cytotoxicity Assays. All cell lines except NmuMG were maintained in RPMI 1640 medium supplemented with 10% w/v fetal bovine serum (FBS) and penicillin-streptomycin (PS) (100 U/mL and 100 μg/mL). NmuMG cells were maintained in DMEM medium supplemented with 10% w/v fetal bovine serum (FBS), 10 μg/ml insulin, and penicillin-streptomycin (PS) (100 U/mL and 100 μg/mL). Cells were harvested by trypsinization using 0.25% w/v trypsin and 0.1% w/v EDTA and then counted in a hemocytometer in duplicate with better than 10% agreement in field counts. Cells were plated at a cell density of 10,000-15,000 cells/well of each 96-well black tissue culture treated microtiter plate. Cells were grown for 1 h at 37° C., with 5% $CO_2$ in a humidified incubator to allow cell attachment to occur before compound addition. Library members were stored at −20° C. under dessicating conditions before the assay. Library member stocks (100×) were prepared in polypropylene 96-well V-bottom polypropylene microtiter plates. Five serial 1:2 dilutions were made with anhydrous DMSO at 100× the final concentration used in the assay. The library member-containing plates were diluted 1:10 with complete cell culture media. The 10× stocks (10 μL) were added to the attached cells using a Biomek FX liquid handler. Library member stocks (10 μL)

were added to 90 µL of cells in each plate to insure full mixing of stocks with culture media using a Beckman FX liquid handler with 96-well head. Cells were incubated with the library members for 72 h before fluorescence reading. Test plates were removed from the incubator and washed 1× in sterile PBS to remove serum containing calcium esterases. Calcein AM reagent (30 µL, 1 M) was added and the cells were incubated for 30 min at 37° C. Plates were read for emission using a fluorescein filter (excitation 485 nm, emission 535 nm).

$IC_{50}$ Calculations. For each library member, at least six dose response experiments were conducted. Within each experiment, percent inhibition values at each concentration were expressed as a percentage of the maximum fluorescence emission signal observed for a 0 nM control. To calculate $IC_{50}$, percent inhibitions were plotted as a function of log [concentration] and then fit to a four-parameter logistic model that allowed for a variable Hill slope using XLfit 4.1.

Figure 2:
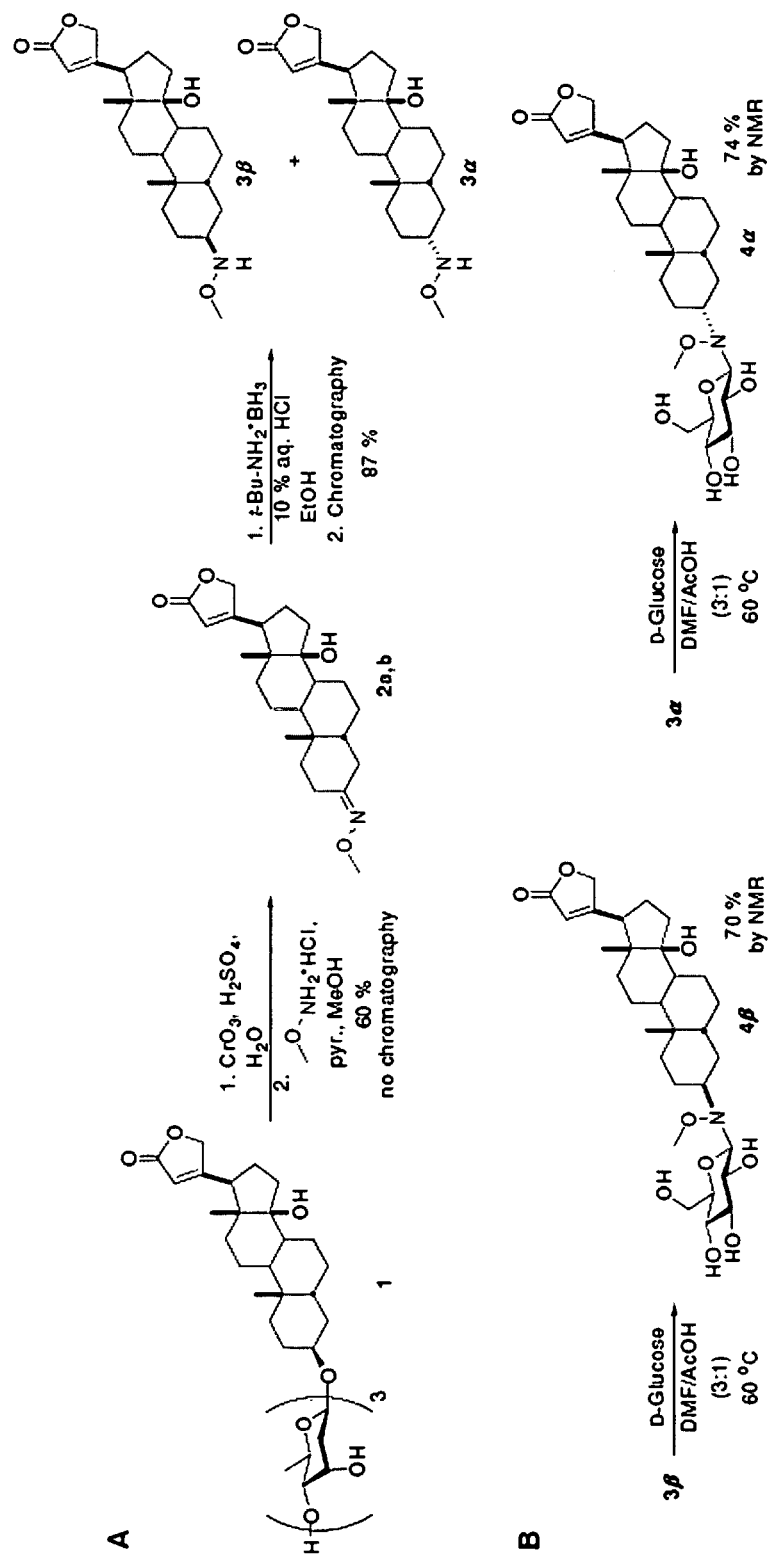
FIG. 2A is a schematic illustration showing that aglycons having a secondary alkoxyamine, 3β and its C(3) epimer 3α, were generated in three simple steps from the parent natural product digitoxin.
FIG. 2B is a schematic illustration showing the reaction of aglycons 3β and 3α with D-glucose (2 equiv.) in 3:1 DMF/acetic acid at 60° C. to form neoglycosides 4β and 4α respectively, in >70% yield by $^1$H NMR.
Figure 3:
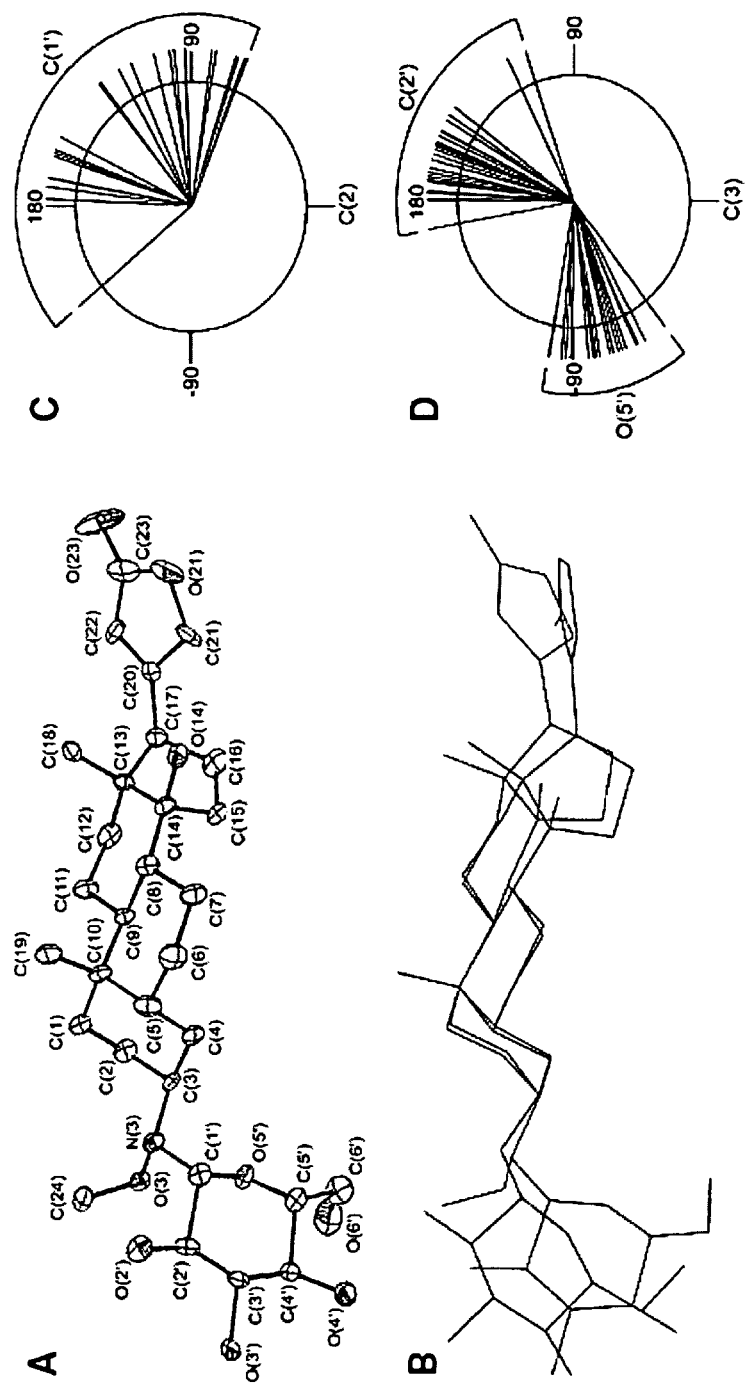
FIG. 3A is a schematic illustration of the solid state structure of 4β shown with 50% thermal probability ellipsoids. Hydrogen atoms are omitted for clarity.
FIG. 3B is a schematic illustration of the solid state structure of 4β (red) superimposed on the solid state structure of a homologous O-glucoside, actodigin.
FIG. 3C is a Newman projection along the C(2)-C(3)-N(3)-C(1') torsion of neoglycoside 4β and the corresponding torsion of 23 known cardiac glycosides showing that the neoglycoside torsion falls within the range of torsions displayed in the solid state by the known cardiac glycosides.
FIG. 3D is a Newman projection along the C(3)-N(3)-C(1')—C(2') torsion of 4β and the corresponding torsions of 23 known cardiac glycosides reveals that the neoglycoside torsion falls on the periphery of the narrow range of orientations displayed by natural O-glycosides. The crystallographic information displayed came from the following sources: actogenin (Fullerton, D. S. et al., Mol. Pharmacol. (1980) 17, 43), oleandrin (Kartha, G. et al., Cryst. Struct. Commun. (1981) 10, 1323), digoxigenin monodigitoxoside monohydrate (Go, K. et al., Cryst. Struct. Commun. (1982) 11, 279), digoxigenin bis(digitoxoside) (Go, K. et al., Cryst. Struct. Commun. (1982) 11, 285), digoxigenin bis(digitoxoside) tetrahydrate (Go, K. et al., Acta Crystallogr., Sect. B: Struct. Sci. (1989) 45, 306), (3β,5β,14β,20E)-methyl-3-((2,6-dideoxy-β-ribohexopyranosyl)oxy)-14-hydroxypregn-20-ene-21-carboxylate (S7), (3β,5β,14β,20E)-methyl-3-((2,6-dideoxy-3,4-O-(1-methylethylidene)-13-D-ribo-hexopyranosyl)oxy)-14-hydroxypregn-20-ene-21-carboxylate (Kihara, M. et al., Tetrahedron (1984) 40, 1121), (3β,5β,14β)-methyl-3-((2,6-dideoxy-3,4-O-(1-methylethylidene)-α-ribo-hexopyranosyl)oxy)-14-hydroxy-21-methylene-(pregane-21-carboxylate) (Kihara, M., et al. (1984)), (20S)-20,22-dihydrodigitoxigenin-3-(2,6-dideoxy-3,4-O-(1-methylethylidene)-β-D-ribo-hexopyranoside) (Kihara, M. et al., (1984)), digoxin (Go, K. et al., Cryst. Struct. Commun. (1979) 8, 149; Go, K et al., J. P. Acta Crystallogr., Sect. B: Struct. Crystallogr. Cryst. Chem. (1980) 36, 1811), gitoxigenin bisdigitoxoside ethyl acetate solvate (Go, K. et al., Acta Crystallogr., Sect. B: Struct. Sci. (1989) 45, 306), gitoxin (Go, K. et al., Acta Crystallogr., Sect. B: Struct. Crystallogr. Cryst. Chem. (1980) 36, 3034.), cerleaside-A monohydrate (Go, K. et al., Acta Crystallogr., Sect. B: Struct. Crystallogr. Cryst. Chem. (1980) 36, 3034), digitoxigenin bisdigitoxoside ethyl acetate solvate (Go, K. et al., Acta Crystallogr., Sect. B: Struct. Sci. (1989) 45, 306), ouabain octahydrate (Messerschmidt, A. Cryst. Struct. Commun. (1980) 9, 1185), 14β-hydroxy-3β-O-(L-thevetosyl)-5β-card-20(22)-enolide chloroform solvate (Fun, H.-K. et al.,. Acta Crystallogr., Sect. E: Struct. Rep. Online (2003) 59, o1694), (3β,5β,14β)-3-((2',6'-dideoxy-3',4'-O-(1'-methylethylidene)-β-D-ribo-hexopyranosyl)oxy)-14-hydroxycard-20(22)-enolide (Kihara, M. et al., (1984)), (3β,5β,14β)-3-((2',6'-dideoxy-3',4'-O-(1'-methylethylidene)-β-D-ribo-hexopyranosyl)oxy)-14-hydroxy-card-20(22)-enolide (Rohrer, D. C. et al., (1984), 106, 8269), digitoxigenin bisdigitoxoside ethyl acetate hydrate (Go, K. et al., Acta Crystallogr., Sect. B: Struct. Sci. (1989) 45, 306), 3β-O-(2',3'-O-isopropylidene-α-L-rhamnopyranosyl)-digitoxigenin (Pfeiffer, D. et al., J. Cryst. Res. and Technol. (1986) 21, 223), 14β-hydroxy-3β-O-(L-thevetosyl)-5β-card-20(22)-enolide methanol solvate hemihydrate (Chantrapromma, S. et al., Acta Crystallogr., Sect. C: Cryst. Struct. Commun. (2003) 59, o68), 3β-O-(L-2'-O-acetylhevetosyl)-14β-hydroxy-5β-card-20(22)-enolide (Chantrapromma, S. et al., Acta Crystallogr., Sect. C: Cryst. Struct. Commun. (2003), 59, o68.).

Na/K-ATPase Assays. Inhibition of $Na^+/K^+$-ATPase on HEK-293 cells and CHO-K1 cells by the library hits was determined by Aurora Biomed, Inc. using a high-throughput non-radioactive rubidium ion uptake assay. Experiments were conducted in duplicate using three different concentrations. Within each experiment, percent inhibition values at the three concentrations were expressed as the percent reduction of the maximum absorption signal observed for a 0 nM control. $IC_{50}$ values were determined using the following formula: $IC_{50}=[(50-\text{low \%})/(\text{high \%}-\text{low \%})]\times(\text{high conc.}-\text{low conc.})+\text{low conc.}$ As highlighted in FIG. 3, the requisite methoxyamine functional group was installed at the C(3) of digitoxin (the natural position of sugar attachment) in three simple chemical steps. Specifically, digitoxin was oxidized under acidic conditions to simultaneously hydrolyze the O-glycoside and provide digitoxigenone which was then converted to the corresponding set of oxime diastereomers (2a,b). Treatment of 2a,b with tert-butylamine borane resulted in a 1:1 mixture of stereoisomers which were easily resolved via standard column chromatography and assigned as 3β and 3α via X-ray crystallography. The accessibility of both digitoxigenin-like isomers 3β and 3α set the stage to explore the importance of the C(3) stereochemistry on biological activity. Pilot reactions of aglycons 3β and 3α with D-glucose were first explored in an attempt to generate the corresponding neoglycosides (FIG. 2B). Aglycons 3β and 3α reacted with D-glucose in DMF/acetic acid to form neoglycosides 4β and 4α in good yields (>70%). Both reactions proceeded stereoselectively, providing the β-anomer exclusively as determined by $^1$H NMR. An X-ray crystal structure of neoglycoside 4β was obtained (FIG. 3A) and compared to the crystal structures of related O-glycosides available from the Cambridge Crystal Database (FIG. 3B-FIG. 3D). The observed orientations about the C(2)-C(3)-N(3)-C(1') torsion (FIG. 3C) and the C(3)-N(3)-C(1')—C(2') torsion in the neoglycoside structure (FIG. 3D) fall on the periphery of the narrow range of orientations displayed in the solid state structures of 23 known cardiac O-glycosides.

A library of 78 digitoxin derivatives was synthesized in parallel from 39 reducing sugars and aglycons 3β and 3α. The reaction mixtures were stirred for two days at 40° C., concentrated, and then submitted to solid phase extraction in parallel to remove unreacted aglycon and sugar. The concentrated products were characterized by LCMS to assess purity and to confirm product identity. Even though a diverse array of reducing sugars were used—including L-sugars, deoxy sugars, dideoxy sugars, disaccharides, and uronic acids—in every case neoglycosides were successfully generated. The average purity of the library members was 91%, and the LC chromatograms suggested that ~50% of the library members contained greater than 90% of a single product isomer. While combinatorial methods have been extensively applied to steroidal derivatives and cardenolides in particular (26, 27), the results reported herein represent the largest and most diverse glycorandomized library generated to date.

The chemical stability of the neoglycosidic linkage was examined by monitoring the hydrolytic degradation of neoglycoside 4α in a 3 mM solution of 1:1 DMSO/buffer using buffers at three different pHs. Compound 4α was completely stable over the period of one month under neutral or basic conditions but slowly hydrolyzed under acidic conditions over this same time period. Using identical acidic conditions, aglycon 3α and D-glucose did not react to form neoglycoside 4α, ruling out equilibrium as a complicating factor in this analysis. Library member 27β, derived from aglycon 3β, also displayed no hydrolytic degradation under the same conditions at neutral and basic pHs, demonstrating that aglycon C(3) stereochemistry does not significantly influence neoglycoside stability. In conjunction with the neoglycoside structural analyses and the previously reported NMR and molecular dynamics studies, these hydrolytic studies suggest the neoglycoside nitrogen to be predominately charge-neutral at physiological pH.

Cytotoxicity. The activity of the library members was assessed using a high-throughput cytotoxicity assay on nine human cancer cell lines representing a broad range of carcinomas including breast, colon, CNS, liver, lung, and ovary, and a mouse mammary normal epithelial control line. The cytotoxicities of digitoxin and aglycons 3β and 3α were also examined. Digitoxin was a modest cytotoxin toward the nine human cancer cell lines (average $IC_{50}$~440 nM) but was non-specific since it affected these cancer cells with similar potency. One library member (33 µl) closely mimicked this activity. Several hits identified from the neoglycoside library exhibited enhanced activities relative to the parent natural product digitoxin (1), both in terms of potency and specificity.

The two most significant hits, library members 5β and 27β, displayed striking potency and excellent selectivity, respectively. Specifically, library member 5β was a potent cytotoxin against six cancer cell lines (18±2 nM in the case of HCT-116, greater than nine-fold more potent than digitoxin), and also was modestly selective since three out of the nine cancer cell lines tested were much less affected.

In contrast, library member 27β was a less potent cytotoxin than 5β but 27β exhibited dramatic selectivity since it was four times more cytotoxic toward NCI/ADR-RES cells ($IC_{50}$=100±10 nM) than any other cell line. This result is especially significant since NCI/ADR-RES is a multi-drug resistant line that contains high levels of MDR-1 and P-glycoprotein expression (Fairchild, C. R. et al., Cancer Res. (1987) 47, 5141-5148; Scudiero, D. A. et al., J. Natl. Cancer Inst. (1998) 90, 862). Given that cardiac glycosides are substrates for P-glycoprotein (Tanigawara, Y. et al., J. Pharmacol. Exp. Ther. (1992) 263, 840-845), such tumor specificity suggests 27β may no longer serve as a P-glycoprotein substrate or may be interacting with a unique target.

Other neoglycoside library members, while not as potent as 5β or as selective as 27β, also were significantly active. For example, library member 40β exhibited notable selectivity, with modest cytotoxicity toward only Dul45 and Hep3B cells ($IC_{50}$=200 nM±30 and 180 nM±30, respectively) while library members 15 µl and 23β were significantly more potent than digitoxin against some cell lines, but were somewhat non-selective like digitoxin.

TABLE 4

Cancer Cell Cytoxicity-Library member IC$_{50}$ values (μM) and standard errors.

| Sugar Name | | L-riboside (5β) | D-riboside (6β) | L-fucoside (7β) | D-fucoside (8β) | 2-deoxy-D-galactoside (9β) | 3-deoxy-D-glucoside (10β) | 6-deoxy-D-glucoside (11β) | 2-deoxy-2-fluoro-D-glucoside (12β) | 6-deoxy-6-fluoro-D-glucoside (13β) |
|---|---|---|---|---|---|---|---|---|---|---|
| Du145 | IC50 | 0.30 | 0.72 | 0.7 | 3.9 | 7 | 0.8 | 6 | 9 | 5 |
| | Std Err | 0.03 | 0.04 | 0.1 | 0.6 | 1 | 0.2 | 1 | 2 | 2 |
| MCF7 | IC50 | 0.19 | 3.0 | 1.3 | 11 | 5.1 | 0.46 | 1.9 | 8 | 6.2 |
| | Std Err | 0.03 | 0.4 | 0.4 | 2 | 0.8 | 0.09 | 0.2 | 1 | 0.9 |
| HCT-116 | IC50 | 0.018 | 1.3 | 1.2 | 7 | 10 | 1.8 | 2.3 | 8 | 4.8 |
| | Std Err | 0.002 | 0.6 | 0.3 | 1 | 1 | 0.4 | 0.4 | 2 | 0.8 |
| Hep 3B | IC50 | 0.059 | 0.9 | 0.35 | 4.9 | 3.6 | 1.7 | 4.4 | 8 | 4.6 |
| | Std Err | 0.006 | 0.1 | 0.04 | 0.3 | 0.8 | 0.2 | 0.4 | 1 | 1.0 |
| SF-268 | IC50 | 0.23 | 1.8 | 0.90 | 10 | 8 | 0.77 | 2.5 | 7 | 4.7 |
| | Std Err | 0.02 | 0.2 | 0.23 | 1 | 1 | 0.09 | 0.6 | 1 | 0.7 |
| SK-OV-3 | IC50 | 0.045 | 1.7 | 0.5 | 5 | 4 | 2.5 | 4 | 9 | 3.4 |
| | Std Err | 0.006 | 0.3 | 0.1 | 1 | 1 | 0.3 | 1 | 2 | 1.0 |
| NCI-H460 | IC50 | 0.053 | 0.90 | 0.6 | 1.3 | 2.0 | 1.6 | 1.0 | 2.9 | 1.4 |
| | Std Err | 0.009 | 0.05 | 0.2 | 0.3 | 0.3 | 0.1 | 0.1 | 0.4 | 0.2 |
| A549 | IC50 | 0.033 | 1.02 | 0.30 | 1.8 | 1.3 | 1.60 | 1.2 | 3.7 | 2.0 |
| | Std Err | 0.004 | 0.03 | 0.03 | 0.2 | 0.2 | 0.07 | 0.1 | 0.3 | 0.2 |
| NCI/ADR-RES | IC50 | 0.032 | 0.66 | 0.25 | 1.5 | 0.9 | 0.44 | 0.95 | 2.6 | 1.1 |
| | Std Err | 0.002 | 0.04 | 0.04 | 0.2 | 0.2 | 0.04 | 0.10 | 0.4 | 0.2 |
| NmuMG | IC50 | 0.031 | 0.48 | >25 | >25 | >25 | 0.94 | >25 | >25 | >25 |
| | Std Err | 0.007 | 0.09 | | | | 0.08 | | | |
| Du145 | IC50 | 0.30 | 0.72 | 0.7 | 3.9 | 7 | 0.8 | 6 | 9 | 5 |
| | Std Err | 0.03 | 0.04 | 0.1 | 0.6 | 1 | 0.2 | 1 | 2 | 2 |
| MCF7 | IC50 | 0.19 | 3.0 | 1.3 | 11 | 5.1 | 0.46 | 1.9 | 8 | 6.2 |
| | Std Err | 0.03 | 0.4 | 0.4 | 2 | 0.8 | 0.09 | 0.2 | 1 | 0.9 |
| HCT-116 | IC50 | 0.018 | 1.3 | 1.2 | 7 | 10 | 1.8 | 2.3 | 8 | 4.8 |
| | Std Err | 0.002 | 0.6 | 0.3 | 1 | 1 | 0.4 | 0.4 | 2 | 0.8 |
| Hep 3B | IC50 | 0.059 | 0.9 | 0.35 | 4.9 | 3.6 | 1.7 | 4.4 | 8 | 4.6 |
| | Std Err | 0.006 | 0.1 | 0.04 | 0.3 | 0.8 | 0.2 | 0.4 | 1 | 1.0 |
| SF-268 | IC50 | 0.23 | 1.8 | 0.90 | 10 | 8 | 0.77 | 2.5 | 7 | 4.7 |
| | Std Err | 0.02 | 0.2 | 0.23 | 1 | 1 | 0.09 | 0.6 | 1 | 0.7 |
| SK-OV-3 | IC50 | 0.045 | 1.7 | 0.5 | 5 | 4 | 2.5 | 4 | 9 | 3.4 |
| | Std Err | 0.006 | 0.3 | 0.1 | 1 | 1 | 0.3 | 1 | 2 | 1.0 |
| NCI-H460 | IC50 | 0.053 | 0.90 | 0.6 | 1.3 | 2.0 | 1.6 | 1.0 | 2.9 | 1.4 |
| | Std Err | 0.009 | 0.05 | 0.2 | 0.3 | 0.3 | 0.1 | 0.1 | 0.4 | 0.2 |
| A549 | IC50 | 0.033 | 1.02 | 0.30 | 1.8 | 1.3 | 1.60 | 1.2 | 3.7 | 2.0 |
| | Std Err | 0.004 | 0.03 | 0.03 | 0.2 | 0.2 | 0.07 | 0.1 | 0.3 | 0.2 |
| NCI/ADR-RES | IC50 | 0.032 | 0.66 | 0.25 | 1.5 | 0.9 | 0.44 | 0.95 | 2.6 | 1.1 |
| | Std Err | 0.002 | 0.04 | 0.04 | 0.2 | 0.2 | 0.04 | 0.10 | 0.4 | 0.2 |
| NmuMG | IC50 | 0.031 | 0.48 | >25 | >25 | >25 | 0.94 | >25 | >25 | >25 |
| | Std Err | 0.007 | 0.09 | | | | 0.08 | | | |

| Sugar Name | | L-lyxoside (14β) | D-lyxoside (15β) | L-rhamnoside (16β) | L-alloside (17β) | D-alloside (18β) | L-altroside (19β) | D-altroside (20β) | L-galactoside (21β) | D-galactoside (22β) |
|---|---|---|---|---|---|---|---|---|---|---|
| Du145 | IC50 | 2.4 | 0.07 | 0.17 | 0.79 | 2.2 | 2.1 | 1.2 | 2.1 | 1.5 |
| | Std Err | 0.5 | 0.02 | 0.03 | 0.07 | 0.2 | 0.3 | 0.3 | 0.2 | 0.1 |
| MCF7 | IC50 | 4.5 | 0.23 | 1.8 | 0.9 | 6.8 | 1.3 | 1.5 | 1.8 | 3.0 |
| | Std Err | 0.9 | 0.02 | 0.2 | 0.1 | 0.8 | 0.3 | 0.2 | 0.3 | 0.4 |
| HCT-116 | IC50 | 8 | 0.17 | 0.9 | 0.5 | 6 | 1.1 | 1.1 | 2.1 | 1.8 |
| | Std Err | 2 | 0.03 | 0.3 | 0.2 | 1 | 0.3 | 0.2 | 0.3 | 0.5 |
| Hep 3B | IC50 | 0.6 | 0.09 | 0.54 | 0.8 | 3.3 | 2.0 | 0.35 | 1.3 | 0.6 |
| | Std Err | 0.1 | 0.01 | 0.07 | 0.1 | 0.6 | 0.4 | 0.04 | 0.2 | 0.3 |
| SF-268 | IC50 | 1.1 | 0.09 | 3.3 | 0.4 | 3.5 | 1.2 | 1.1 | 1.4 | 1.2 |
| | Std Err | 0.4 | 0.01 | 0.5 | 0.1 | 0.6 | 0.2 | 0.2 | 0.2 | 0.2 |
| SK-OV-3 | IC50 | 4.2 | 0.16 | 4 | 0.7 | 6.4 | 1.0 | 1.1 | 1.6 | 1.5 |
| | Std Err | 0.8 | 0.08 | 1 | 0.1 | 1.0 | 0.2 | 0.2 | 0.5 | 0.5 |
| NCI-H460 | IC50 | 5 | 0.09 | 0.33 | 0.69 | 3.2 | 1.6 | 0.62 | 2.6 | 1.6 |
| | Std Err | 1 | 0.01 | 0.05 | 0.09 | 0.2 | 0.2 | 0.09 | 0.2 | 0.2 |
| A549 | IC50 | 0.70 | 0.14 | 0.7 | 0.24 | 2.0 | 0.76 | 0.54 | 0.9 | 0.97 |
| | Std Err | 0.06 | 0.02 | 0.1 | 0.02 | 0.2 | 0.09 | 0.04 | 0.2 | 0.09 |
| NCI/ADR-RES | IC50 | 0.73 | 0.075 | 0.35 | 0.16 | 0.8 | 0.41 | 0.9 | 1.6 | 0.8 |
| | Std Err | 0.04 | 0.005 | 0.02 | 0.01 | 0.2 | 0.05 | 0.1 | 0.5 | 0.1 |

TABLE 4-continued

Cancer Cell Cytoxicity-Library member IC$_{50}$ values (µM) and standard errors.

| | | | | | | | | | |
|---|---|---|---|---|---|---|---|---|---|
| NmuMG | IC50 | 0.9 | 0.069 | >25 | 0.33 | 3.1 | 1.0 | 0.9 | 1.0 | 1.5 |
| | Std Err | 0.1 | 0.005 | | 0.04 | 0.5 | 0.2 | 0.2 | 0.2 | 0.2 |

| Sugar Name | | L-xyloside (23β) | D-xyloside (24β) | D-guloside (25β) | L-mannoside (26β) | D-mannoside (27β) | L-idoside (28β) | D-idoside (29β) | L-mycaroside (30β) | 6-keto-D-galactoside (31β) |
|---|---|---|---|---|---|---|---|---|---|---|
| Du145 | IC50 | 0.62 | 0.82 | 5.7 | 2.0 | 1.3 | 1.9 | 1.3 | 1.1 | 1.5 |
| | Std Err | 0.07 | 0.06 | 0.8 | 0.4 | 0.3 | 0.4 | 0.2 | 0.2 | 0.3 |
| MCF7 | IC50 | 0.23 | 1.8 | 0.9 | 3.0 | 1.7 | 2.6 | 0.44 | 1.8 | 9 |
| | Std Err | 0.02 | 0.6 | 0.3 | 0.4 | 0.2 | 0.4 | 0.07 | 0.3 | 2 |
| HCT-116 | IC50 | 0.10 | 1.8 | 2.1 | 4.2 | 0.8 | 3.2 | 2.3 | 0.6 | 3.1 |
| | Std Err | 0.03 | 0.3 | 0.4 | 0.7 | 0.2 | 0.6 | 0.3 | 0.1 | 0.8 |
| Hep 3B | IC50 | 0.50 | 1.2 | 1.9 | 2.0 | 0.4 | 1.0 | 0.3 | 0.6 | 3.1 |
| | Std Err | 0.08 | 0.1 | 0.2 | 0.3 | 0.1 | 0.1 | 0.1 | 0.2 | 0.6 |
| SF-268 | IC50 | 0.49 | 2.1 | 2.0 | 2.1 | 2.2 | 2.1 | 1.3 | 1.1 | 8 |
| | Std Err | 0.09 | 0.4 | 0.5 | 0.4 | 0.4 | 0.3 | 0.3 | 0.2 | 3 |
| SK-OV-3 | IC50 | 0.22 | 1.8 | 2.2 | 3.1 | 0.8 | 2.4 | 1.5 | 1.1 | 2.9 |
| | Std Err | 0.04 | 0.4 | 1.0 | 0.8 | 0.2 | 0.5 | 0.3 | 0.2 | 0.3 |
| NCI-H460 | IC50 | 0.08 | 1.8 | 2.6 | 1.6 | 0.7 | 1.3 | 1.3 | 0.19 | 2.4 |
| | Std Err | 0.02 | 0.1 | 0.2 | 0.2 | 0.1 | 0.2 | 0.2 | 0.02 | 0.6 |
| A549 | IC50 | 0.079 | 1.1 | 2.0 | 1.7 | 0.63 | 1.14 | 0.37 | 0.6 | 2.3 |
| | Std Err | 0.005 | 0.2 | 0.4 | 0.2 | 0.07 | 0.08 | 0.02 | 0.1 | 0.9 |
| NCI/ADR-RES | IC50 | 0.138 | 0.54 | 1.1 | 4.8 | 0.10 | 0.61 | 1.5 | 0.35 | 1.0 |
| | Std Err | 0.009 | 0.04 | 0.3 | 0.5 | 0.01 | 0.06 | 0.4 | 0.03 | 0.1 |
| NmuMG | IC50 | 0.057 | 0.9 | 1.8 | 1.3 | 1.0 | 1.8 | >25 | >25 | >25 |
| | Std Err | 0.007 | 0.1 | 0.3 | 0.2 | 0.1 | 0.5 | | | |

| Sugar Name | | L-arabinoside (32β) | D-arabinoside (33β) | N-acetyl-D-galactosaminoside (34β) | melibioside (35β) | lactoside (36β) | maltoside (37β) | D-galacturonoside (38β) | L-taloside (39β) |
|---|---|---|---|---|---|---|---|---|---|
| Du145 | IC50 | 1.1 | 0.17 | >25 | 27 | 13 | 4.4 | 1.9 | 0.76 |
| | Std Err | 0.3 | 0.03 | | 4 | 3 | 1.0 | 0.4 | 0.07 |
| MCF7 | IC50 | 2.2 | 0.30 | >25 | >25 | >25 | >25 | 5 | 1.8 |
| | Std Err | 0.3 | 0.04 | | | | | 2 | 0.3 |
| HCT-116 | IC50 | 0.3 | 0.36 | >25 | >25 | >25 | 24 | 2.7 | 2.3 |
| | Std Err | 0.1 | 0.07 | | | | 6 | 0.6 | 0.4 |
| Hep 3B | IC50 | 1.2 | 0.26 | 17 | 26 | 26 | 7 | 2.1 | 0.96 |
| | Std Err | 0.1 | 0.04 | 2 | 6 | 4 | 2 | 0.3 | 0.07 |
| SF-268 | IC50 | 1.0 | 0.16 | >25 | >25 | >25 | 6 | 2.2 | 1.4 |
| | Std Err | 0.3 | 0.03 | | | | 1 | 0.7 | 0.2 |
| SK-OV-3 | IC50 | 3.0 | 0.47 | 17 | 15 | 19 | 5 | 3.1 | 1.5 |
| | Std Err | 0.5 | 0.09 | 4 | 2 | 4 | 1 | 0.9 | 0.5 |
| NCI-H460 | IC50 | 0.72 | 0.33 | 20 | 29 | >25 | 6.1 | 1.4 | 1.1 |
| | Std Err | 0.07 | 0.04 | 2 | 8 | | 0.9 | 0.2 | 0.1 |
| A549 | IC50 | 1.7 | 0.34 | >25 | >25 | 24 | 4.4 | 2.2 | 0.89 |
| | Std Err | 0.3 | 0.05 | | | 4 | 0.2 | 0.2 | 0.07 |
| NCI/ADR-RES | IC50 | 0.65 | 0.124 | 6.4 | 16 | 13 | 4.4 | 1.6 | 1.0 |
| | Std Err | 0.05 | 0.007 | 0.5 | 1 | 2 | 0.4 | 0.1 | 0.3 |
| NmuMG | IC50 | 0.4 | 0.12 | >25 | >25 | >25 | >25 | >25 | 0.5 |
| | Std Err | 0.1 | 0.02 | | | | | | 0.2 |

| Sugar Name | | D-taloside (40β) | 6-deoxy-6-azido-D-mannoside (41β) | L-glucoside (42β) | D-glucoside (4β) | O-D-glucoside (43β) | R-C(3) aglycon (3β) | S-C(3) aglycon (3α) | digitoxin (1) |
|---|---|---|---|---|---|---|---|---|---|
| Du145 | IC50 | 0.20 | 2.0 | 1.3 | 8.2 | 0.22 | 1.3 | 2.9 | 0.26 |
| | Std Err | 0.03 | 0.7 | 0.3 | 0.9 | 0.04 | 0.3 | 0.9 | 0.03 |
| MCF7 | IC50 | 1.4 | 3.3 | 0.6 | 10 | 0.7 | 1.8 | 13 | 0.32 |
| | Std Err | 0.3 | 0.6 | 0.3 | 1 | 0.1 | 0.3 | 2 | 0.03 |
| HCT-116 | IC50 | 1.9 | 6 | 0.9 | 3.8 | 0.6 | 1.2 | 9 | 0.17 |
| | Std Err | 0.2 | 1 | 0.4 | 0.7 | 0.1 | 0.2 | 2 | 0.04 |
| Hep 3B | IC50 | 0.18 | 1.8 | 0.9 | 2.4 | 0.21 | 1.4 | 3.5 | 0.22 |
| | Std Err | 0.03 | 0.3 | 0.2 | 0.3 | 0.03 | 0.1 | 0.3 | 0.01 |
| SF-268 | IC50 | 1.3 | 2.5 | 1.9 | 4.5 | 0.22 | 1.0 | 3.5 | 1.5 |
| | Std Err | 0.1 | 0.6 | 0.3 | 0.8 | 0.08 | 0.2 | 0.5 | 0.2 |
| SK-OV-3 | IC50 | 0.49 | 2.1 | 1.0 | 6 | 0.40 | 0.9 | 3 | 0.7 |
| | Std Err | 0.09 | 0.3 | 0.4 | 1 | 0.08 | 0.2 | 1 | 0.1 |
| NCI-H460 | IC50 | 0.80 | 2.7 | 1.3 | 3.5 | 0.39 | 0.7 | 2.4 | 0.28 |
| | Std Err | 0.06 | 0.3 | 0.1 | 0.5 | 0.05 | 0.1 | 0.2 | 0.03 |
| A549 | IC50 | 0.41 | 1.7 | 0.8 | 2.9 | 0.29 | 1.2 | 8.3 | 0.28 |
| | Std Err | 0.03 | 0.1 | 0.2 | 0.3 | 0.02 | 0.1 | 0.5 | 0.04 |
| NCI/ADR-RES | IC50 | 1.9 | 0.84 | 0.55 | 1.9 | 0.19 | 0.71 | 5.1 | 0.22 |
| | Std Err | 0.5 | 0.09 | 0.05 | 0.5 | 0.02 | 0.05 | 0.6 | 0.03 |

TABLE 4-continued

Cancer Cell Cytoxicity-Library member IC$_{50}$ values (μM) and standard errors.

| | | | | | | | | | |
|---|---|---|---|---|---|---|---|---|---|
| NmuMG | IC50 | 0.48 | >25 | 1.2 | 3.1 | >25 | >25 | >25 | >25 |
| | Std Err | 0.06 | | 0.1 | 0.2 | | | | |

| Sugar Name | | L-riboside (5α) | D-riboside (6α) | L-fucoside (7α) | D-fucoside (8α) | 2-deoxy-D-galactoside (9α) | 3-deoxy-D-glucoside (10α) | 6-deoxy-D-glucoside (11α) | 2-deoxy-2-fluoro-D-glucoside (12α) | 6-deoxy-6-fluoro-D-glucoside (13α) |
|---|---|---|---|---|---|---|---|---|---|---|
| Du145 | IC50 | >25 | >25 | >25 | >25 | >25 | >25 | >25 | >25 | >25 |
| | Std Err | | | | | | | | | |
| MCF7 | IC50 | >25 | >25 | >25 | >25 | >25 | >25 | >25 | >25 | >25 |
| | Std Err | | | | | | | | | |
| HCT-116 | IC50 | >25 | >25 | >25 | >25 | >25 | >25 | >25 | >25 | >25 |
| | Std Err | | | | | | | | | |
| Hep 3B | IC50 | >25 | >25 | >25 | >25 | >25 | >25 | >25 | >25 | >25 |
| | Std Err | | | | | | | | | |
| SF-268 | IC50 | >25 | >25 | >25 | >25 | >25 | >25 | >25 | >25 | >25 |
| | Std Err | | | | | | | | | |
| SK-OV-3 | IC50 | >25 | >25 | >25 | >25 | >25 | >25 | >25 | >25 | >25 |
| | Std Err | | | | | | | | | |
| NCI-H460 | IC50 | >25 | >25 | >25 | >25 | >25 | >25 | >25 | >25 | >25 |
| | Std Err | | | | | | | | | |
| A549 | IC50 | >25 | >25 | >25 | >25 | >25 | >25 | >25 | >25 | >25 |
| | Std Err | | | | | | | | | |
| NCI/ADR-RES | IC50 | >25 | >25 | >25 | >25 | >25 | >25 | >25 | >25 | >25 |
| | Std Err | | | | | | | | | |
| NmuMG | IC50 | >25 | >25 | >25 | >25 | >25 | >25 | >25 | >25 | >25 |
| | Std Err | | | | | | | | | |

| Sugar Name | | L-lyxoside (14α) | D-lyxoside (15α) | L-rhamnoside (16α) | L-alloside (17α) | D-alloside (18α) | L-altroside (19α) | D-altroside (20α) | L-galactoside (21α) | D-galactoside (22α) |
|---|---|---|---|---|---|---|---|---|---|---|
| Du145 | IC50 | >25 | >25 | >25 | >25 | >25 | >25 | >25 | >25 | >25 |
| | Std Err | | | | | | | | | |
| MCF7 | IC50 | >25 | >25 | >25 | >25 | >25 | >25 | >25 | >25 | >25 |
| | Std Err | | | | | | | | | |
| HCT-116 | IC50 | >25 | >25 | >25 | >25 | >25 | >25 | >25 | >25 | >25 |
| | Std Err | | | | | | | | | |
| Hep 3B | IC50 | >25 | >25 | >25 | >25 | >25 | >25 | >25 | >25 | >25 |
| | Std Err | | | | | | | | | |
| SF-268 | IC50 | >25 | >25 | >25 | >25 | >25 | >25 | >25 | >25 | >25 |
| | Std Err | | | | | | | | | |
| SK-OV-3 | IC50 | >25 | >25 | >25 | >25 | >25 | >25 | >25 | >25 | >25 |
| | Std Err | | | | | | | | | |
| NCI-H460 | IC50 | >25 | >25 | >25 | >25 | >25 | >25 | >25 | >25 | >25 |
| | Std Err | | | | | | | | | |
| A549 | IC50 | >25 | >25 | >25 | >25 | >25 | >25 | >25 | >25 | >25 |
| | Std Err | | | | | | | | | |
| NCI/ADR-RES | IC50 | >25 | >25 | >25 | >25 | >25 | >25 | >25 | >25 | >25 |
| | Std Err | | | | | | | | | |
| NmuMG | IC50 | >25 | >25 | >25 | >25 | >25 | >25 | >25 | >25 | >25 |
| | Std Err | | | | | | | | | |

| Sugar Name | | L-xyloside (23α) | D-xyloside (24α) | D-guloside (25α) | L-mannoside (26α) | D-mannoside (27α) | L-idoside (28α) | D-idoside (29α) | L-mycaroside (30α) | 6-keto-D-galactoside (31α) |
|---|---|---|---|---|---|---|---|---|---|---|
| Du145 | IC50 | >25 | >25 | >25 | >25 | >25 | >25 | >25 | >25 | >25 |
| | Std Err | | | | | | | | | |
| MCF7 | IC50 | >25 | >25 | >25 | >25 | >25 | >25 | >25 | >25 | >25 |
| | Std Err | | | | | | | | | |
| HCT-116 | IC50 | >25 | >25 | >25 | >25 | >25 | >25 | >25 | >25 | >25 |
| | Std Err | | | | | | | | | |
| Hep 3B | IC50 | >25 | >25 | >25 | >25 | >25 | >25 | >25 | >25 | >25 |
| | Std Err | | | | | | | | | |
| SF-268 | IC50 | >25 | >25 | >25 | >25 | >25 | >25 | >25 | >25 | >25 |
| | Std Err | | | | | | | | | |
| SK-OV-3 | IC50 | >25 | >25 | >25 | >25 | >25 | >25 | >25 | >25 | >25 |
| | Std Err | | | | | | | | | |
| NCI-H460 | IC50 | >25 | >25 | >25 | >25 | >25 | >25 | >25 | >25 | >25 |
| | Std Err | | | | | | | | | |
| A549 | IC50 | >25 | >25 | >25 | >25 | >25 | >25 | >25 | >25 | >25 |
| | Std Err | | | | | | | | | |
| NCI/ADR-RES | IC50 | >25 | >25 | >25 | >25 | >25 | >25 | >25 | >25 | >25 |
| | Std Err | | | | | | | | | |

TABLE 4-continued

Cancer Cell Cytoxicity-Library member IC$_{50}$ values (µM) and standard errors.

| | | | | | | | | | |
|---|---|---|---|---|---|---|---|---|---|
| NmuMG | IC50 | >25 | >25 | >25 | >25 | >25 | >25 | >25 | >25 |
| | Std Err | | | | | | | | |

| Sugar Name | | L-arabinoside (32α) | D-arabinoside (33α) | N-acetyl-D-galactosaminoside (34α) | melibioside (35α) | lactoside (36α) | maltoside (37α) | D-galacturonoside (38α) | L-taloside (39α) |
|---|---|---|---|---|---|---|---|---|---|
| Du145 | IC50 | >25 | >25 | >25 | >25 | >25 | >25 | >25 | >25 |
| | Std Err | | | | | | | | |
| MCF7 | IC50 | >25 | >25 | >25 | >25 | >25 | >25 | >25 | >25 |
| | Std Err | | | | | | | | |
| HCT-116 | IC50 | >25 | >25 | >25 | >25 | >25 | >25 | >25 | >25 |
| | Std Err | | | | | | | | |
| Hep 3B | IC50 | >25 | >25 | >25 | >25 | >25 | >25 | >25 | >25 |
| | Std Err | | | | | | | | |
| SF-268 | IC50 | >25 | >25 | >25 | >25 | >25 | >25 | >25 | >25 |
| | Std Err | | | | | | | | |
| SK-OV-3 | IC50 | >25 | >25 | >25 | >25 | >25 | >25 | >25 | >25 |
| | Std Err | | | | | | | | |
| NCI-H460 | IC50 | >25 | >25 | >25 | >25 | >25 | >25 | >25 | >25 |
| | Std Err | | | | | | | | |
| A549 | IC50 | >25 | >25 | >25 | >25 | >25 | >25 | >25 | >25 |
| | Std Err | | | | | | | | |
| NCI/ADR-RES | IC50 | >25 | >25 | >25 | >25 | >25 | >25 | >25 | >25 |
| | Std Err | | | | | | | | |
| NmuMG | IC50 | >25 | >25 | >25 | >25 | >25 | >25 | >25 | >25 |
| | Std Err | | | | | | | | |

| Sugar Name | | D-taloside (40α) | 6-deoxy-6-azido-D-mannoside (41α) | L-glucoside (42α) | D-glucoside (4α) |
|---|---|---|---|---|---|
| Du145 | IC50 | >25 | >25 | >25 | >25 |
| | Std Err | | | | |
| MCF7 | IC50 | >25 | >25 | >25 | >25 |
| | Std Err | | | | |
| HCT-116 | IC50 | >25 | >25 | >25 | >25 |
| | Std Err | | | | |
| Hep 3B | IC50 | >25 | >25 | >25 | >25 |
| | Std Err | | | | |
| SF-268 | IC50 | >25 | >25 | >25 | >25 |
| | Std Err | | | | |
| SK-OV-3 | IC50 | >25 | >25 | >25 | >25 |
| | Std Err | | | | |
| NCI-H460 | IC50 | >25 | >25 | >25 | >25 |
| | Std Err | | | | |
| A549 | IC50 | >25 | >25 | >25 | >25 |
| | Std Err | | | | |
| NCI/ADR-RES | IC50 | >25 | >25 | >25 | >25 |
| | Std Err | | | | |
| NmuMG | IC50 | >25 | >25 | >25 | >25 |
| | Std Err | | | | |

The library members showed stereospecificity in the cytotoxic actions. In contrast to the 3β-derived analogs, the 38 neoglycosides derived from aglycon 3α uniformly displayed low cytotoxicities in the assay (IC$_{50}$>25 µM), as did aglycon 3α itself, establishing the importance of the natural β configuration of the C(3) stereocenter. Aglycon 3β was only weakly cytotoxic against the cell lines (average IC$_{50}$~1.10 µM), consistent with the influence sugars have upon library member cytotoxicity. Interestingly, the six hits described above all contain sugars with a common structural feature, an S-configured C(2') sugar stereocenter. This C(2') stereochemistry appears to be of critical importance for compound activity. For example, the C(2') epimer of the extremely potent library member 5β (L-arabinose-containing member 32β) was relatively inactive toward the ten cell lines examined. Likewise, D-glucose-containing library member 4β was relatively inactive and displayed none of the cell line specificity observed for its C(2') epimer 27β.

Neoglycosides with sugars containing reactive handles were successfully generated. For example, while not active under these assay conditions, 41β contains the C(2') stereochemistry shared by the library hits and a reactive azido group which is amenable to further diversification via Huisgen 1,3-dipolar cycloaddition (Fu, X. et al., Nat. Biotechnol. (2003) 21, 1467-1469). Such library members can this serve as the starting point for the development of compounds with enhanced cytotoxicity.

To assess how these structural modifications impact the ability of library members to inhibit Na$^+$/K$^+$-ATPases, a fundamental activity of cardiac glycosides (Paula, S., et al., (2005) Biochemistry 44, 498-510), library hits 5β, 15β, 23β, 27β, 33β, 40β, and digitoxin (1) were submitted to a nonradioactive rubidium uptake assay to gauge Na$^+$/K$^+$-ATPase inhibition in both HEK-239 human embryonic kidney cells and CHO-K1 hamster ovary cells (Gill, S. et al., (2004) ASSAY and Drug Development Technologies 2, 535-542). In HEK-239 cells, digitoxin displayed an $IC_{50}$ of 75.4±0.5 µM, while none of the library hits showed 50% inhibition even at the highest concentration tested (300 µM for 5β, 15β, 23β, and 33β; 200 µM for 27β and 40β). A similar trend was observed in the CHO-K1 cells. Thus, hits identified from the neoglycoside library not only displayed enhanced cytotoxic properties toward human cancer cells, but the rubidium uptake assays reveal these six neoglycosides to be less potent $Na^+/K^+$-ATPase inhibitors in a human cell line than digitoxin.

present study reveals a new class of desirable non-cardioactive tumor-specific and potent cytotoxins, the mechanism of which remains to be elucidated.

The neoglycorandomization of digitoxin illustrates the remarkable ease by which the influence a sugar has on a natural product scaffold can be quickly scanned via this simple, mild, and robust reaction with unprotected and non-activated reducing sugars. In this prototype example, it is clear that subtle sugar modifications can dramatically, and independently, modulate both the cytotoxic properties and the $Na^+/K^+$-ATPase inhibitory properties of cardiac glycosides. The potential of neoglycorandomization is further augmented by its compatibility with chemical handles (e.g., azido groups) for additional elaboration. Neoglycorandomization is solely limited by the efficiency and specificity of alkoxyamine handle installation and the availability of reducing sugar donors; thus, these studies highlight the unique potential of neoglycosylation and/or neoglycorandomization as a universally powerful tool for glycobiology and drug discovery. Moreover, a wide Tange of reducing sugars are available commercially or via elegant transformations from simple precursors, presenting broad access to the only building blocks essential to this approach.

TABLE 5

$Na^+/K^+$-ATPase Inhibition $IC_{50}$ values (µM) and standard deviations.

| Library Member | | digitoxin (1) | L-riboside (5β) | D-lyxoside (15β) | L-xyloside (23β) | D-mannoside (27β) | D-arabinoside (33β) | D-taloside (40β) |
|---|---|---|---|---|---|---|---|---|
| HEK-298 | IC50 | 75.4 | >300 | >300 | >300 | >200 | >300 | >200 |
| | Std Dev | 0.5 | | | | | | |
| CHO-K1 | IC50 | 77 | 270 | 200 | >500 | >300 | 170 | 180 |
| | Std Dev | 2 | 20 | 10 | | | 50 | 30 |

The growing body of epidemiological (Johnson, P. H. et al., Molecular Cancer Therapeutics (2002) 1, 1293-1304), in vitro (Johansson, S. et al., Anti-Cancer Drugs (2001) 12, 475-483) and in vivo (Svensson, A. et al., Anticancer Res. (2005) 25, 207-212) evidence supporting the anti-cancer benefits of cardinolides has prompted the search for non-cardio-active analogs which still retain anticancer activity. The specific mechanism of cardenolide-induced cytotoxicity remains controversial. For example, a preferred ligand for cardenolides, the $Na^+/K^+$-ATPase, belongs to the '$Na^+/K^+$-ATPase signalosome' the activation of which by certain cardenolides can lead to NF-κB pathway inactivation (Dmitrieva, R. I. et al. Exp. Biol. Med. (2002) 227, 561-569). Constitutive activation of the NF-κB pathway protects a large group of cancer cells against apoptosis while suppression of this transcription factor can restore normal levels of apoptosis in cancer cells and also potentially block tumorigenesis and inflammation (Quanquebeke E. V. et al. J. Med. Chem. (2005) 48, 849-856; Sreenivasan, Y. et al., Biochem. Pharmacol. (2003) 66, 2223-2239). Yet, digitoxin-mediated inhibition of the NF-κB signaling pathway in CF lung epithelial cells has been demonstrated to be mechanistically distinct from $Na^+/K^+$-ATPase inhibition (Srivastava, M. et. al., (2004)). With respect to other implicated cellular players, the same nonlethal cardenolide concentrations that inhibit breast cancer cell proliferation also activates Src kinase, stimulates the interaction between $Na^+/K^+$-ATPase, the activated Src kinase and epidermal growth factor (EGFR), and leads to the activation of extracellular signal-regulated kinases 1 and 2 (ERK1/2) and subsequent cell cycle arrest caused by increased levels of p21$^{Cip1}$ (Kometiani, P. et al., Mol. Pharmacol. (2005) 67, 929-936). Cardiac glycosides have also been demonstrated to initiate apoptosis via the classical caspase-dependent pathways in malignant T lymphoblasts (Daniel, D. et al., Internatl. Immunopharmacol. (2003) 3, 1791-1801) and prostrate cancer cells (Lin, H. et al., J. Biol. Chem. (2004) 279, 29302-29307) and, in the latter, also inhibit testosterone production in vivo (Lin, H. et al. Br. J. Pharmacol. (1998) 125, 1635-1640). Thus, while the cytotoxicity of certain cardiac glycosides may correlate with $Na^+/K^+$-ATPase inhibition, the The versatility of the present invention is further demonstrated by modifying glycosidic linkage in digitoxin analogs for tumor selective cytotoxins. Scheme 7 illustrates neoglycosylation, the afore-mentioned chemoselective reaction between secondary oxyamines and unprotected, unactivated reducing sugars to form stable "neoglycosides." Peri, F. et al., Tetrahedron (1998) 54, 12269-12278.

Scheme 7

The method of the present invention provides broad access to a wide range of oxyamines for synthesizing a variety of neoglycosides. In this scheme, the inventor used commercially available salt, $HONH_2$*HCl, and treated it with $Boc_2O$ to generate HONHBoc (see Cardilo, G. et al., Tetrahedron (1998) 54, 8217-8222). Under basic conditions, HONHBoc was treated with primary or secondary alkyl halides to form protected oxiamines (RONHBoc) (based on Weinstock, L. T. and C. C. Cheng, J. Med. Chem. (1979) 22, 594-597). These oximanines were deprotected quantitatively using 4M HCl in dioxane to provide the primary oxyamines employed to synthesize the alglycons used in the neoglycosylation scheme shown below:

HONH₂*HCl (1) →[Boc₂O, NaHCO₃ / CH₂Cl₂/H₂O] HONHBoc (2) →[RBr / NaOH / 70% EtOH] RONHBoc (3) →[4 M HCl/diox.] RONH₃Cl (4)

digitoxin (1)

Reagents:
1. CrO₃, H₂SO₄, acetone, H₂O
2. RONH₂*HCl, pyr, MeOH
3. tBuNH₂*BH₃, 10% aq. HCl, EtOH secondary oxyamine 2a: R = Me
2b: R = Et
2c: R = iPr
2d: R = tBu
2e: R = allyl
2f: R = Bn
2g: R = Pr
2h: R = sBu
2i: R = cyclopent.
2j: R = cyclohex.

"oxyamine neoglycosylation"
L-ribose or L-xylose
MeOH/CHCl₃
AcOH (1 eq.)
40° C.

neoglycoside

| L-ribose | L-xylose |
|---|---|
| 3a: R = Me | 4a: R = Me |
| 3b: R = Et | 4b: R = Et |
| 3c: R = iPr | 4c: R = iPr |
| 3d: R = tBu | 4d: R = tBu |
| 3e: R = allyl | 4e: R = allyl |
| 3f: R = Bn | 4f: R = Bn |
| 3g: R = Pr | 4g: R = Pr |
| 3h: R = sBu | 4h: R = sBu |
| 3i: R = cyclopent. | 4i: R = cyclopent. |
| 3j: R = cyclohex. | 4j: R = cyclohex. |

This method has provided glycopeptide mimics, (Carrasco, M. R. et al., Biopolymers (2006) 84, 414-420; Carrasco, M. R. et al., J. Org. Chem., (2003) 68, 8853-8858; Carrasco, M. R. et al., J. Org. Chem., (2003) 68, 195-197; Carrasco, M. R. et al., Tetrahedron Lett., (2002) 43, 5727-5729) oligosaccharide mimics, (Peri, F. et al., Chem. Comm. (2004) 623-627; Peri, F. et al., Chem. Eur. J. (2004) 10, 1433-1444) and large libraries of natural product MeON-neoglycosides including potent digitoxin-based cytotoxins (e.g., 3a, $IC_{50=18}$-59 nM) (described herein; Langenhan, J. M. et al., Proc. Natl. Acad. Sci. (2005) 102, 12305-12310). Since digitoxin neoglycosides containing a non-natural MeON-linkage displayed strong cytotoxicity, the inventor suspected tuning the structure of such glycosidic linkages would modulate glycoconjugate activities. Testing this hypothesis required the development of oxyamine neoglycosylation to provide other RON-linkages.

To determine if neoglycosides with alternative linkages can be generated easily, aglycons 2 were synthesized from digitoxin in three simple steps and incubated in parallel with L-ribose and L-xylose, deoxysugars that previously produced cytotoxic digitoxin neoglycosides (Langenhan, J. M. et al., J. S. Proc. Natl. Acad. Sci. (2005) 102, 12305-12310.)

Some of the syntheses and data reported below were previously reported in Langenhan, J. M. et al., Bioorg. Med. Chem. Lett. (2008) 18, 670-673, which is incorporated by reference herein in its entirety for all purposes. Under the optimized reaction conditions indicated in Scheme 7, all digitoxin aglycons containing non-methyl O-alkyl groups except for 2d (R=tBu) were compatible with oxyamine neoglycosylation, leading to a panel of eighteeen digitoxin analogs (3a-c,e-j and 4a-c,e-j) containing different RON-glycosidic linkages. The panel was purified in parallel via solid phase extraction on silica gel cartridges to remove unreacted aglycon and sugar, and LCMS was used to confirm product identity and assess product purity. Similar to previous results with MeON-glycosides, the average purity of the panel of neoglycosides was 87%, and all but one compound (3b) contained greater than 90% of a single product isomer. The isolated yields for these reactions ranged from 7 to 61% (average 30%). Therefore, this represents the first panel of natural products that contain diversified neoglycosidic linkages.

Regarding the use of tert-butyl oxyamines (2d), for molecules with "secondary" sites of nitrogen attachment, like digitoxin (carbon a to nitrogen is attached to two carbons and one proton), the reactions do not work when the R portion of the NOR group is doubly branched alpha to oxygen (e.g., t-Bu), and the failure of t-Bu in the digitoxin context was expected. In contrast, previously performed model reactions showed that all oxyamines tried work on systems that contain a "primary" site of nitrogen attachment (carbon a to nitrogen is attached to one carbon and two protons). The model reactions and the resulting LC/MS-confirmed data for % conversion are shown below.

Effect of Aglycon Structure on Percent Conversion of Glycosylation

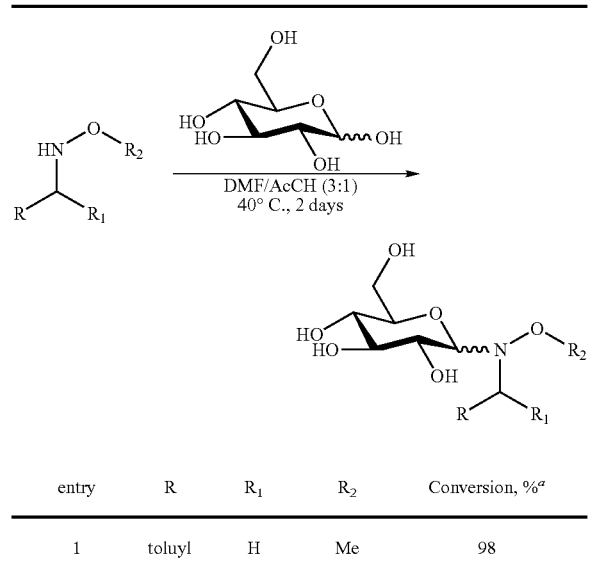

| entry | R | $R_1$ | $R_2$ | Conversion, %$^a$ |
|---|---|---|---|---|
| 1 | toluyl | H | Me | 98 |
| 2 | toluyl | H | Et | 98 |

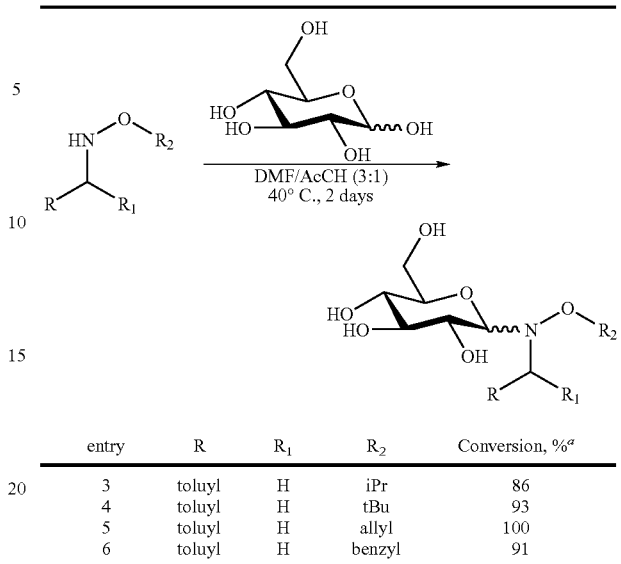

| entry | R | $R_1$ | $R_2$ | Conversion, %$^a$ |
|---|---|---|---|---|
| 3 | toluyl | H | iPr | 86 |
| 4 | toluyl | H | tBu | 93 |
| 5 | toluyl | H | allyl | 100 |
| 6 | toluyl | H | benzyl | 91 |

Figure 7:
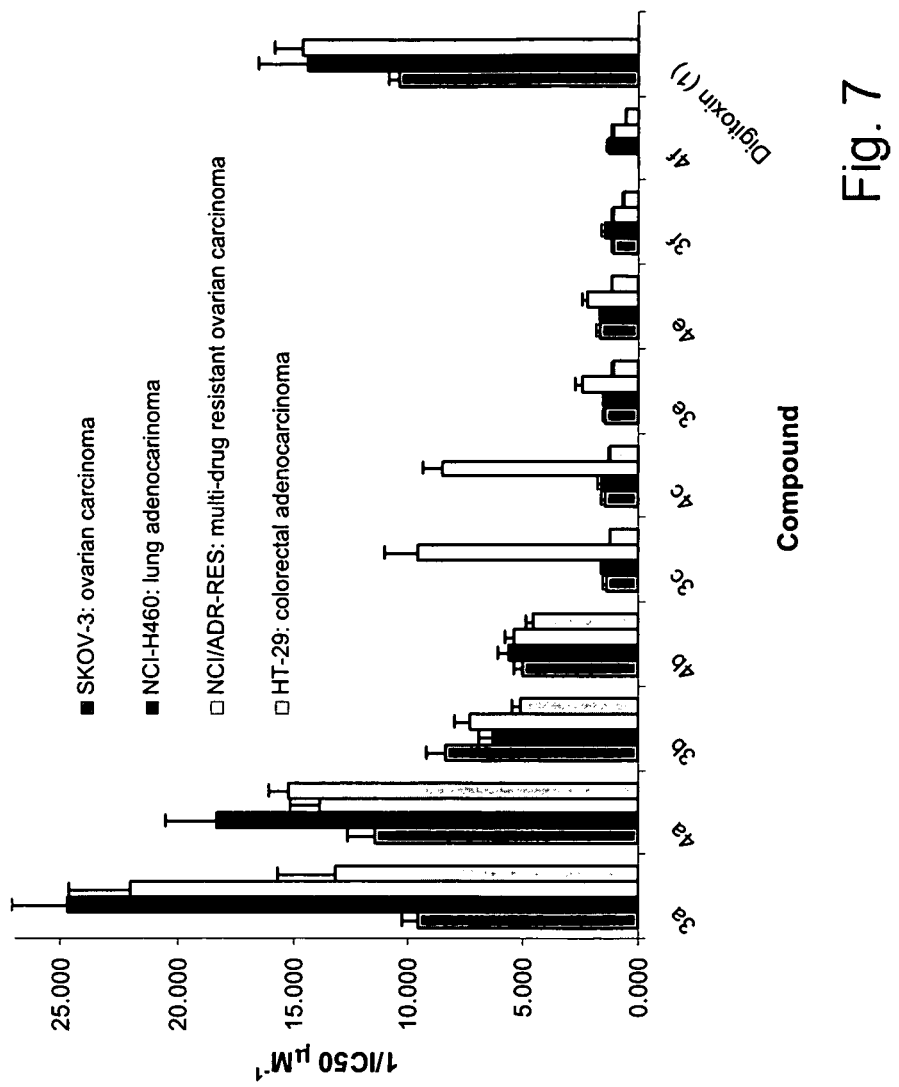
FIG. 7 is a graphical summary of the results of the $IC_{50}$ data from cytotoxicity assays. Reciprocal $IC_{50}$ values are displayed for clarity; standard errors are depicted with error bars. In the assay, live cells are quantified by measuring the luminescent signal resulting from the reaction between cellular ATP and luciferin to form oxyluciferin. The $IC_{50}$ value for each compound represents at least four replicates of dose-response experiments conducted over six concentrations at two-fold dilutions.

The anticancer activities of ten panel analogues (3a-c,e,f and 4a-c,e,f) and digitoxin (1) were assessed using a high-throughput cytotoxicity assay on four human cancer cell lines, (FIG. 7) representing lung, colorectal, and ovarian carcinomas, as well as NCI/ADR-RES, a drug-resistant ovarian carcinoma line (For years, NCI/ADR-RES cells have been misidentified as drug-resistant MCF-7 breast adenocarcinoma cells, but recently this line has been shown definitively to be a drug-resistant line derived from OVCAR-8 ovarian adenocarcinoma cells. Liscovitch, M. et al., Cancer Lett. (2007) 245, 350-352. The data clearly show that the structure of the glycosidic linkage affects both the potency and selectivity of neoglycosides. Digitoxin displayed strong, non-specific cytotoxicity toward the four cell lines tested, and MeON-glycosides 3α and 4α displayed a cytotoxicity profile similar to digitoxin, in accord with previous results (Langenhan, J. M. et al., J. S. Proc. Natl. Acad. Sci. (2005) 102, 12305-12310.) However, EtON—, AllylON—, and BnON-glycosides (3b/4b, 3e/4e. 3f/4f, respectively) were markedly less potent cytotoxins than digitoxin or MeON-glycosides 3a and 4a; like digitoxin, 3a, and 4a, they were also non-specific.

Most significantly, iPrON-glycosides 3c and 4c displayed enhanced selectivity relative to digitoxin and MeON-glycosides 3a and 4a. Specifically, while 3c and 4c were only modestly cytotoxic toward lung, colorectal, and ovarian carcinomas, these molecules were five to six times more potent cytotoxins against NCI/ADR-RES cells ($IC_{50}$=110±20 nM and 120±10 nM, respectively) than any other cell line tested. This may be the first observation cell line selectivity resulting from a simple alteration of glycosidic linkage. This outcome is particularly important since NCI/ADR-RES is a multi-drug resistant line that has high levels of P-glycoprotein expression (Liscovitch, M. et al., Cancer Lett. (2007) 245, 350-352.) While cardiac glycosides are generally substrates for P-glycoprotein, such tumor specificity suggests that 3c and 3d may no longer serve as P-glycoprotein substrates. Alternatively, the iPrON-glycosides may be interacting with a unique cellular target (Tanigawara, Y. et al., J. Pharmacol. Exp. Ther. (1992), 263, 840-845). Supporting this notion, neoglycosides have previously been shown to be significantly less potent $Na^+/K^+$-ATPase inhibitors in HEK-239 human embryonic kidney cells than digitoxin (Langenhan, J. M. et al., J. S. Proc. Natl. Acad. Sci. (2005), 102, 12305-12310.) Also, digitoxin itself can target cellular components in addition to Na⁺/K⁺-ATPase (Johnson, P. H. et al., J. Mol. Cancer. Ther. (2002) 1, 1293 1304; Komentiani, P. et al., Mol. Pharmacol. (2005) 67, 929-936) such as the TNF-α/NF-κB signaling pathway, a regulator of inflammation responses relevant to cancer therapy (Yang, Q. et al., Proc. Natl. Acad. Sci. (2005) 102, 9631-9636.) Neoglycosides 3a-c and 4a-c were more potent cytotoxins than the corresponding aglycons (2a-c), confirming the importance of sugar attachments to the cytotoxicity of cardiac neoglycosides (data not shown).

Scheme 8

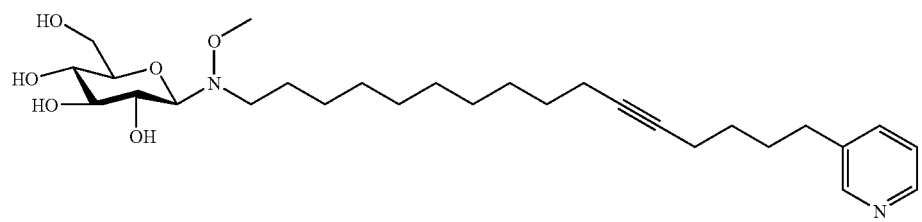

Amphlmedoside A

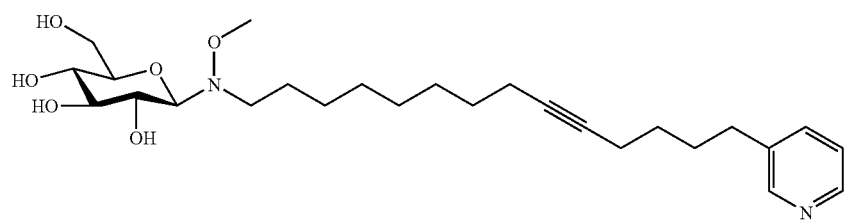

Amphlmedoside B

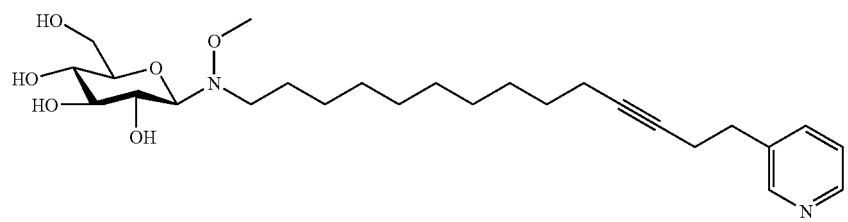

Amphlmedoside C

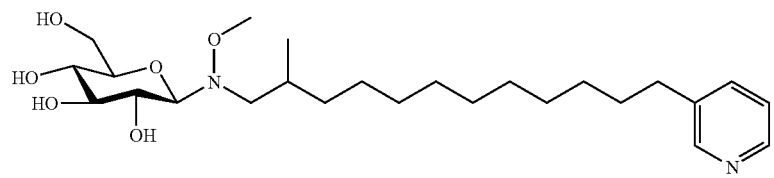

Amphlmedoside D

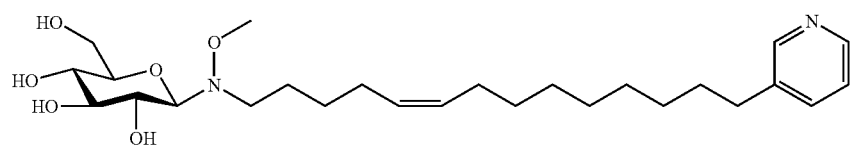

Amphlmedoside E

Amphidmedosides are a new class of natural products recently isolated in small quantities from marine sponges, and preliminary data suggests these molecules may be potent anti-cancer agents (Takekawa, Y, et al., J. Nat. Prod. (2006) 69, 1503-1505). The present invention can be used to synthesize the above amphimedisides as well as amphemedoside derivatives having different NOR linkages and different sugars.

The following is a retrosynthetic analysis outlining the general strategy for synthesizing ampimedoside B. The same general strategy could be used to synthesize a variety of amphimedosides, including amphimedosides A-E and additional derivatives containing different sugars and/or NOR linkages rather than the natural NOMe linkage. Many of the steps for synthesizing the aglycon are based on work reported in Goundry, W. R. F., et al., Tetrahedron (2003) 59, 1719-1729.

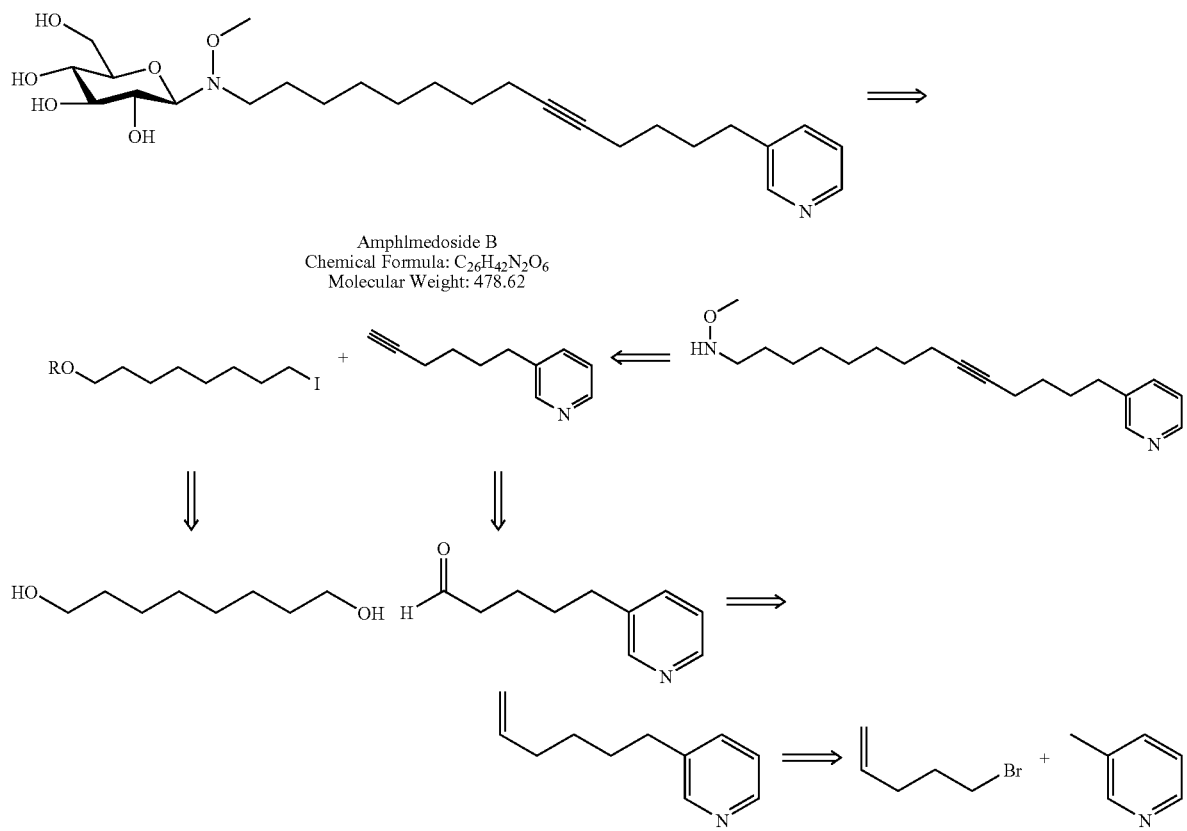

The inventor has initiated the syntheses of amphimedosides A, B, and C, and the following reaction sequences illustrate the progress that has been made in these syntheses.

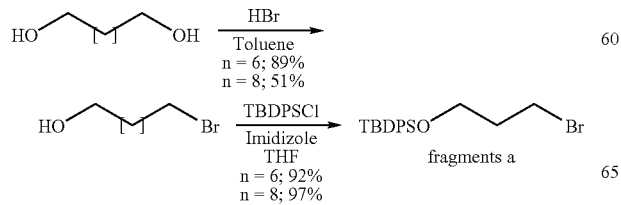

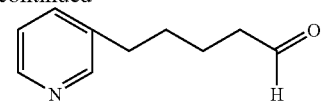

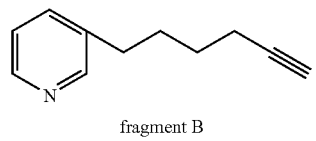

In summary, a mild, chemoselective reaction is presented between oxyamines and unprotected, unactivated reducing sugars to construct for the first time a panel of linkage-diversified neoglycosides. This modestly-sized panel of digitoxin analogs included tumor-selective cytotoxins, validating linkage diversification through neoglycosylation as a unique and simple strategy to powerfully complement existing methods for the optimization of glycoconjugates.

Experimental details, characterization of data synthesis description of the new compounds, and complete cytotoxicity assay data are provided in the following section.

I. General Procedures

Proton nuclear magnetic resonance ($^1$H NMR) spectra were recorded in deuterated solvents on a 300 MHz or 400 MHz spectrometer. Chemical shifts are reported in parts per million (ppm, δ) relative to tetramethylsilane (0.00) for d-chloroform, or the residual protic solvent peak for other solvents. $^1$H NMR splitting patterns with observed first order coupling are designated as singlet (s), doublet (d), triplet (t), or quartet (q). Splitting patterns that could not be interpreted or easily visualized are designated as multiplet (m), broad (br), or apparent (a). Carbon nuclear magnetic resonance ($^{13}$C NMR) spectra were recorded on a 300 MHz or 400 MHz spectrometer. Mass spectra (MS) were obtained using electrospray ionization. Commercially available reagents and solvents were used without further purification. Analytical thin layer chromatography (TLC) was carried out on TLC plates pre-coated with silica gel 60 (250 μm layer thickness). Visualization was accomplished using either a UV lamp or potassium permanganate stain (2 g $KMnO_4$, 13.3 g $K_2CO_3$, 2 mL 2M NaOH, 200 mL $H_2O$). Flash column chromatography was performed on 40-60 μm silica gel (230-400 mesh). Solvent mixtures used for TLC and flash column chromatography are reported in v/v ratios.

II. Synthesis

Digitoxigenone. Jones reagent was prepared by mixing $CrO_3$ (21.03 g), $H_2SO_4$ (18.6 mL), and water (57 μL). This reagent was slowly added to an Erlenmeyer flask containing digitoxin (10.0 g, 13.1 mmol) and suspended in acetone (650 mL) at 0° C. The resulting mixture was stirred for 3 h at rm temp. The mixture was then cooled to 0° C., quenched with approximately 30 mL MeOH, stirred for 20 min, and 30 mL water was added. Volatile solvents were removed under reduced pressure, and the aqueous mixture was extracted with chloroform (4×70 mL). The combined organic layers were washed with sat. aq. $NaHCO_3$, two times with water, dried over $Na_2SO_4$, filtered, then concentrated. The product ketone digitoxigenone (3.06 g, 63% yield), obtained as a white foam (TLC $R_f$=0.23 in 3:2 EtOAc/hexane), was used without further purification. $^1$H NMR ($CDCl_3$, 400 MHz) δ 5.89 (s, 1H), 5.03 (A of ABX, 1H, J=18.2, 1.5), 4.94 (B of ABX, 1H, J=18.2, 1.7), 2.82 (m, 1H), 2.65 (dd, 1H, J=14.5), 2.37 (td, 1H, J=14.8, 5.4), 2.17 (m, 4H), 2.04 (m, 2H), 1.96-1.73 (m, 6H), 1.67 (m, 1H), 1.61-1.23 (m, 7H), 1.02 (s, 3H), 0.92 (s, 3H); $^{13}$C NMR ($CDCl_3$, 100 MHz): δ 212.9, 175.0, 174.7, 117.5, 85.0, 77.4, 73.6, 50.8, 49.7, 43.7, 42.1, 41.4, 39.7, 37.1, 36.7, 36.5, 35.2, 33.0, 26.9, 26.5, 22.5, 21.2, 20.9, 15.8; Electrospray ionization-MS m/z (M+H) calculated for $C_{23}H_{33}O_4$ 373.5, observed 373.2.

General Procedure for Generation of Aglycons (2). Digitoxigenone (9.48 g, 25.5 mmol) was dissolved in methanol (2.2 mL/mmol) and pyridine (2.2 eq.). Oxyamine hydrochloride (1.6 eq.) was added, and the solution was stirred for 2.5 hours then concentrated. The resulting residue was dissolved in $CH_2Cl_2$ and washed with 1 M HCl brine, dried over $MgSO_4$, filtered, and then concentrated. The mixture of oxime diastereomers (1 eq.) was suspended in ethanol (2.9 mL/mmol) and cooled to 0° C. Borane tert-butylamine complex (3.3 eq.) was added, followed by the dropwise addition 10% aq. HCl (2.7 mL/mmol). The reaction mixture was stirred at 0° C. for 2.5 hours. After this time, $Na_2CO_3$ was added until gas evolution ceased, and the mixture was partitioned between water and $CHCl_3$. The organic layer was washed with brine, dried over $MgSO_4$, filtered, and concentrated. The resulting diastereomeric mixture was resolved via $SiO_2$ column chromatography.

Preparation of ethoxyamines 2a. See Langenhan, J. M. et al., Proc. Natl. Acad. Sci. (2005) 102, 12305-12310.

Preparation of ethoxyamines 2b & 2bα. Via the general procedure, digitoxigenone (200 mg, 0.537 mmol) was converted a mixture of ethoxyamine diastereomers. The mixture was purified by $SiO_2$ column chromatography eluting with 1:1 EtOAc/hexane to elute 2b (β-isomer) (TLC $R_f$=0.24 in 1:1 EtOAc/hexane) and then with 3:2 EtOAc/hexane to elute 2bα (α-isomer) (TLC $R_f$=0.07 in 1:1 EtOAc/hexane).

Aglycon 2b was obtained as a foam (76.5 mg, 44% yield). $^1$H NMR ($CDCl_3$, 300 MHz) δ 5.87 (m, 1H), 5.01 (A of ABX, 1H, J=18.1, 1.2), 4.82 (B of ABX, 1H, J=18.1, 1.7), 3.73 (q, 2H), 3.24 (br s, 1H), 2.79 (m, 1H), 2.15 (m, 2H), 1.85 (m, 3H), 1.73-1.22 (m, 17H), 1.17 (t, 3H), 0.94 (s, 3H), 0.87 (s, 3H); $^{13}$C NMR ($CDCl_3$, 100 MHz): δ 174.9, 174.6, 117.5, 85.5, 73.5, 69.6, 55.0, 50.9, 49.6, 41.8, 40.0, 36.6, 35.6, 35.5, 33.1, 30.4, 28.7, 26.9, 26.6, 25.3, 23.7, 21.2, 21.0, 15.8, 14.3; Electrospray ionization-MS m/z (M+H) calculated for $C_{25}H_{39}NO_4$ 418.3, observed 418.3.

Aglycon 2bα (undesired α-isomer) was obtained as a foam (69.5 mg, 40% yield). $^1$H NMR ($CDCl_3$, 300 MHz) δ 5.87 (s, 1H), 5.00 (A of ABX, 1H, J=18.1, 1.4), 4.82 (B of ABX, 11H, J=18.1, 1.5), 3.74 (q, 2H), 2.91 (m, 1H), 2.77 (m, 1H), 2.16 (m, 2H), 1.85 (m, 3H), 1.74-1.22 (m, 17H), 1.18 (t, 3H), 0.94 (s, 3H), 0.87 (s, 3H); $^{13}$C NMR ($CDCl_3$, 100 MHz): δ 174.9, 174.7, 117.7, 85.6, 77.4, 73.6, 70.1, 60.6, 51.1, 49.7, 42.1, 41.7, 40.1, 36.4, 35.6, 35.3, 33.4, 31.3, 27.3, 27.0, 25.6, 23.6, 21.7, 21.1, 15.9, 14.4.

Preparation of iso-propoxyamines 2c & 2cα. Via the general procedure, digitoxigenone (200 mg, 0.537 mmol) was converted a mixture of iso-propoxyamine diastereomers. The mixture was purified by $SiO_2$ column chromatography eluting with 2:3 EtOAc/hexane to elute 2c (β-isomer) (TLC $R_f$=0.30 in 2:3 EtOAc/hexane) and then 2cα (α-isomer) (TLC $R_f$=0.16 in 2:3 EtOAc/hexane):

Aglycon 2c was obtained as a foam (62.5 mg, 32% yield). $^1$H NMR ($CDCl_3$, 300 MHz) δ 5.87 (m, 1H), 5.01 (A of ABX, 1H, J=18.0, 1.3), 4.91 (B of ABX, 1H, J=18.0, 1.6), 3.81 (sept, 11H), 3.20 (br s, 1H), 2.77 (m, 1H), 2.16 (m, 2H), 1.86 (m, 3H), 1.73-1.22 (m, 17H), 1.14 (d, 6H), 0.93 (s, 3H), 0.87 (s, 3H); $^{13}$C NMR ($CDCl_3$, 100 MHz): δ 175.0, 174.7, 117.7, 85.7, 77.4, 74.8, 73.6, 55.2, 51.1, 49.8, 42.0, 40.2, 36.8, 35.8, 35.6, 33.3, 30.6, 29.0, 27.0, 26.8, 23.9, 21.5, 21.3, 21.2, 15.9; Electrospray ionization-MS m/z (M+H) calculated for $C_{26}H_{41}NO_4$ 432.3, observed 432.4.

Aglycon 2cα (undesired α-isomer) was obtained as a foam (66.9 mg, 34% yield). $^1$H NMR ($CDCl_3$, 300 MHz) δ 5.87 (s, 1H), 5.00 (A of ABX, 1H, J=18.1, 1.6), 4.81 (B of ABX, 1H, J=18.1, 1.7), 3.82 (sept, 1H), 2.87 (m, 1H), 2.77 (m, 1H), 2.15 (m, 2H), 1.84 (m, 3H), 1.74-1.22 (m, 17H), 1.15 (d, 6H), 0.93 (s, 3H), 0.87 (s, 3H); $^{13}$C NMR ($CDCl_3$, 100 MHz): δ 174.7, 174.6, 117.6, 85.5, 77.3, 75.2, 73.5, 60.5, 50.9, 49.6, 42.0, 41.6, 40.0, 36.3, 35.5, 35.3, 33.2, 31.3, 27.2, 26.9, 25.6, 23.5, 21.6, 21.4, 20.9, 15.8.

Preparation of tert-butoxyamines 2d & 2dα. Via the general procedure, digitoxigenone (200 mg, 0.537 mmol) was converted a mixture of tert-butoxyamine diastereomers. The mixture was purified by $SiO_2$ column chromatography eluting with 1:4 EtOAc/toluene to elute 2d (β-isomer) (TLC $R_f$=0.19 in 1:4 EtOAc/toluene) and then 2dα (α-isomer) (TLC $R_f$=0.14 in 1:4 EtOAc/toluene).

Aglycon 2d was obtained as a white solid (37.2 mg, 25% yield). $^1$H NMR (CDCl$_3$, 300 MHz) δ 5.87 (br t, 1H), 5.00 (A of ABX, 1H, J=17.9, 1.3), 4.81 (B of ABX, 1H, J=17.9, 1.7), 3.12 (br s, 1H), 2.78 (m, 1H), 2.16 (m, 2H), 1.86 (m, 3H), (m, 17H), 1.18 (s, 9H), 0.93 (s, 3H), 0.87 (s, 3H); $^{13}$C NMR (CDCl$_3$, 100 MHz): δ 174.8, 174.7, 117.8, 85.8, 76.5, 73.6, 55.2, 51.1, 49.8, 42.1, 40.2, 36.9, 35.8, 35.6, 33.4, 30.8, 29.0, 27.2, 27.1, 26.8, 24.0, 23.1, 21.4, 21.3, 15.9; Electrospray ionization-MS m/z (M+H) calculated for C$_{27}$H$_{43}$NO$_4$ 446.3, observed 446.4.

Aglycon 2dα (undesired α-isomer) was obtained as a white solid (83.8 mg, 57% yield). $^1$H NMR (CDCl$_3$, 300 MHz) δ 5.87 (s, 1H), 5.00 (A of ABX, 1H, J=18.0, 1.3), 4.81 (B of ABX, 1H, J=18.0, 1.4), 4.71 (br s 1H), 2.77 (m, 2H), 2.15 (m, 2H), (m, 20H), 1.17 (s, 9H), 0.93 (s, 3H), 0.87 (s, 3H); $^{13}$C NMR (CDCl$_3$, 100 MHz): δ 174.9, 174.7, 117.7, 85.6, 77.4, 76.4, 73.6, 60.5, 51.1, 49.7, 42.1, 41.9, 40.1, 36.4, 35.6, 35.5, 31.7, 31.7, 27.3, 27.1, 26.0, 23.7, 21.7, 21.1, 15.9.

Preparation of allyloxyamines 2e & 2eα. Via the general procedure, digitoxigenone (200 mg, 0.537 mmol) was converted a mixture of allyloxyamine diastereomers. The mixture was purified by SiO$_2$ column chromatography eluting with 2:3 EtOAc/toluene to elute 2e (β-isomer) (TLC $R_f$=0.24 in 2:3 EtOAc/hexane) and then 2eα (α-isomer) (TLC $R_f$=0.08 in 2:3 EtOAc/hexane).

Aglycon 2e was obtained as a white solid (70.2 mg, 41% yield). $^1$H NMR (CDCl$_3$, 300 MHz) δ 5.94 (ddt, 1H, J=17.4, 10.3, 6.0), 5.87 (br t, 1H), 5.44 (br s, 1H), 5.27 (ddt, 1H, J=17.3, 3.3, 1.6), 5.18 (ddt, 1H, J=10.4, 1.9, 1.0), 5.01 (A of ABX, 1H, J=18.2, 1.4), 4.82 (B of ABX, 1H, J=18.2, 1.7), 4.19 (dt, 2H, J=5.9, 1.3), 3.27 (br s, 1H), 2.79 (m, 1H), 2.16 (m, 2H), 1.86 (m, 3H), 1.73-1.22 (m, 17H), 0.93 (s, 3H), 0.87 (s, 3H); $^{13}$C NMR (CDCl$_3$, 100 MHz): δ 175.0, 174.7, 134.7, 117.8, 117.6, 85.6, 75.6, 73.6, 55.2, 51.1, 49.8, 41.9, 40.1, 36.7, 35.8, 35.6, 33.3, 30.5, 28.8, 27.0, 26.7, 23.9, 22.9, 21.3, 21.2, 15.9; Electrospray ionization-MS m/z (M+H) calculated for C$_{26}$H$_{39}$NO$_4$ 430.3, observed 430.3.

Aglycon 2eα (undesired α-isomer) was obtained as a white solid (64.0 mg, 36% yield). $^1$H NMR (CDCl$_3$, 300 MHz) δ 5.94 (ddt, 1H, J=17.3, 10.5, 5.9), 5.87 (br t, 1H), 5.45 (br s, 1H), 5.28 (ddt, 1H, J=17.3, 3.3, 1.5), 5.20 (ddt, 1H, J=10.4, 2.3, 1.2), 5.00 (A of ABX, 1H, J=18.2, 1.3), 4.81 (B of ABX, 1H, J=18.2, 1.7), 4.21 (dt, 2H, J=5.8, 1.3), 2.93 (m, 1H), 2.77 (m, 1H), 2.15 (m, 2H), 1.86 (m, 3H), 1.76-1.22 (m, 17H), 0.93 (s, 3H), 0.87 (s, 3H); $^{13}$C NMR (CDCl$_3$, 100 MHz): δ 174.9, 174.7, 134.5, 117.7, 117.6, 85.6, 75.8, 73.6, 60.6, 51.0, 49.7, 42.1, 41.7, 40.1, 36.4, 35.6, 35.3, 31.3, 27.2, 26.0, 25.6, 23.6, 21.7, 21.1, 15.9.

Preparation of benzyloxyamines 2f & 2fα. Via general procedures, digitoxigenone (200 mg, 0.537 mmol) was converted a mixture of benzyloxyamine diastereomers. The mixture was purified by SiO$_2$ column chromatography eluting with 2:3 EtOAc/toluene to elute 2f (β-isomer) (TLC $R_f$=0.24 in 2:3 EtOAc/hexane) and then 2fα (α-isomer) (TLC $R_f$=0.13 in 2:3 EtOAc/hexane).

Aglycon 2f was obtained as a foam (77.5 mg, 37% yield). $^1$H NMR (CDCl$_3$, 400 MHz) δ 7.31 (m, 5H), 5.86 (s, 1H), 5.43 (br s, 1H), 5.00 (A of ABX, 1H, J=18.1, 1.4), 4.81 (B of ABX, 1H, J=18.1, 1.8), 4.70 (s, 2H), 3.29 (s, 1H), 2.77 (m, 1H), 2.15 (m, 2H), 1.85 (m, 3H), 1.74-1.22 (m, 17H), 0.94 (s, 3H), 0.86 (s, 3H); $^{13}$C NMR (CDCl$_3$, 100 MHz): δ 175.0, 174.7, 138.2, 128.6, 128.4, 127.9, 117.7, 85.6, 73.6, 55.1, 51.1, 49.8, 41.9, 40.1, 36.7, 35.8, 35.6, 33.3, 30.5, 28.8, 27.0, 26.7, 23.9, 23.0, 21.3, 21.2, 15.9; Electrospray ionization-MS m/z (M+H) calculated for C$_{30}$H$_{41}$NO$_4$ 480.3, observed 404.4.

Aglycon 2fα (undesired α-isomer) was obtained as a white powder (73.1 mg, 35% yield). $^1$H NMR (CDCl$_3$, 400 MHz) δ 7.32 (m, 5H), 5.87 (br t, 1H), 5.48 (br s, 1H), 4.99 (A of ABX, 1H, J=18.1, 1.4), 4.81 (B of ABX, 1H, J=18.1, 1.8), 4.73 (s, 2H), 2.96 (m, 1H), 2.77 (m, 1H), 2.15 (m, 2H), 1.84 (m, 3H), 1.86-1.00 (m, 17H), 0.93 (s, 3H), 0.86 (s, 3H); $^{13}$C NMR (CDCl$_3$, 100 MHz): δ 174.8, 174.7, 138.0, 128.5, 128.4, 128.0, 117.7, 85.6, 77.1, 73.6, 60.6, 51.1, 49.7, 42.1, 41.7, 40.1, 36.4, 35.6, 35.4, 33.4, 31.2, 27.3, 27.0, 25.6, 23.6, 21.7, 21.1, 15.9.

Neoglycosides. Aglycons 2b-2f (1 eq., approximately 30 μmol) either L-ribose or L-xylose (1.1 eq., approximately 33 μmol) added to glass vials equipped with stirring fleas and were dissolved in 9:1 MeOH/CHCl$_3$ (final concentration of aglycon=100 mmol). AcOH was added (1 eq., approximately 2 μL) and the reaction mixtures were stirred at 40° C. for 4 days. The crude reaction mixtures were concentrated, then suspended in 2% MeOH in CHCl$_3$. The crude suspensions were purified in parallel on disposable SiO$_2$ solid-phase extraction columns using a 24-port vacuum manifold. Three treatments with 2 mL of 3% MeOH/CH$_2$Cl$_2$ eluted unreacted aglycon and five treatments with 2 mL of 5% MeOH/CH$_2$Cl$_2$ eluted products 3 and 4.

Aglycon 2a was reacted with L-ribose and L-xylose using previously reported methodology (Langenhan, J. M. et al., Proc. Natl. Acad. Sci. (2005) 102, 12305-12310.) The product solutions were concentrated, weighed, and dissolved in DMSO to make 30 mM stock solutions. The stock solutions were characterized by LCMS using reverse phase HPLC on a Zorbax Eclipse XDB-C8 column (4.6×150 mm; Agilent Technologies) with a flow rate of 0.8 mL/min and a linear gradient of 45% CH$_3$OH/H$_2$O to 85% CH$_3$OH/H$_2$O over 20 min and electrospray ionization. Percent purity was estimated by dividing the sum of the peak areas at 220 nm of peaks corresponding to the desired product mass by the total area of all peaks between 5 and 22 min. Reported masses are [M+H]. A summary of neoglycoside yields, mass data, purities, and isomer ratios is shown below in Table 6.

TABLE 6

LCMS information for neoglycoside panel

| Neoglycoside | Isolated Yield | Calculated Mass | Observed Mass | Percent Purity | Isomer ratio |
|---|---|---|---|---|---|
| 3a | 78 | 536.7 | 536.6 | 98 | — |
| 3b | 61 | 550.7 | 550.5 | 98 | ~34:34:1 (overlap) |
| 3c | 8 | 564.7 | 564.4 | 96 | 44:1 |
| 3d | 0 | — | — | — | — |
| 3e | 7 | 562.7 | 562.5 | 64 | 52:1 |
| 3f | 19 | — | — | — | — |
| 4a | 53 | 536.7 | 536.6 | 99 | 100:0 |
| 4b | 52 | 550.7 | 550.5 | 98 | 46:1 |
| 4c | 17 | 564.7 | 564.4 | 96 | 68:1:1 |
| 4d | 0 | — | — | — | — |
| 4e | 12 | 562.7 | 562.5 | 65 | 10:1 |
| 4f | 40 | 612.8 | 612.4 | 95 | 48:3:1:1 |

II. Cytotoxicity Assays

All cell lines were maintained as previously reported (Langenhan, J. M. et al., Proc. Natl. Acad. Sci. (2005) 102, 12305-12310.) Cells were harvested by trypsinization using 0.25% trypsin and 0.1% EDTA and then counted in a Cellometer Auto T4 cell counter (Nexcelom, inc), before dilution for assay plating. Cell plating, compound handling and assay set up were performed as previously reported[1] except for the cells were plated in 50 µL volumes in 384 well clear bottom, tissue culture plates (Corning-Costar, Inc). Compounds were added from the 384-well compound stock plates at a 1:100 dilution using a Biomek FX liquid handler equipped with a 384 channel head (Beckman Coulter, Inc.). Cell titer-glo reagent (15 µL) (Promega Corporation, Inc.) was added and incubated for 10 min at room temperature with gentle agitation to lyse the cells. Each plate was read for luminescence. The $IC_{50}$ value for each compound represents at least four replicates of dose-response experiments conducted over six concentrations at two-fold dilutions. Within each experiment, percent inhibition values at each concentration were expressed as a percentage of the maximum luminescence signal observed for a 0 nM control. $IC_{50}$ values were determined using XLFit 4.0 as previously reported (see Table 7).

TABLE 7

$IC_{50}$s (µM) and standard errors for neoglycoside cytotoxicity against four cell lines.

| | Compound | | 3a | 4a | 3b | 4b | 3c | 4c | 3e | 4e | 3f | 4f | 1 |
|---|---|---|---|---|---|---|---|---|---|---|---|---|---|
| Cell Line | SKOV-3 | IC50 | >1 | >1 | 0.12 | 0.20 | 0.73 | 0.68 | 0.71 | 0.61 | 0.92 | >1 | >1 |
| | | SE | | | 0.01 | 0.02 | 0.06 | 0.06 | 0.06 | 0.06 | 0.05 | | |
| | NCI-H460 | IC50 | ? | 0.055 | 0.16 | 0.18 | 0.67 | 0.63 | 0.71 | 0.63 | 0.69 | 0.76 | — |
| | | SE | | 0.006 | 0.01 | 0.01 | 0.05 | 0.05 | 0.05 | 0.04 | 0.04 | 0.05 | |
| | NCI/ADR-RES | IC50 | 0.045 | 0.072 | 0.14 | 0.19 | 0.11 | 0.12 | 0.42 | 0.46 | 1.0 | 1.0 | 0.069 |
| | | SE | 0.005 | 0.006 | 0.01 | 0.01 | 0.02 | 0.01 | 0.06 | 0.04 | 0.1 | 0.1 | 0.006 |
| | HT-29 | IC50 | 0.08 | 0.066 | 0.20 | 0.22 | 0.85 | 0.84 | 0.95 | 0.91 | 1.7 | 2.0 | — |
| | | SE | 0.01 | 0.004 | 0.02 | 0.02 | 0.04 | 0.05 | 0.05 | 0.05 | 0.2 | 0.2 | |

While the present invention has been described in what is perceived to be the most practical and preferred embodiments and examples, it is to be understood that the invention is not intended to be limited to the specific embodiments set forth above. Further, it is recognized that modifications may be made by one of skill in the art of the invention without departing from the spirit or intent of the invention and, therefore, the invention is to be taken as including all reasonable equivalents to the subject matter of the appended claims. All references cited herein are incorporated by reference for all purposes.

I claim:

1. A neoglycoside library comprising at least two different neoglycosides having the structure:

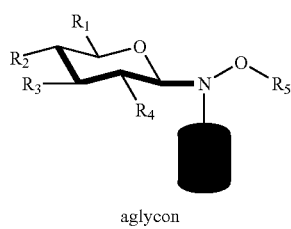

aglycon wherein: $R_1$, $R_2$, $R_3$, and $R_4$ of the sugar are independently selected from —H, —OH, —$N_3$, —$NH_2$, —$CH_3$, —$CH_2OH$, —$CN_3$, —$CH_2NH$, —$CH_2SH$, —$CNH_2$, —$CH_2N_3$, —COOH, —$COCH_3$, —$CXH_2$, or —$CX_2H$, where X is Cl, Br, F, or I; $R_5$ is —$CH_3$, —$CH_2CH_3$, —$CH(CH_3)_2$, allyl, benzyl, —$CH_2CH_2CH_3$, —$CH(CH_3)CH_2CH_3$, —$C(CH_3)_3$, cyclopentyl or cyclohexyl; and the aglycon is a cardiac glycoside aglycon, a non-digoxigenin steroid, an indolocarbazole, an anthracyline, or a macrolide.

2. A method of making a neoglycoside library comprising the steps of:

providing a plurality of reducing sugars having the structure:

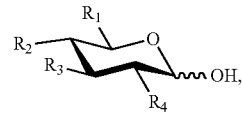

wherein $R_1$, $R_2$, $R_3$ and $R_4$ are independently selected from —H, —OH, —$N_3$, —$NH_2$, —$CH_3$, —$CH_2OH$, —$CN_3$, —$CH_2NH$, —$CH_2SH$, —$CNH_2$, —$CH_2N_3$, —COOH, —$COCH_3$, —$CXH_2$, or —$CX_2H$, where X is Cl, Br, F, or I; and contacting the reducing sugars with at least one aglycon having a secondary oxyamine of formula >N—O—$R_5$ wherein $R_5$ is —$CH_3$, —$CH_2CH_3$, —$CH(CH_3)_2$, allyl, benzyl, —$CH_2CH_2CH_3$, —$CH(CH_3)CH_2CH_3$, —$C(CH_3)_3$ cyclopentyl or cyclohexyl, and wherein the aglycon is a cardiac glycoside aglycon, a non-digoxigenin steroid, an indolocarbazole, an anthracyline, or a macrolide, to form a plurality of neoglycosides.

3. The method of claim 2 wherein the aglycon is:

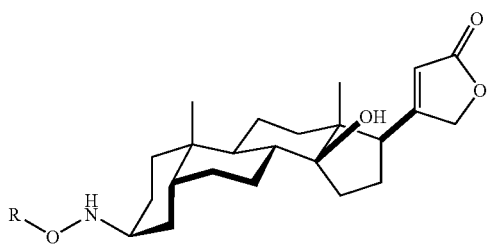

wherein R is —$CH_3$, —$CH_2CH_3$, —$CH(CH_3)_2$, —$C(CH_3)_3$, allyl, benzyl, —$CH_2CH_2CH_3$, —$CH(CH_3)CH_2CH_3$, cyclopentyl or cyclohexyl.

* * * * *